United States Patent [19]

Gutnick et al.

[11] 4,230,80

[45] Oct. 28, 19

[54] PRODUCTION OF α-EMULSANS

[75] Inventors: David L. Gutnick, Ramat Aviv; Eugene Rosenberg, Raanana, both of Israel

[73] Assignee: Biotechnologie Aktiengesellschaft für Emulsan, Basel, Switzerland

[21] Appl. No.: 12,974

[22] Filed: Feb. 22, 1979

[51] Int. Cl.² ............................................. C12P 19/04
[52] U.S. Cl. ...................................... 435/101; 435/281; 210/611; 210/925
[58] Field of Search ............... 435/101, 830, 281, 822; 210/2, 11, 18, 15, DIG. 27

[56] References Cited

U.S. PATENT DOCUMENTS

| | | | |
|---|---|---|---|
| 3,941,692 | 3/1976 | Gutnick et al. | 435/281 |
| 3,997,398 | 12/1976 | Zajic et al. | 435/101 |

OTHER PUBLICATIONS

Reisfeld A. et al., "Applied Microbiology", 24, 363 (1972).
Englander E. et al., "Int. Assoc. Microbiol. Soc. Abstracts", vol. II, p. 201 (1973).
Rosenberg E. et al., "EPA Report 600-3-75-001", pp. 157-168 (Dec. 1974).
Horowitz A. et al., "Applied Microbiology", 30, (1975).

*Primary Examiner*—Benoît Castel
*Attorney, Agent, or Firm*—Pennie & Edmonds

[57] ABSTRACT

Growth of Arthrobacter Sp. ATCC 31012 on fatty ac substrates produces a new class of extracellular micr bial protein-associated lipopolysaccharides (the " emulsans"). Deproteinization of α-emulsans by hot ph nol extraction produces the lipopolysaccharide comp nents (the "apo-α-emulsans") of such emulsans, whi components have been shown to be completely ] acylated and partially O-acylated heteropolysacch rides made up of major amounts of D-galactosami and an aminouronic acid, such apo-α-emulsans contai ing at least 5 percent by weight of O-substituted fat acid esters in which the fatty acids contain from abo 10 to about 18 carbon atoms. α-Emulsans and apo- emulsans, both of which biopolymers are strongly a ionic, exhibit a high degree of specificity in the emulsi cation of hydrocarbon substrates which contain bo aliphatic and cyclic components. In addition, these e tracellular microbial polysaccharides as well as the O-deacylated and N-deacylated derivatives are a sorbed on and capable of flocculating aluminosilica ion-exchangers, such as kaolin and bentonite.

23 Claims, 18 Drawing Figures

PRODUCTION OF α-EMULSANS

TABLE OF CONTENTS

1. Introduction
2. Background of the Invention
3. Summary of the Invention
4. Nomenclature
5. Brief Description of the Drawings
6. Production of α-Emulsans and Apo-α-emulsans
   6.1. Acinetobacter Sp. ATCC 31012
   6.2 Fermentation Media
      6.2.1. Utilizable Carbon Sources
      6.2.2. Additional Nutrients
      6.2.3. Divalent Cations
   6.3 Fermentation Process Conditions
      6.3.1. Aeration
      6.3.2. Agitation
      6.3.3. Temperature and pH
      6.3.4. Defoaming
   6.4. Extracellular Production of Emulsans
      6.4.1. Standard Assay for Emulsifying Activity
      6.4.2. Extracellular Production of α-Emulsans
      6.4.3. Extracellular Production of β-Emulsans
      6.4.4. Distribution of Emulsifying Activity in Fractions of Growth Culture
   6.5. Deproteinization
   6.6 Isolation and Purification
      6.6.1. Heptane Partitioning
      6.6.2. Ammonium Sulfate Precipitation
      6.6.3. Quaternary Ammonium Salt Precipitation
7. Chemical and Physical Properties of Emulsans and Apoemulsans
   7.1. Preparation of Samples for Analytical Characterization
      7.1.1. Preparation of Emulsan Samples
      7.1.2. Preparation of Apoemulsan Samples
      7.1.3. Ammonium Sulfate Fractionation of Apo-α-Emulsan
      7.1.4. Quaternary Ammonium Salt Precipitation of Apo-α-Emulsan
   7.2. Chemical Characterization
      7.2.1. Chemical Composition of Emulsans and Apoemulsans
      7.2.2. Alkaline Hydrolysis of Emulsans and Apoemulsans
      7.2.3. Acid Hydrolysis of Apoemulsans and of Proemulsans
      7.2.4. Identification of Sugar Components
      7.2.5. Identification of Fatty Acids
   7.3. Physical Characterization
      7.3.1. Intrinsic and Reduced Viscosity
      7.3.2. Sedimentation Velocity Analysis
      7.3.3. Estimation of Molecular Weight
      7.3.4. Spectral Properties
   7.4 Conclusions on Structure
   7.5 Variations in Structure
   7.6. Immunological Characterization
8. Emulsifying Properties
   8.1. Kinetics of Emulsan-Induced Emulsion Formation
   8.2. Effect of pH and Salt Concentration on Emulsion Formation
   8.3. Stability of Emulsan-Induced Emulsions
   8.4. Lowering of Oil/Sea Water Interfacial Tensions
9. Specificity of the Hydrocarbon Substrate
   9.1. Emulsification of Petroleum Fractions
   9.2. Emulsification of Pure Hydrocarbons
   9.3. Emulsification of Mixtures of Pure Hydrocarbons
   9.4. Effect of Addition of Aliphatic and Aromatic Compounds on Emulsification of Petroleum Fractions
10. Summary of Differences Between α-Emulsans and β-Emulsans
    10.1. Differences in Yield
    10.2. Differences in Structure
    10.3. Differences in Emulsifying Activity
11. Sorptive Properties of Emulsans and Their Derivatives on Solid Substrates
    11.1. Non-Adsorption on Sand and Limestone
    11.2. Adsorption on Aluminosilicate Clays
    11.3. Flocculation of Clays
    11.4. Relationship of Flocculation to Breaking Oil Water Emulsions
12. Environmental and Energy-Related Uses
13. Examples
    13.1. Best Mode for Preparation of α-Emulsan from Fatty Acid Salts
    13.2. Preparation of α-Emulsan from Sodium Palmitate
    13.3. Preparation of β-Emulsan from Hexadecane
    13.4. Preparation of Apo-α-Emulsan
    13.5. Preparation of Apo-β-Emulsan
    13.6. Preparation of Ψ-Emulsans
    13.7. Preparation of Proemulsan
    13.8. Purification of α-Emulsan by Precipitation with Ammonium Sulfate
    13.9. Purification of α-Emulsan by Precipitation with Quaternary Ammonium Salts
    13.10. Purification of β-Emulsan by Heptane Partitioning
    13.11. Ammonium Sulfate Fractionation of Apo-Emulsan
    13.12. Emulsification of Petroleum Fractions by Emulsans and β-Emulsans
    13.13. Emulsification of Mixtures of Petroleum Fractions and Pure Hydrocarbons by αEmulsan
    13.14. Cleaning Oil-Contaminated Vessels
    13.15. Effect of Mobility Control Polysaccharides Emulsion Formation with α-Emulsan
    13.16. Absorption of α-Emulsans on Clays
    13.17. Flocculation of Clays by Emulsans
    13.18. Flocculation of Clays by Proemulsan
    13.19. Breaking Emulsan-Induced Emulsions
    13.20. Removal of Oil from Sand by Emulsan
    13.21. Removal of Oil from Limestone by Emulsan

1. INTRODUCTION

This invention relates to extracellular microbial polysaccharides (herein generically called "emulsans") produced by Acinetobacter Sp. ATCC 31012 and, more particularly, to a process for the production of a new class of extracellular microbial protein-associated lipopolysaccharides (herein collectively called 'emulsans") produced by this organism and its mutants or recombinants. These extracellular microbial polysaccharides are among the most efficient oil-in-water emulsifiers ever discovered and possess a high degree of specificity in both fresh water and sea water for emulsifying those hydrocarbon substrates which contain both aliphatic and aromatic or cyclic components, properties which make these unique bioemulsifiers ideal for use in cleaning oil-contaminated vessels, oil spill management and enhanced oil recovery by chemical flooding.

2. BACKGROUND OF THE INVENTION wide variety of petroleum-degrading microorganisms has been found to bring about the formation of oil-water emulsions while growing on hydrocarbons. These emulsions are microbiological in origin and appear to be mediated either by the cells themselves or by production of extracellular emulsifying agents. For example, the growth of *Mycobacterium rhodochrous* NCIB 9905 on n-decane yields an emulsifying factor which was reported by R. S. Holdom et al. [J. Appl. Bacteriol., 32, 448 (1969)] to be a nonionic detergent. J. Iguchi et al. [Agric Biol. Chem., 33, 1657 (1969)] found that *Candida petrophilium* produced an emulsifying agent composed of peptides and fatty acid moieties, while T. Suzuki et al. [Agric. Biol. Chem., 33, 1619 (1969)] found trehalose lipid in the oil phase of culture broths of various strains of Arthrobacter, Brevibacterium, Corynebacterium and Norcardia. *Torulopsis gropengiesseri* was found to produce a sophorose lipid, while rhamnolipids are reported by K. Hisatsuka et al. [Agric. Biol. Chem., 35, 686 (1971)] to have been produced by *Pseudomonas aeruginosa* strain S7B1 and by S. Itoh et al. [Agric. Biol. Chem., 36, 2233 (1971)] to have been produced by another *P. aeruginosa* strain, KY4025. The growth of *Corynebacterium hydrocarbolastus* on kerosene was reported by J. E. Zajic and his associates [Dev. Ind. Microbiol., 12, 87 (1971); Biotechnol. Bioeng., 14, 331 (1972); Chemosphere, 1, 51 (1972); Crit. Rev. Microbiol., 5, 39 (1976);] U.S. Pat. No. 3,997,398 to produce an extracellular heteropolysaccharide which, among other properties, emulsified kerosene, Bunker C fuel oil and other fuel oils.

In U.S. Pat. No. 3,941,692, we described the use of an Arthrobacter species RAG-1 (which, upon deposit with American Type Culture Collection, has been designated as Arthrobacter Sp. ATCC 31012 and is now known to have been an Acinetobacter species and has been redesignated as Acinetobacter Sp. ATCC 31012) to clean oil-contaminated tank compartments by allowing the organism to aerobically grow on the oily wastes in such tanks using sea water containing added nutrients. During that microbially-induced cleaning process, the organism appeared to secrete one or more dispersants during the fermentation, since the cell-free fermentation medium was also effective in cleaning crude oil from such tanks.

Further studies on the microbial degradation of crude oil by this organism [Appl Microbiol., 24, 363 (1972); Appl. Microbiol., 30, 10 (1975)], showed that RAG-1 emulsified the oil during exponential growth, probably by producing an extracellular emulsifying agent which tended to break up the oil droplets into smaller units and thereby produce new surface area, necessary for the increasing cell population. At the 1st International Congress for Bacteriology held Sept. 2-7, 1973 [Int. Assoc. Microbiol. Soc. Abstracts, Vol. II, p. 201], we reported that this extracellular emulsifying agent had been partly purified from stationary phase cultures of RAG-1 growing on 0.4% hexadecene, 0.075 M urea and 5.8 mM dibasic potassium phosphate in sea water. The partially purified extracellular emulsifying agent was obtained by extensively dialyzing and then lyophilizing the cell-free fermentation broth, yielding 0.25 mg per ml of culture broth of a dry powder which was capable of forming a stable oil-in-water emulsion with 40 times its weight of crude oil.

Notwithstanding the many publications on the subject, however, microbially-induced emulsification of oil is poorly understood from both mechanistic and teleological points of view. Microorganisms can utilize crude oil as a substrate for growth with or without concomitant oil emulsification. Where emulsification has occurred because of the production of extracellular emulsifying agents, in general the preparations have not been purified sufficiently to identify the active components. In sum, none of these extracellular bioemulsifiers has been well characterized and very little is known about their chemical properties, mode of action or biological function.

3. SUMMARY OF THE INVENTION

The present invention is based upon part of a multitude of discoveries made in connection with further work done on the bioemulsifiers produced by Acinetobacter Sp. ATCC 31012, among the most important of which discoveries were:

Firstly, that the Acinetobacter bioemulsifier previously produced by growing Acinetobacter Sp. ATCC 31012 (also known as strain RAG-1) on crude oil or hexadecane is an extracellular microbial protein-associated lipopolysaccharide (which we have herein called "β-emulsan" and given the common name "protoemulsans"), in which the lipopolysaccharide is an N- and O-lipoacylated heteropolysaccharide made up of amounts of D-galactosamine and an aminouronic acid, the O-lipoacyl portion of the lipoheteropolysaccharide containing from 2 to 3 percent by weight of various fatty acid esters in which (a) the fatty acids contain from about 10 to about 18 carbon atoms; and (b) less than 50 percent by weight of such fatty acids are composed of 2-hydroxydodecanoic acid and 3-hydroxydodecanoic acid;

Secondly, that growth of Acinetobacter Sp. ATCC 31012 on ethanol as the primary assimilable carbon source yields a significantly different extracellular microbial protein-associated lipopolysaccharide (which we have herein called "α-emulsans"), in which the lipopolysaccharide is also an N- and O-lipoacylated heteropolysaccharide made up of major amounts of D-galactosamine and an aminouronic acid, but in which the O-lipoacyl portion of the lipoheteropolysaccharide contains at least 5 percent by weight (and, more often, between 7 to 14 percent by weight and occasionally as high as 19 percent by weight) of various fatty acid esters in which (a) the fatty acids contain from about 10 to about 18 carbon atoms which are usually distributed in different ratios than those in the low-ester protoemulsans; and (b) more than 50 percent by weight or more of such fatty acids are composed of 2-hydroxydodecanoic acid and 3-hydroxydodecanoic acid;

Thirdly, that α-emulsans rather than β-emulsans may also be produced by growing Acinetobacter Sp. ATCC 31012 on fermentation media containing one or more fatty acid salts as the primary assimilable carbon source;

Fourthly, that α-emulsans are much more effective than β-emulsans in the emulsification of various crude oils and gas-oils and, in some instances (such as the emulsification of Bunker C fuel oil), efficiently form stable emulsions where β-emulsans have no effect;

Fifthly, that both β-emulsans and β-emulsans exhibit specificity in the emulsification of various types of hydrocarbons;

Sixthly, that upon deproteinization of the emulsans all of the emulsifying activity is in the respective N- and O-lipoacyl heteropolysaccharides (which we have herein generically called "apoemulsans" specifically called "apo-α-emulsan" or "apo-β-emulsan" depending upon the particular emulsan from which such deproteinized derivative was formed);

Seventhly, that base hydrolyses of α-emulsan and β-emulsan under mild conditions yield a common derivative (which we have herein called "Ψ-emulsans" and given the common name "pseudoemulsans") which retains about 50 percent of the emulsifying activity of the α-emulsans, the structure of which Ψ-emulsans is the N-acylated poly[D-galactosamine/aminouronic acid] in which (a) the amount of fatty acid esters is between 0 and 1 percent by weight of the polysaccharide; and (b) part of the N-acyl groups are 3-hydroxydodecanoyl groups;

Eighthly, that base hydrolyses of α-emulsan and β-emulsan under strong conditions yield a derivative (which we have herein called "proemulsans") which has no emulsiflying activity and which is structurally a partially N-acylated poly[D-galactosamine/aminouronic acid];

Ninthly, that antibodies prepared against β-emulsan cross-react in an identical fashion with α-emulsan, apo-α-emulsan, apo-β-emulsan, Ψ-emulsan and proemulsan, indicating that the emulsans and their deproteinized and partially deacylated derivatives have approximately the same polymer backbones, which are poly[D-galactosamine/aminouronic acid] polymers;

Tenthly, that the emulsans and their respective deproteinized derivatives are not affected by high concentrations of sodium chloride but require small amounts (from 1 to 100 mM and preferably from 5 to 40 mM) of at least one divalent cation, such as magnesium, calcium or manganese, to function effectively as emulsifying agents for hydrocarbon substrates, which divalent cations are present in sea water, connate water and most "hard" water but must be added to "soft" water;

Eleventhly, that the emulsans on a weight-for-weight basis are probably the most efficient oil-in-water emulsifiers discovered and, moreover, possess certain characteristics that permit these unique extracellular microbial polysaccharides to be widely used in cleaning oil-contaminated vessels, oil spill management, and enhanced oil recovery by chemical flooding; and Finally, that the emulsans and their deproteinized and deacylated derivatives are strongly adsorbed onto aluminosilicate ion-exchanges and are unusually efficient bioflocculents which may be used to mediate flocculation of various types of aluminosilicate clays, such as kaolin and bentonite.

Based on some of these discoveries, the invention provides a process for producing extracellular microbial lipopolysaccharides which comprises (A) inoculating an aqueous fermentation medium containing a growth-sustaining amount of one or more fatty acids with a culture of Acinetobacter Sp. ATCC 31012 or its mutants; and (B) aerobically growing the microorganism in such fermentation medium, while adding additional amounts of such fatty acid salt or salts to sustain growth, for a period of time sufficient to produce extracellular microbial protein-associated lipopolysaccharides (herein collectively called "α-emulsans") in which the lipopolysaccharide components (herein collectively called "apo-α-emulsans") of such α-emulsans are completely N-acylated and partially O-acylated heteropolysaccharides made up of major amounts of D-galactosamine and an aminouronic acid, such as apo-α-emulsans containing at least 5 percent or above by weight O-substituted fatty acid esters in which (1) the fa acids contain from about 10 to about 18 carbon ato1 and (2) about 50 percent by weight or more of such fa acids are composed of 2-hydroxydodecanoic acid a 3-hydroxydodecanoic acid.

The process of the invention further provides th cell-free emulsifying agents comprising an aqueous lution in sea water or fresh water containing from ab 10 mcg/ml to about 20 mg/ml of such α-emulsans, a from about 1 to about 100 mM of at least one dival cation. Using the data contained herein, these emulsi ing agents produced by the process of the invent may be used, among other things, (1) for cleaning 1 drocarbonaceous residues, including residual pet leum, from tankers, barges, storage tanks, tank cars a trucks, pipelines and other containers; (2) for clean oil spills which are floating on the sea or which ha been washed ashore or which are deposited on land; a (3) for the enhanced recovery of oil by chemical flo ing techniques, particularly with respect to those pet leum reservoirs located in sand or sandstone or lir stone formations.

4. NOMENCLATURE

A new lexicon has been used herein to identify a refer to the various types of extracellullar microl polysaccharides and their semi-synthetic derivati which are derived from Actinetobacter Sp. AT 31012 and its mutants. These new words are "em sans", "α-emulsans", "β-emulsans", "Ψ-emulsar "apoemulsans", "apo-α-emulsans, "apo-β-emulsar "apo-Ψ-emulsans" and "proemulsans", which are fined as follows:

The name "emulsans", which reflects the polysacc ride structure of these compounds and the exceptic emulsifying activity of the biologically produced ma rials, has been created to identify generically those tracellular microbial protein-associated lipoheteropc saccharides produced by Acinetobacter Sp. AT 31012 and its mutants, which may be subdivided i the α-emulsans and the β-emulsans. The name "a emulsans", the prefix of which is derived from Greek word meaning "from", has been created to ic tify generically those deproteinized lipopolysacchari obtained from the emulsans.

The name "α-emulsans" defines those extracellı microbial protein-associated lipopolysaccharides ɩ duced by Acinetobacter Sp. ATCC 31012 and its 1 tants in which the lipoploysaccharide components, ( without the associated protein) are completely acylated and partially O-acylated heteropolysacc rides made up of major amounts of D-galactosan and an aminouronic acid, the lipopolysaccharide c ponents containing at least 5 percent by weight of f: acid esters in which (1) the fatty acids contain fi about 10 to about 18 carbon atoms; and (2) abou1 percent by weight or more of such fatty acids are c posed of 2-hydroxydodecanoic acid and 3-hydı ydodeconoic acid. It follows, therefore, that the proteinized α-emulsans The name "Ψ-emulsan" defines the O-deacyl: extracellular protein-associated microbial polysac rides obtained from the emulsans, the protein-free c ponents of such Ψ-emulsans being completely acylated heteropolysaccharides made up of m amounts of D-galactosamine and an aminouronic and containing from 0 to 1 percent of fatty acid este which, when present, the fatty acids contain from about [...] to about 18 carbon atoms. These protein-free compositions are named "apo-Ψ-emulsans", regardless of how they are prepared.

The name "proemulsans" defines the deproteinized deacylated extracellular microbial polysaccharides in which the poly[D-galactosamine/aminouronic acid] polymers are characterized by (1) none of the hydroxy groups being acylated; and (2) from none to all of the amino groups being acylated. The proemulsans have no emulsifying activity under the standard assay techniques described below.

From the data described herein, it is now known that bioemulsifiers which were inherently formed in the experimental work previously published concerning the growth of RAG-1 on crude oil or hexadecane were emulsans in which the lipopolysaccharide contained about 2 to 3 percent by weight of fatty acid esters. The emulsans, therefore, have been given the common name "proemulsans", the prefix of which is derived from the Greek word meaning "first".

The α-emulsans have been given the common name "emulsans", the prefix being derived from the Greek word προτο meaning "new". Because the Ψ-emulsans have only about one-half the emulsifying activity of the α-emulsans, the Ψ-emulsans have been given the common name "pseudoemulsans".

As used herein, the term "Acinetobacter Sp. ATCC 31012 or its mutants" refers not only to the organism (strain RAG-1) described below in Section 6.1 and to its spontaneous and chemically- and physically-induced mutants and recominants which produce emulsans, but to all microorganisms (whatever the genus) derived by using recombinant DNA techniques to insert genetic information from strain RAG-1 and such mutants which are responsible for the production of the emulsifiers into the DNA-based genetic code of such "recombined" microorganisms such that they are capable of biosynthesizing α-emulsans or β-emulsans (or the proemulsans), depending upon the primary assimilable carbon source and the conditions used to grow the organism.

BRIEF DESCRIPTION OF THE DRAWINGS

To more fully comprehend the invention, reference should be made to the accompanying drawings, in which

FIGS. 6A and 6B, is a graphical representation of the kinetics of the emulsan-induced emulsification of gas-oil, showing the relationship between the emulsification of varying concentrations of gas-oil as a function of time for a given concentration of the bioemulsifier;

FIGS. 10A and 10B, is a graphical representation of the relative stabilities of emulsan-induced emulsions of gas-oil, showing the relationship between percentage change in emulsification as a function of standing time of the emulsion for a given concentration of bioemulsifier and varying weight ratios of gas-oil /bioemulsifier;

6. PRODUCTION OF α-EMULSANS AND APO-α-EMULSANS

Figure 1:
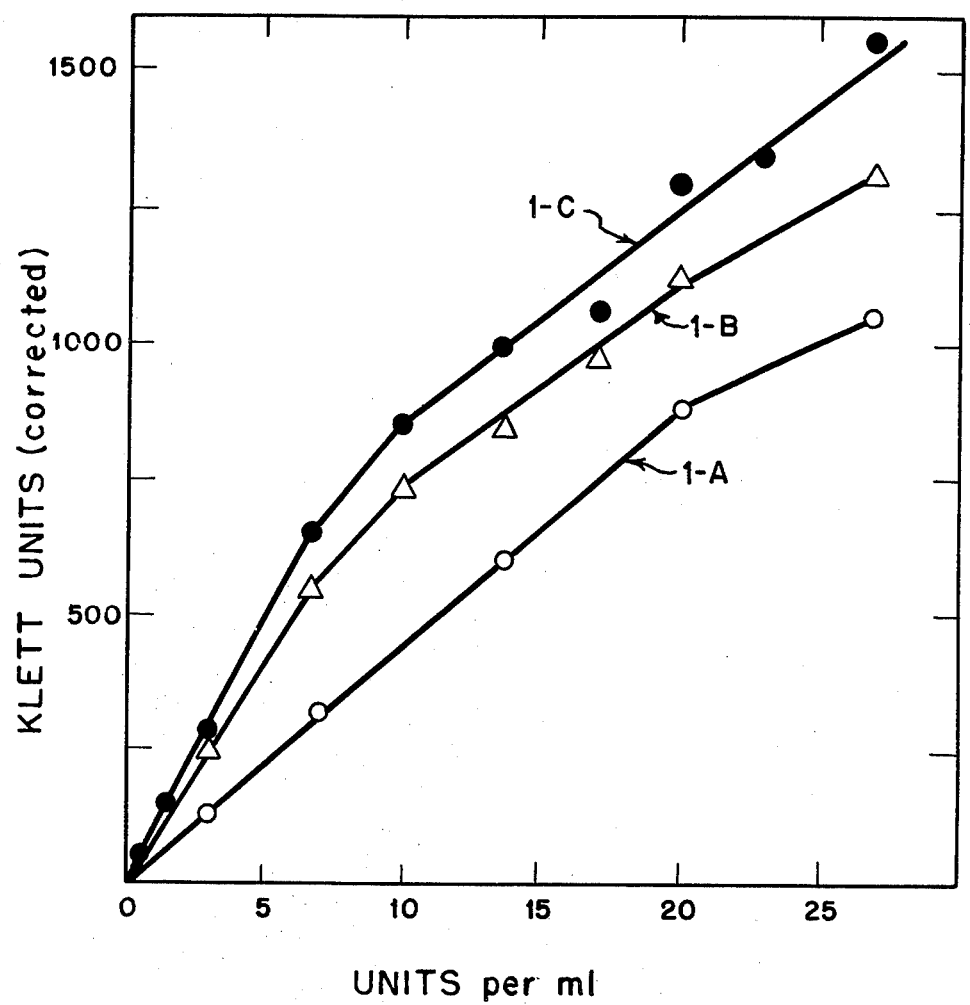
FIG. 1 is a graphical representation of the standard emulsifier assay described below in Section 6.4.1, showing the relationship between the amount of emulsification which is obtained with gas-oil and with a 1:1 (v/v) mixture of hexadecane/2-methylnaphthalene as a function of the emulsan concentration.

α-Emulsans may be produced by aerobically growing Acinetobacter Sp. ATCC 31012 or its mutants on an aqueous fermentation medium which contains (a) a growth-sustaining amount of a utilizable carbon source on which the organism will not only grow but will also produce the desired high-ester α-emulsan rather than the low-ester β-emulsan; (b) greater than growth-sustaining amounts of at least one assimilable nitrogen-containing compound and growth-sustaining amounts of at least one assimilated phosphorous-containing compound to furnish these essential nutrients to the organism; and (c) from about 1 to about 100 mM of a divalent cation, such as magnesium, calcium or manganese, which must be added to the fermentation medium if not present. Apo-α-emulsans, in turn, are produced by deproteinization of the α-emulsans in such manner that the lipoheteropolysaccharide does not undergo degradation.

The fermentation process may be conducted with automatic or manual control in batch or continuous fermenters, using either fresh water or sea water media. Selection of suitable fermentation equipment may be made from designs engineered to give the most efficient oxygen transfer to the biomass at lowest operating cost. In addition to the stirred tank fermenters, other types of fermenters may be used, such as thin channel fermenters, tubular loop fermenters, film fermenters, recirculating tower fermenters, deep shaft fermenters, and jet fermenters, the most important criteria being efficiency in the fermentation process, especially with respect to oxygen transfer and power consumption.

Some of the more important process parameters for the production and purification of α-emulsans and apo-α-emulsans are discussed in more detail below.

6.1. ACINETOBACTER SP. ATCC 31012

The microorganism used to produce both neoemulsans and protoemulsans from utilizable carbon sources is Acinetobacter Sp. ATCC 31012 (also known as strain RAG-1), which has been deposited previously with the American Type Culture Collection, Rockville, Maryland. This organism, which has been described by A. Reisfeld et al., Appl. Microbiol., 24, 363 (1972) as well as by U.S. Pat. No. 3,941,692, has the following characteristics:

During the exponential growth phase the cells appear mostly as irregular short rods, 0.9 to 1.2 by 1.5 to 3.0 mcm (mcm = $10^{-6}$ m). The cells occur often as V-shaped pairs, indicating snapping division. Occasionally, the rods are slightly bent or swollen. Coccoid cells, approximately 1.2 mcm in diameter, are characteristic of stationary phase cultures. The cocci are gram-positive; the rods are gram-negative.

Agar colonies: circular, glistening and smooth, up 5.0 mm in diameter; gelatin is liquified; starch is n hydrolyzed; indole and hydrogen peroxide are not pr duced; nitrites are produced from nitrate only when tl cells are grown in citrate medium containing potassiu nitrate; urease is not produced; catalase-positive; aer bic; hemolysis of rabbit blood agar; citrate can serve the sole carbon and energy source; no acid from gl cose, cellulose, maltose, lactose, rhamnose, sucrose mannitol; optimum temperature 30° to 35° C.

The amount of inoculum used to initiate the ferment tion will be dependent upon the type of fermentatic equipment used.. For optimum results in batch-ty] stirred fermenters, growth should be initiated with la exponential cultures grown under similar fermentatic conditions, preferably in an amount from about 1% about 5% (v/v) of the fermentation medium.

6.2. FERMENTATION MEDIA

6.2.1. UTILIZABLE CARBON SOURCES

Even though it has previously been reported by Horowitz et al., Appl. Microbiol, 30, 10 (1975), th strain RAG-1 will grow on many different carbon cor pounds on sea water agar media supplemented with t carbon source, such growth has no relationship wi whether or not the organism will produce any type Acinetobacter bioemulsifier (which, when produce usually occurs during the exponential growth phas much less the high-ester α-emulsans. Moreover, even those instances where the organism does produce extr cellular lipopolysacchrides, there does not appear to any correlation between the structure of the utilizat carbon source and what type of extracellular lipopol saccharide will be biosynthesized from such carb source, whether the high-ester α-emulsans or the lo ester β-emulsans. For example, growth of Acinetoba ter Sp. ATCC 31012 on ethanol, sodium palmitate dodecane results in the formation of α-emulsans wi each such carbon source, with ethanol media yieldi: α-emulsans with the highest ester content in the lipc cyl portion of the lipoheteropolysaccharide, wh growth of the organism under substantially identic conditions using pentadecane, hexadecane or heptade ane results only in the formation of β-emulsans. In ge eral, where a utilizable carbon source can be tra1 formed into α-emulsans by the organism, the total yie of the extracellular lipopolysaccharide per liter of c ture medium will be greater than when the organi: produces β-emulsans from a different carbon source In the present invention, α-emulsans are produced growing Acinetobacter Sp. ATCC 31012 or its muta1 on an aqueous fermentation medium in which one more fatty acid salts are the primary assimilable carb source. Such fatty acids salts include the assimilal saturated fatty acids, such as decanoic acid (cap acid), dodecanoic acid (lauric acid), tetradecanoic a1 (myristic acid), hexadecanoic acid (palmitic acid) a octadecanoic acid (stearic acid); unsaturated $C_{10}$ to ( fatty acids, including monoethenoid and diethen1 fatty acids; hydroxysubstituted fatty acids, such as hydroxydodecanoic acid, 3-hydroxydodecanoic a1 and 12-hydroxyoleic acid (ricinoleic acid). In additi1 mixtures of fatty acids may be used, such as the mi} fatty acids derived from saponification of lard, soybe oil, peanut oil, cottonseed oil, sunflower oil, coco1 oil, castor oil, palm oil, linseed oil, and various fish ( or marine mammal oils.

Emulsans produced by aerobically growing [Acin]etobacter Sp. ATCC 31012 on media containing [fatty] acid salts are unusually efficient bioemulsifiers, [exhib]iting a high degree of specificity in emulsifying [those] hydrocarbon substrates (such as crude oils, gas[oline] and Bunker C fuel oils) that contain both aliphatic [and] aromatic or cyclic components. For optimum re[sults] in batch-type stirred fermenters, the initial media [shou]ld contain from about 1% to about 5% by weight [of on]e or more fatty acid salts, with make-up fatty acid [and/]or salts added during the fermentation at a rate [suffic]ient to sustain maximum growth and α-emulsan [prod]uction, since the production of α-emulsans by the [orga]nism has been found to occur during the growth [phase.]

6.2.2. ADDITIONAL NUTRIENTS

[Ma]ximum growth of Acinetobacter Sp. ATCC 31012 [on a] utilizable carbon source to produce α-emulsans [requi]res more than growth-sustaining amounts of one or [more] assimilable nitrogen-containing compounds to [furni]sh this essential nutrient to the organism to enable [the o]rganism to grow and to produce the biopolymer, [whic]h contains major amounts of amino sugars. Addi[tiona]lly, phosphorus-containing compounds are also [essen]tial nutrients.

[Su]itable source of available nitrogen include ammo[nium] salts, such as ammonium sulfate or ammonium [chlor]ide; nitrates, such as ammonium nitrate or sodium [nitra]te; or organic sources of available nitrogen, such as [urea] or soybean meal. Suitable sources of available [phos]phorous include dibasic potassium phosphate, [mono]basic potassium phosphate and the like. In addi[tion,] liquid fertilizers, such as 12-6-6 or 8-8-8, may serve [as a] source of nitrogen and phosphorous nutrients for [the g]rowth of Acinetobacter Sp. ATCC 31012.

6.2.3. DIVALENT CATIONS

[As] shown below in the data set forth in Section 8.4, [the e]mulsifying activity of both types of Acinetobacter [bioem]ulsifiers is dependent above pH 6 upon divalent [catio]ns, such as magnesium ions, calcium ions or manga[nese] ions. These divalent cations are present in sea [wate]r or "hard" water when fermentation media are [prep]ared from such sources. When "soft" fresh water or [distil]led water are used to prepare the fermentation [medi]a, then small amounts of one or more salts of a [divale]nt cation should be added to the fermentation [medi]a, the concentration being such that the resultant [mixtu]re media will contain from about 1 to about 100 (and preferably from about 5 to about 40 mM) of at [least] one divalent cation.

FERMENTATION PROCESS CONDITIONS

[Ma]ximum growth of Acinetobacter Sp. ATCC 31012 [on a] utilizable fatty acid carbon sources to produce [α-em]ulsans requires selection of the best conditions of [aerat]ion, agitation, temperature and pH under which [the h]ighest possible oxygen transfer can be obtained [cons]istent with the physiology of the organism. Dis[cusse]d below are the best conditions which have been [foun]d for consistently producing high yields of emul[sans] from sodium palmitate media in conventional 60-[liter] stirred fermenters. These conditions probably will [unde]rgo subtle or pronounced changes to obtain higher [yield]s upon large-scale production in fermenters specifi[cally] designed or adapted to give more efficient oxygen [trans]fer at the lowest power consumption. Subsequent work on optimizing the process will, of course, focus on (a) consumption of the substrate, which is a fucntion of the physiology of Acinetobacter Sp. ATCC 31012 and its mutants; (b) consumption of oxygen, which is a function of oxygen diffusion to the cells which, in turn, will be influenced (i) by making the surface through which the diffusion occurs as large as possible (i.e., dispersing the gas phase as finely as possible in the liquid phase to create a large gas hold-up), (ii) by increasing the driving force of the diffusion (such as by increasing the pressure in the fermenter or by using oxygen-enriched air), and (iii) by allowing the diffusion constant to be as high as possible (i.e., by minimally decreasing the diffusion constant by the use of chemical antifoam agents); and (c) exothermic heat production, which necessitates a properly designed cooling system on scale-up.

6.3.1. AERATION

Using 60-liter stirred fermenters with the fermentation medium and process conditions described below in Section 13.1, maximum production of α-emulsans occurs when 15 liters of air per minute are passed through the 40 liters of fermentation medium, which corresponds to an oxygen flow rate of 189.6 millimoles per liter per hour. This oxygen flow rate is not limiting but can, if necessary, be increased to as high as 700 millimoles per liter per hour, or even higher, with the more efficiently designed fermenters.

6.3.2. AGITATION

To promote maximum oxygen diffusion to the cell mass, the fermentation media must be agitated either by stirring or circulating the media through the fermenter, depending upon the type of fermentation equipment employed. Using 60-liter stirred fermenters with the fermentation medium and other process conditions described below in Section 13.1, maximum production of α-emulsans occurs when the medium is agitated at a rate of 250 rpm. This value is not limiting but will be varied in the more efficiently designed fermenters to achieve maximum oxygen transfer at the lowest power consumption.

6.3.3. TEMPERATURE AND pH

Although the fermentation process may be conducted over a wide range of temperatures, best results have been obtained in the production of emulsans when the fermentation is conducted at 30° C. The pH of the fermentation medium should be maintained between 6 and 7, and preferably between 6.2 and 6.7 during the exponential growth phase, which necessitates the addition of sufficient base (preferably ammonia).

6.3.4. DEFOAMING

Stirred-tank fermentations of Acinetobacter Sp. ATCC 31012 on utilizable fatty acid carbon sources to produce α-emulsans invariably are accompanied by foaming problems, which diminish the realizable yield of the extracellular lipopolysaccharide. Although many types of chemical defoamers may be used in the fermentation media, great care must be taken when adding chemical defoaming agents to keep the diffusion constant as high as possible. Using the 60-liter stirred fermenters with the fermentation medium and other process conditions described below in Section 13.1, maximum production of α-emulsans occurs when there are automatic pulse additions (whenever foam levels reached a predetermined height) of a silicone defoamant, preferably Dow-Corning 525 (sterilizable), diluted 1:8. Upon scale-up of the fermentation process, it is expected that a combination of chemical and mechanical methods will give optimum results in defoaming the nutrient solutions on which α-emulsans will be produced from Acinetobacter Sp. ATCC 31012 and its mutants.

6.4. EXTRACELLULAR PRODUCTION OF EMULSANS

Data is presented below with respect to both types of extracellular lipopolysaccharides (α-emulsans and β-emulsans) produced by Acinetobacter Sp. ATCC 31012 so that the similarities as well as differences between these biopolymers may be understood. Unless the particular type of extracellular lipopolysaccharide produced by the organism is identified by name, the phrase "Acinetobacter bioemulsifier" refers collectively to both α-emulsans and β-emulsans.

6.4.1. STANDARD ASSAY FOR EMULSIFYING ACTIVITY

In order to study the kinetics of bioemulsifier production by Acinetobacter Sp. ATCC 31012 and to compare the emulsifying activities of α-emulsans and β-emulsans, a series of simple sensitive assays for these bioemulsifiers were developed. These assays were based upon the large increase in turbidity of a mixture of oil and water arising from the emulsion of the hydrocarbon in the aqueous phase.

The first assay involved the emulsification of gas-oil in sea water under standardized conditions and subsequent measurement of turbidity. When it was found that sea water could be replaced in the assay procedure with dilute solutions of magnesium salts (cf/ Section 8.4), a second assay was developed involving emulsification of gas-oil in 10 mM of magnesium sulfate at pH 7.2. Finally, after it was found that the bioemulsifiers exhibited a degree of specificity toward different classes of hydrocarbon substrates (cf/ Section 9), totally defined conditions were developed using a mixture of hexadecane and 2-methylnaphthalene in place of gas-oil and buffered magnesium sulfate (or magnesium chloride) in place of sea water.

Each assay technique consisted of adding hydrocarbon (0.05 ml of gas-oil or 0.1 ml of 1:1 (v/v) hexadecane/2-methylnaphthalene) to 7.5 ml of filtered sea water or 7.5 ml of Tris-Mg buffer [20 mM tris-(hydroxymethyl)aminomethane hydrochloride, pH 7.2, supplemented with 10 mM magnesium sulfate] containing 1 to 25 units of bioemulsifier per ml (about 3 to 75 mcg/ml of bioemulsifier) in a 125 ml flask. After reciprocal shaking (150 strokes per minute) for one hour at 26° C., contents of the flask were transferred to Klett tubes for measurement of turbidity in a Klett-Summerson colorimeter fitted with a green filter. Appropriate dilutions were made in water so that the final readings were between 30 and 150 Klett units, and values for Klett units reported as final readings times the dilution. Values for controls containing no bioemulsifier (5 to 20 Klett units) were subtracted. One unit of bioemulsifier per ml is defined as that amount of activity which yields 100 Klett units using 0.1 ml of 1:1 (v/v) hexadecane/2-methylnaphthalene and 7.5 ml of Tris-Mg buffer. Specific Emulsification Activity (or specific activity) is units per mg of bioemulsifier, dry weight basis.

FIG. 1 graphically illustrates standard curves obtained when all three assay techniques were applied to an α-emulsan produced by growing Acinetobacter S ATCC 31012 at 30° C. in a reciprocally shaken flask c a medium containing 1.0% (v/v) ethanol, 0.125% ure 0.125% magnesium sulfate [$MgSO_4.7H_2O$], 0.0002 ferrous sulfate [$FeSO_4.7H_2O$], 0.001% calcium chloric (anhyd), 0.025% dibasic potassium phosphate, and 0 M Tris HCl buffer, pH 7.4. The preparation of α-emu san used in preparing such curves had a Specific Emu sification Activity of 330 units per mg. Curve 1-A repr sents the relationship between the amount of emulsific tion between 0.05 ml Gach-Saran gas-oil and 7.5 ml filtered sea water; Curve 1-B represents the relationsh between the amount of emulsification between 0.05 r Gach-Saran gas-oil and 7.5 ml Tris-Mg buffer; ar Curve 1-C represents the relationship between tl amount of emulsification between 0.1 ml 1:1 (v/v) he adecane/2-methylnaphthalene and 7.5 ml Tris-M buffer, all as a function of α-emulsan concentratio Each point in FIG. 1 represents the average of 3 to determinations. These standard curves were then us( to determine the emulsifying activity of preparations crude and purified emulsans (α-emulsan, β-emulsan ar the semi-synthetic Ψ-emulsan) and apoemulsans (apo-ι emulsan, apo-β-emulsan and apo-Ψ-emulsan). Chara terization of a particular Acinetobacter bioemulsifier an α-emulsan or a β-emulsan is based on chemical anε ysis of the fatty acid esters contained in the lipoac portions of the protein-extracted lipopolysaccharides

6.4.2. EXTRACELLULAR PRODUCTION OF α-EMULSANS

Measurement of extracellular emulsifying activi was determined at different stages of growth Acinetobacter Sp. ATCC 31012 in an ethanol mediui the fermentation conditions being identical to tho used to prepare the α-emulsan used for the standa assay tests. Growth was estimated by turbidity using Klett-Summerson colorimeter fitted with a green filt or a Gilford Spectrophotometer (Model 240). One hu dred Klett units of exponentially growing Acinetoba ter Sp. ATCC 31012 correspond to an absorbance 620 nm (1-cm light path) of 0.816 and a biomass of 0. g per liter (dried at 90° C. for 16 hours).

Figure 2:
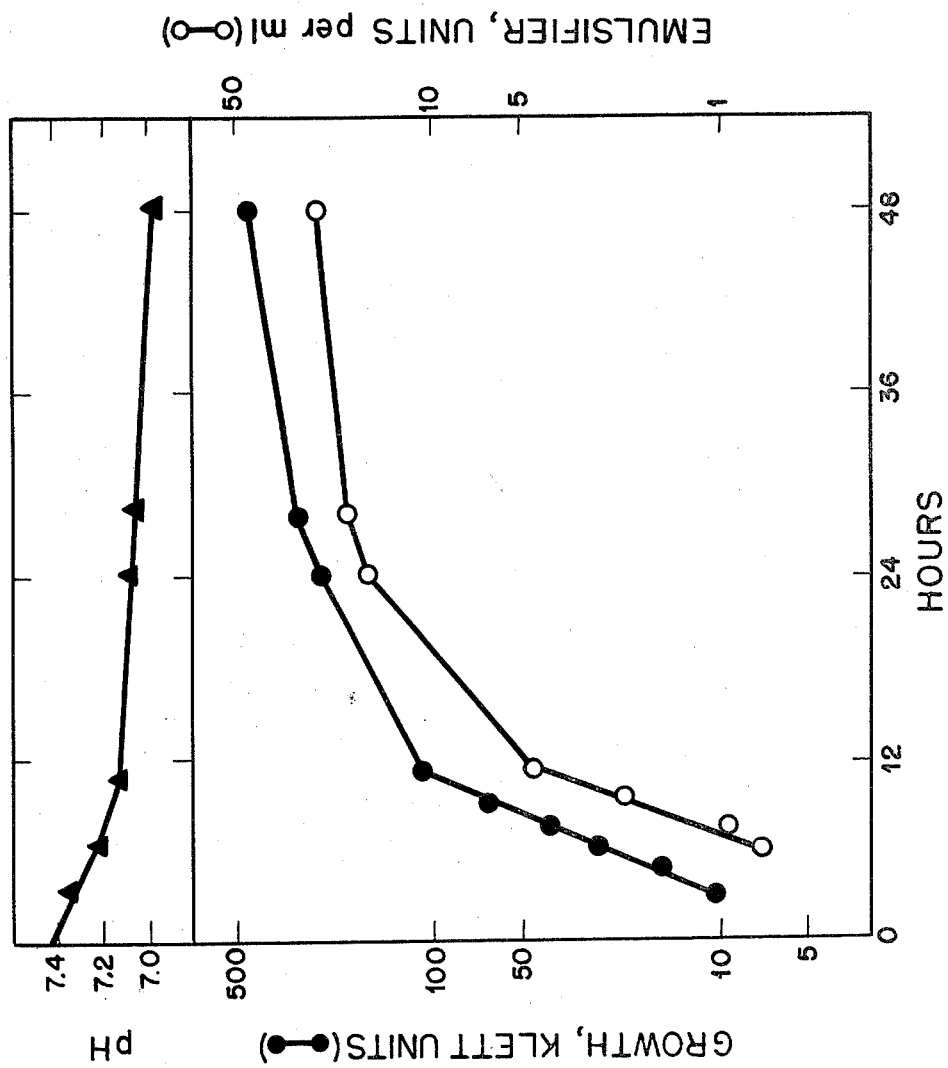
FIG. 2 is a graphical representation of the extracellular production of α-emulsan during growth of Acinetobacter Sp. ATCC 31012 on an ethanol medium, showing the relationship of the growth of the organism in such medium, the production of the bioemulsifier during such growth, and the change of pH during such growth, all as a function of time.

FIG. 2 shows the relationship between the growth Acinetobacter Sp. ATCC 31012 on the ethanol π dium, the production of the bioemulsifier (α-emulsa during such growth, and the change of pH during su growth, all as a function of time. Although these dε are limited to the production of α-emulsan in a shaki flask fermentation with a particular ethanol mediu FIG. 2 illustrates the general rule that the production α-emulsan occurs during the growth period. Simi data have been obtained on the growth of Acinetobε ter Sp. ATCC 31012 on a sodium palmitate medium

6.4.3. EXTRACELLULAR PRODUCTION OF β-EMULSANS

Measurement of extracellular emulsifying activ was also determined at different stages of growth Acinetobacter Sp. ATCC 31012 in a hexadecane n dium, the medium and fermentation conditions bei identical to those used to prepare the β-emulsan us for the standard assay tests except that 0.2% (v/v) he: decane medium was used in place of ethanol as t carbon source. Viable cell number was determined spreading 0.1 ml of an appropriate dilution on AC agar, which contained 0.5% sodium acetate, 0.1% ye extract (Difco), 0.125% urea, 0.025% dibasic potassii phate and 1.5% agar (Difco). Plates were incubated at 32° C. for 3 days.

Figure 3:
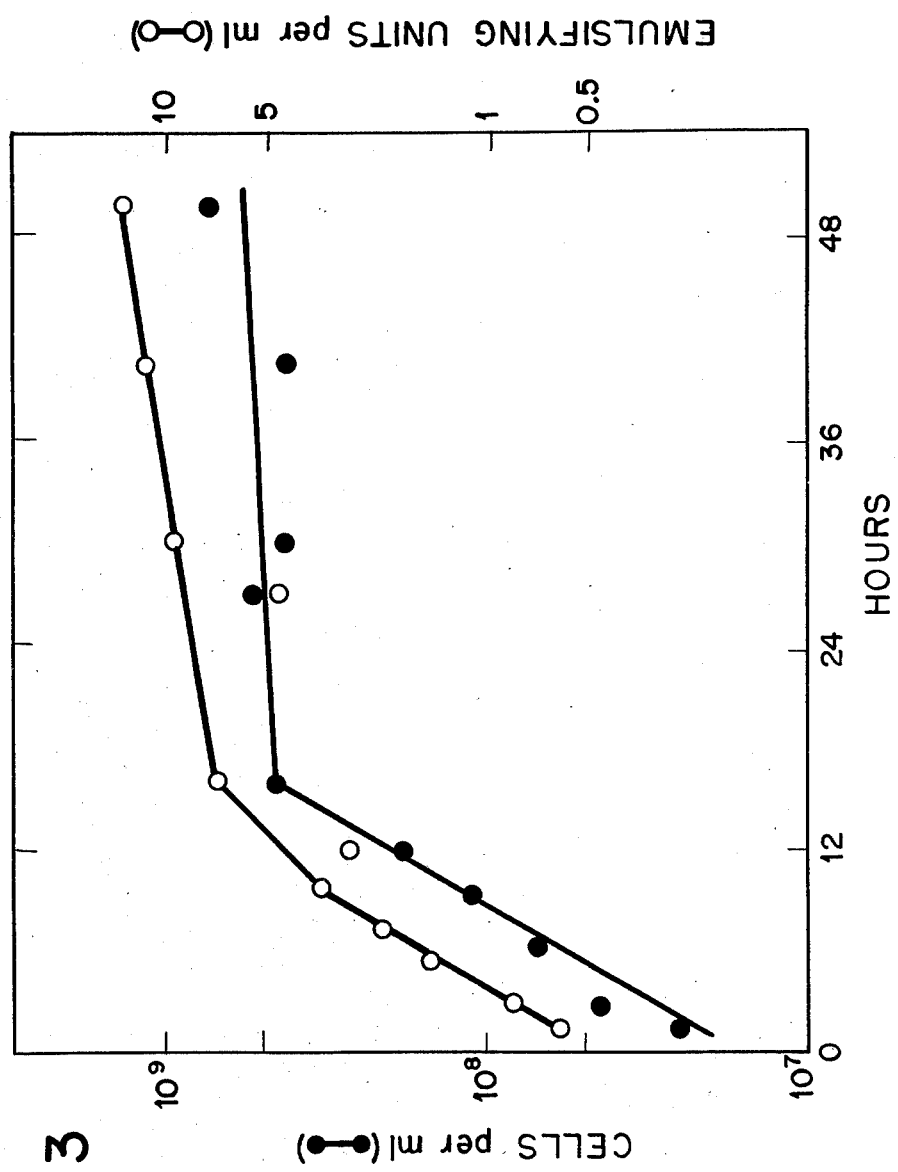
FIG. 3 is a graphical representation of the extracellular production of β-emulsan during growth of Acinetobacter Sp. ATCC 31012 on a hexadecane medium, showing the relationship of the growth of the organism in such medium and the production of the bioemulsifier during such growth, both as a function of time.

FIG. 3 shows the relationship between the growth of Acinetobacter Sp. ATCC 31012 on the hexadecane medium and the production of the bioemulsifier (β-emulsan) during such growth. The data contained in FIG. 3 is similarly limited to the production of β-emulsan in a shaking flask fermentation with a particular hexadecane medium, and shows that the production of β-emulsan also occurs during the growth period.

6.4.4. DISTRIBUTION OF EMULSIFYING ACTIVITY IN FRACTIONS OF GROWTH CULTURE

After 40 hours of incubation of Acinetobacter Sp. ATCC 31012 in the ethanol medium and in the hexadecane medium as described above in Sections 6.3.2 and 6.3.3 respectively, each culture was centrifuged at 10,000×g for 15 minutes and the pellets washed once in Tris-Mg buffer. The pellicle formed during centrifugation of the hexadecane culture was removed, washed twice with growth medium before assaying for activity. Emulsifying activity in each fraction for the ethanol and hexadecane growth cultures was assayed by the standard assay technique described above in Section 6.4.1 and illustrated in FIG. 1. The results of these assays are summarized in Table I.

TABLE I
Distribution of Emulsifying Activity in Fractions of Growth Cultures

| Fraction | Emulsifier (units/ml) | |
|---|---|---|
| | Ethanol Substrate | Hexadecane Substrate |
| Pellet | 7 | 0 |
| Supernatant fluid | 23 | 14 |
| Pellicle | — | 0 |

The data contained in Table I show that over 75% of activity was extracellular when ethanol was the substrate, while all of the measureable activity was extracellular when Acinetobacter Sp. ATCC 31012 was grown on hexadecane medium. The small amount of activity associated with the pellet fraction was variable; in certain cases no measureable cell-bound activity could be found. Disruption of the pellet fractions by sonic oscillation did not release additional emulsifying activity.

6.5. DEPROTEINIZATION

Apoemulsans may be prepared by deproteinization of the particular emulsans, which technique was used to isolate and purify samples for the chemical characterization of both Acinetobacter bioemulsifiers described below. The associated protein may be separated from the bioemulsifiers by the hot phenol extraction technique described by O. Westphal et al. in the monograph edited by R. L. Whistler, entitled "Carbohydrate Chemistry", Academic Press, Inc., New York, pp. 91. Alternatively, the protein may be removed enzymatically by proteolytic digestion.

6.6. ISOLATION AND PURIFICATION

The extracellular protein-associated lipopolysaccharides produced by Acinetobacter Sp. ATCC 31012 and their respective deproteinized derivatives may be isolated and purified by various procedures, including selective precipitation, selective solvent extraction or partitioning or selective adsorption onto a solid adsorbant followed by subsequent elution or extraction. For many industrial uses, isolation and purification of the Acinetobacter bioemulsifiers is not necessary, since the cell-free growth media may be used directly. For the purposes of determining their respective structures as well as their chemical and physical properties, particularly with respect to emulsifying activity, the α-emulsans and β-emulsans produced by Acinetobacter Sp. ATCC 31012 have been isolated and purified. Three different procedures have been followed, including (a) heptane partitioning of the crude extracellular lipopolysaccharide from the fermentation medium, followed by extraction of impurities from the heptane-partitioned biopolymer and subsequent work-up; (b) precipitation of the extracellular lipopolysaccharide by ammonium sulfate, followed by work-up of the precipitate; and (c) precipitation of the extracellular lipopolysaccharide by a detergent quaternary ammonium cation followed by work-up of the precipitate. Each of those techniques is equally applicable to the isolation and purification of the apo-α-emulsans and the apo-β-emulsans.

6.6.1. HEPTANE PARTITIONING

Because the Acinetobacter bioemulsifiers exhibit specificity with respect to the structurally different types of hydrocarbon substrates which may be emulsified (cf/ Section 9), certain water-immiscible hydrocarbons may be used to selectively extract the extracellular lipopolysaccharide from the fermentation media without creating a stable emulsion. By way of illustration, heptane extraction of the cell-free culture medium from which ether-extractibles had been removed suspended over 90% of extracellular lipopolysaccharide at the heptane/water interface. After evaporation of the heptane, and preferably further solvent extraction with ether, the resultant product is a viscous syrup which can be dissolved in 50% aqueous methanol, the impurities removed by dialysis and the remaining material recovered by lyophilization. In a typical example using this heptane extraction technique, a purified β-emulsan was prepared which was characterized by a specific activity of 205 units per mg.

6.6.2. AMMONIUM SULFATE PRECIPITATION

The addition of ammonium sulfate to the fermentation broth has been used to fractionally precipitate the extracellular lipopolysaccharides from the culture medium, from which the concentrate may be recovered and further treated to remove impurities. By way of illustration, addition of ammonium sulfate to cell-free supernatent fluids has resulted in the precipitation of substantially all of the extracellular lipopolysaccharides when the concentration of ammonium sulfate is increased from 30% saturation to a final concentration of 40% saturation. The resulting precipitate, which may be collected by centrifugation, has been extracted by ether to remove impurities, dialyzed against water and lyophilized, yielding the purified extracellular lipopolysaccharide. In a typical example using this ammonium sulfate precipitation technique, a purified α-emulsan was prepared which was characterized by a specific activity of 330 units per mg.

6.6.3. QUATERNARY AMMONIUM PRECIPITATION

Because the extracellular lipopolysaccharides produced by Acinetobacter Sp. ATCC 31012 were found to be anionic biopolymers, a procedure was developed to precipitate the anionic biopolymer with a cationic detergent, such as cetyltrimethyl ammonium bromide, from which precipitate the detergent cation could be separated while leaving the purified extracellular lipopolysaccharide. For example, the addition of cetyltrimethyl ammonium bromide to an aqueous solution of α-emulsan immediately forms a precipitate which is recoverable by centrifugation or filtration. This precipitate is soluble in 0.1 M sodium sulfate, from which solution cetyltrimethyl ammonium iodide precipitates upon addition of potassium iodide, leaving the α-emulsion in the supernatent fluid. Dialysis of this supernatent fluid against distilled water, followed by lyophilization, has yielded highly purified samples of α-emulsan as a white solid, with a specific activity of 350 units per mg.

7. CHEMICAL AND PHYSICAL PROPERTIES OF EMULSANS AND APOEMULSANS

Chemical and physical characterization of emulsans and apoemulsans were measured on samples which had been purified to apparent homogeneity, from which characterization conclusions were reached on the structure of these unique extracellular lipopolysaccharides. Such information is necessary to give a better understanding of the relationship between the molecular structure of this class of bioemulsifiers and their specificity in emulsifying various hydrocarbon substrates.

7.1. PREPARATION OF SAMPLES FOR ANALYTICAL CHARACTERIZATION

7.1.1. PREPARATION OF EMULSAN SAMPLES

The emulsan samples used for chemical and physical characterization were prepared by aerobically growing acinetobacter Sp. ATCC 31012 on an ethanol medium (α-emulsan) or a hexadecane medium (β-emulsan) and were purified by precipitation between 39–40% ammonium sulfate saturation, followed by extraction with ether, dialysis against distilled water and lyophilization, as described more fully in the example set forth below in Section 13.8. Some samples of α-emulsan were further purified by employing the cetytrimethyl ammonium bromide precipitation technique, as described more fully in the example set forth below in Section 13.11.

7.1.2. PREPARATION OF APOEMULSAN SAMPLES

The apoemulsan samples used for chemical and physical characterization were prepared by hot phenol extraction of the associated protein moiety from the emulsan samples. The deproteinization procedure, which is described more fully in the example set forth below in Sections 13.4 and 13.5, involved adding a dilute solution (5 mg/ml) of emulsan preheated to 65°–68° C. to an equal volume of 90% phenol at 65° C., stirring the mixture for 15 minutes while maintaining the temperature at 65° C., and then cooling the mixture to 10° C. in an ice bath. The resulting emulsion was then centrifuged to separate the denatured protein in the phenol phase from the apoemulsan in the aqueous phase. After transferring the viscous aqueous phase to a flask, the phenol layer and phenol/water interface were extracted three more times with water, following which the combined water extracts were dialyzed extensively against several changes of distilled water and then freeze-dried, yielding 85% by weight of apoemulsan based on the weight of the emulsan. All of the emulsifying activity was in the recovered emulsan. None of the emulsifying activ was in the denatured protein fraction.

7.1.3. AMMONIUM SULFATE FRACTIONATIC OF APO-α-EMULSAN

To assure homogeneity of the apo-α-emulsan, deproteinization procedure was repeated on anotl sample of α-emulsan which had been prepared by ae bically growing Acinetobacter Sp. ATCC 31012 on ethanol medium and which had been purified by prec itation between 30–40% ammonium sulfate fracti( ation, followed by extraction with ether, dialysis agai distilled water and lyophilization. After three phe1 extractions, the combined water extracts were extrac1 four fimes with an equal volume of ether to remc residual phenol. Following evaporation of any retair ether, the viscous aqueous phase was cooled to 5° and brought to 32.5% ammonium sulfate saturati( After standing for one hour at 5° C., the clear trans cent precipitate was collected at centrifugation 5,000×g for 30 minutes at 5° C. The procedure v repeated to obtain a slightly turbid second precipit between 32.5% and 35% ammonium sulfate saturati and another small precipitate between 35% and 4( ammonium sulfate saturation. No additional precipit formed between 40% and 60% saturation.

Each of the precipitates was dissolved in water ε was then dialyzed at 2°–5° C. successively against ( tilled water, 0.05 N hydrochloric acid for 24 hours ε double distilled water, following which each of resulting solutions were freeze-dried. Over 99% of emulsifying activity of the apo-α-emulsan was founc the two fractions which precipitated between 30% ε 35% ammonium sulfate saturation. These two fracti( contained similar specific activities and exhibited s· stantially the same chemical composition. In additi( both fractions were homogeneous when examined immunodiffusion against antibodies prepared agai β-emulsan, each giving a single identical band uf Ouchterlony two-dimensional diffusion. According the two fractions were combined for certain of chemical and physical characterizations, the combir fractions when used being identified herein as "apo emulsan-WA".

7.1.4. QUATERNARY AMMONIUM SALT PERCIPITATION OF APO-α-EMULSAN

To cross-check the analytical data on apo-α-emuls WA, another highly purified sample of apo-α-emul was prepared using (1) the identical hot phenol extr tion of another sample of α-emulsan which had bi prepared by aerobically growing Acinetobacter ATCC 31012 on an ethanol medium, followed by cetyltrimethyl ammonium bromide precipitation of resultant apo-α-emulsan, dissolving the precipitate 0.1 M sodium sulfate, and addition of potassium iod to the solution to precipitate cetyltrimethyl ammoni iodide. The supernatant fluid contained the apo-α-en san. Extensive dialysis of this supernatant fluid aga: distilled water followed by lyophilization yielde( highly purified apo-α-emulsan which was designatec "apo-α-emulsan-CTAB".

7.2. CHEMICAL CHARACTERIZATION

7.2.1. CHEMICAL COMPOSITION OF EMULSANS AND APOEMULSANS lemental analyses of α-emulsan and apo-α-emulsan, ːh were performed on samples of α-emulsan and α-emulsan-WA that had been dried to constant ɟht at 55° C. in vacuo (the latter sample having ised 12.7% water on such drying), are shown in le II.

TABLE II

| | Elemental Composition of Emulsan | | | | |
|---|---|---|---|---|---|
| ıle | % C | % H | % N | % S | % Ash |
| ıulsan | 41.72 | 6.95 | 7.74 | 0.7 | 13.8 |
| α-emulsan-WA | 46.70 | 7.01 | 6.06 | 0.0 | 3.5 | he deproteinized sample (apo-α-emulsan-WA) conːd significantly less N, S and ash than emulsan. The :H ratio of apo-α-emulsan-WA was calculated to be 1.0:16.1. No significant quantities (<0.5%) of phosrus or halides were found in either sample. Funcal group tests were positive for carboxyl and ester ıps and negative for methoxy and ethoxy groups. polymer contained less than 0.02 micromoles reıng sugar per mg, which was the sensitivity of the employed. The nonreducing polymer was resistant ıgh temperatures in neutral and alkaline conditions. emulsifying activity was lost at 100° C. for 2 hours ıstilled water; 50% of the activity remained even r treatment in 1 N sodium hydroxide at 100° C. for our. Apo-α-emulsan-WA was considerably more ıitive to acid, losing 50% of its emulsifying activity minutes at 100° C. in 1 N hydrochloric acid.
itration of apoemulsan-WA (40 mg/4 ml) between 2.5–10.5 showed a single inflection point, correıding to pK' = 3.05 (identical to a standard sample of :uronic acid). Apo-α-emulsan-WA consumed 0.24 romoles periodate per mg (which would suggest the ıence of a small amount of glucose in the polymer), ch was subsequently determined to be due to a small ıunt of glucose present in an ammonium sulfate coːipitated extracellular polysaccharide which posed no emulsifying activity. Periodate uptake ceased r two hours at 30° C., pH 4.5. The periodate treated erial did not lose any emulsifying activity, further cating that no glucose was present in the apo-α-ılsan.

7.2.2. ALKALINE HYDROLYSIS OF APOEMULSAN

`wo hundred milligrams of apo-α-emulsan-WA were uxed in 40 ml of 1 N sodium hydroxide for 4 hours, led, extracted three times with 40 ml ether, acidified ɔH 1–2 with concentrated hydrochloric acid, and ˙acted again three times with 40 ml ether. The acidːr extracts were combined and dried in a tared flask, ding 30 mg (15%) fatty acids; extraction with ether ɔr to acidification yielded less than 2 mg dry mate-. Combining the weight recovery of fatty acid from polymer (150 mcg/mg) and the 0-ester content (0.65 ˙romoles/mg) yields an average equivalent weight of for the fatty acids.

2.3. ACID HYDROLYSIS OF APOEMULSAN

'reliminary hydrolysis studies were performed on ı-α-emulsan at 80° C. and 100° C. in sealed tubes with ıcentrations of hydrochloric acid varying from 0.01–6.0 M. After removal of hydrogen chloride in vacuo, the products were examined for reducing power, amino sugars and by paper chromatography in n-butanol/pyridine/water (6:4:3, v/v) [Solvent A] and in n-propanol/ethyl acetate/water (7:1:2, v/v) [Solvent B].

Figure 4:
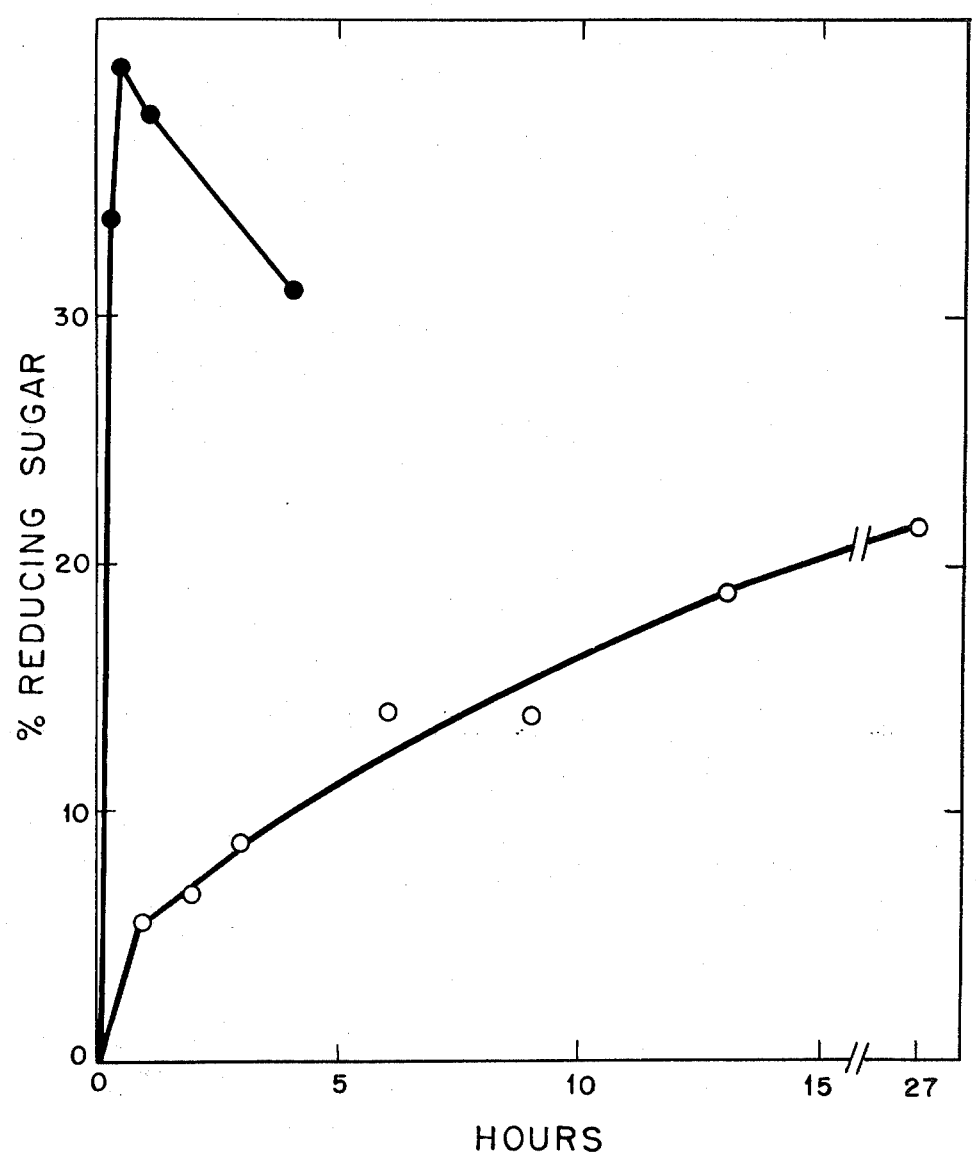
FIG. 4 is a graphical representation of the changes which occur on acid hydrolysis of apo-α-emulsan, showing the relationship between the weight percent of reducing power of the acid-hydrolyzed deproteinized O-lipoacylated heteropolysaccharide as a function of the duration of hydrolysis.
Figure 5:
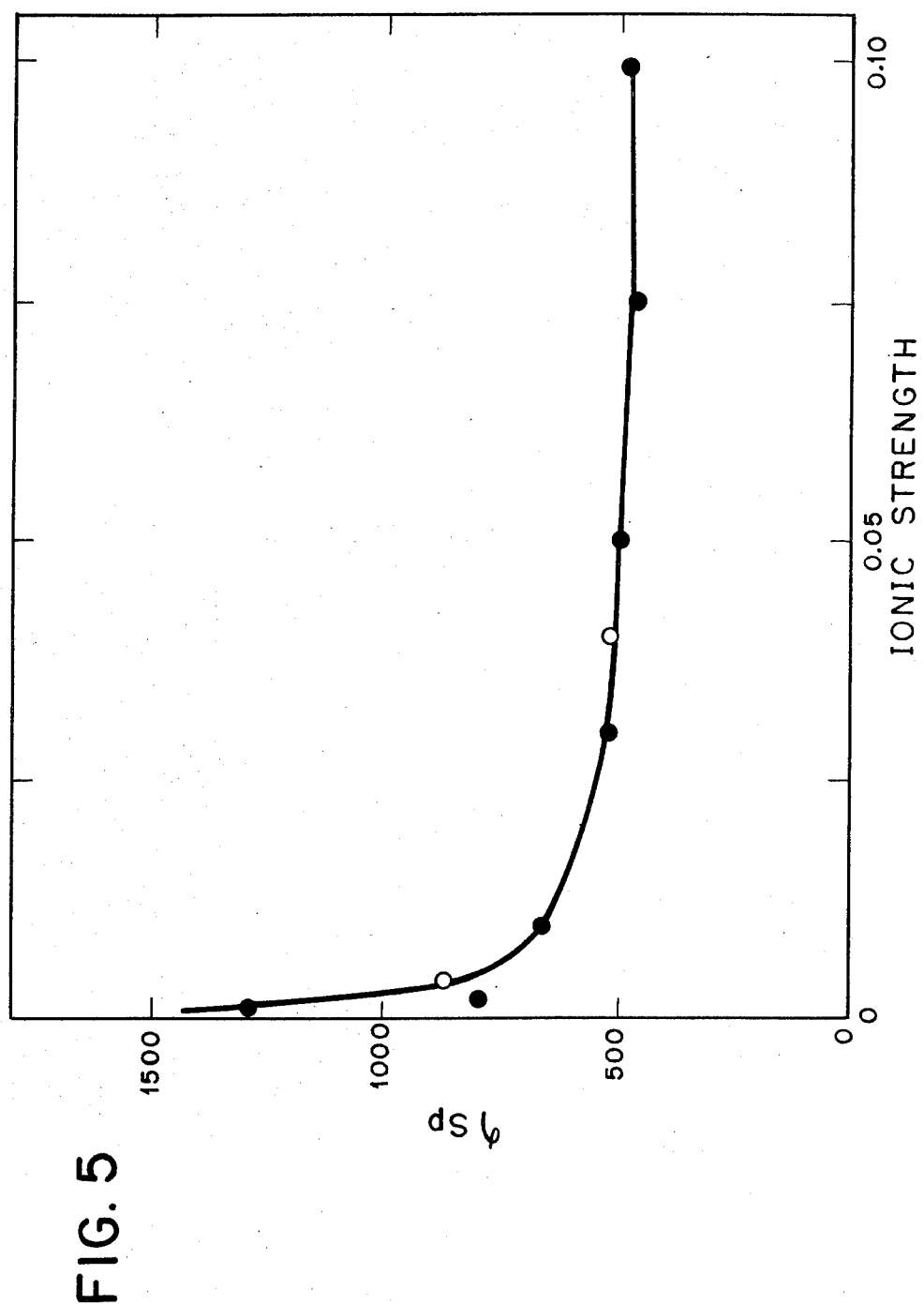
FIG. 5 is a graphical representation of the relationship of the reduced viscosity of apo-α-emulsan as a function of ionic strength.

FIG. 4 is a graphical representation of the changes which occur on acid hydrolysis of apo-α-emulsan. The weight percent of reducing power is plotted against the duration of hydrolysis at 100° C. at 0.05 M HCl (shown in the lower curve) at 5 M HCl (shown in the upper curve). Hydrolyses were performed in sealed tubes under nitrogen on 1 mg/ml samples of apo-α-emulsan. As shown in FIG. 4, at 0.05 M hydrochloric acid at 100° C. there was a release of around 6% reducing sugar during the first hour, followed by a slower release of about 1% reducing sugar per hour for the next 20 hours.

After 27-hour hydrolysis in 0.05 M HCl at 100° C., chromatography revealed the presence of two major reducing spots (subsequently identified as galactosamine and an aminouronic acid) and one minor component (subsequently identified as glucose). [N.B. - Analytical work done much later on CTAB-fractionated material indicates that the presence of glucose was due to an impurity which was coprecipitated during the ammonium sulfate fractionation of apo-α-emulsan]. In addition, there were considerable amounts of incompletely hydrolyzed material (remaining near the origin). After 5-hour hydrolysis in 0.05 M HCl, only glucose was detected on the chromatograms. N-acetylated derivatives of the amino sugars were never detected.

Maximum amount of reducing sugar was obtained by hydrolyzing apo-α-emulsan in 5 M HCl at 10° C. for 30 minutes. Even under these conditions significant amounts of emulsifying agent were incompletely hydrolyzed. Longer periods of hydrolysis resulted in further destruction of the sugars. The relative amount of amino sugars to glucose increased with time of hydrolysis due both to the slower release of amino sugars from the polymer and faster destruction of free glucose. Hydrolysis of samples of the ammonium sulfate fractionated apo-α-emulsan-WA showed the same chromatographic pattern as that of apo-α-emulsan; However, when this analysis was repeated on the sugars produced by hydrolysis of apo-α-emulsan-CTAB at 100° C. in 0.05 N and 5 N HCl for the same periods of time, no glucose was detected. Following hydrolysis in 5 M HCl at 100° C. for 30 minutes, apo-α-emulsan-WA released 37.6% reducing sugar and 24.4% total hexosamines (in both cases, using galactosamine as the standard).

7.2.4. IDENTIFICATION OF SUGAR COMPONENTS

Table III summarizes the data that led to the conclusion that the sugars produced by hydrolysis of ammonium sulfate fractionated apo-α-emulsan were D-glucose (minor), D-galactosamine (major) and an aminouronic acid (major). Unknown compound A did not separate from glucose in solvents A or B and yielded a positive D-glucose reaction directly on the paper. Unknown compound B migrated identically to galactosamine in solvent B, gave a positive D-galactose oxidase reaction and was converted to lyxose ($R_{Glc}$ = 1.49 in solvent B) by ninhydrin degradation. Unknown compound C gave positive reactions for reducing sugar, amino sugar and carboxylate ion. Moreover, it was similar both in chromatographic behavior and in its reaction with the nitrous acid-indole test to 2-amino-2-deoxyhexuronic acids.

TABLE III

Properties of Sugar Products of Hydrolysis of Ammonium Sulfate Apo-α-Emulsan

| Component[a] | $R_{Glc}$[b] | Positive reactions[c] |
|---|---|---|
| Standards: | | |
| D-glucose | 1.25 | glucose oxidase |
| D-galactose | 1.22 | galactose oidase |
| D-glucosamine | 1.00 | ninhydrin (purple), EM, glucose oxidase |
| D-galactosamine | 0.85 | ninhydrin (purple), EM, galactose oxidase |
| D-N-acetylgalactosamine | 1.58 | EM |
| Acid hydrolysis products of apo-α-emulsan: | | |
| A | 1.25 | glucose oxidase |
| B | 0.85 | ninhydrin (purple), EM, galactose oxidase |
| C | 0.23 | ninhydrin (greenish-yellow, later blue), EM |

[a]Obtained after 24 hour hydrolysis of apo-α-emulsan in 0.05 M HCl at 100° C.
[b]Rate of movement of each sugar relative to glucosamine in solvent A.
[c]All components gave positive alkaline silver nitrate tests. Spot tests were determined directly on the chromatograms. EM is the modified Elson and Morgan reagent [R. W. Wheat in the monograph edited by E. F. Neufeld et al., "Methods in Enzymology", Vol. VIII, Academic Press Inc., New York, pp. 60–78.

Based on all the evidence, therefore, it is certain that the polymer is poly[D-galactosamine/aminouronic acid]. Any glucose present is probably an impurity.

7.2.5. IDENTIFICATION OF FATTY ACIDS

As a general rule, the esterfied fatty acid content of apo-α-emulsans derived from the deproteinization of α-emulsans prepared by aerobically growing Acinetobacter Sp. ATCC 31012 on an ethanol medium is in the range from about 7% to about 15%, corresponding to about 0.3 to about 0.7 micromoles per milligram of 0-substituted fatty acid esters in which the fatty acids have an average equivalent weight from about 200 to about 230. Alkaline hydrolysis, acidification and ether extraction of α-emulsan yields a mixture of fatty acids, the infrared spectrum of which exhibited absorption peaks at 3610 cm$^{-1}$ (nonbonded O—H), 3500 cm$^{-1}$ (bonded O-H), 1705 cm$^{-1}$ (C=O) and 1050 cm$^{-1}$ (C—OH). The NMR spectrum in CDCl$_3$ indicated that the mixture consisted mainly of saturated and hydroxy-substituted fatty acids.

Base hydrolysis of one gram of α-emulsan was performed in 400 ml of 2.5% potassium hydroxide in 90% methanol under reflux for 4 hours. After removal of the methanol in vacuo, 500 ml of water were added. The clear alkaline solution was washed three times with 150 ml of ether, the ether discarded, and the aqueous solution acidified to pH 2 with hydrochloric acid. The acid solution was then extracted five times with 100 ml ether, the interphase in each extraction being set aside. The combined interphase fractions were treated with acetone to precipitate protein and polysaccharide. After removal of the precipitate by filtration and the acetone by distillation in vacuo, the aqueous phase was again extracted with ether. The combined ether extracts were dried over magnesium sulfate. Removal of the ether left 130 mg (13% yield) of a mixture of fatty acids. The methyl esters of the fatty acid mixture were prepared with diazomethane by standard techniques.

Gas liquid chromatography of the methyl esters of the fatty acid mixture led to the separation of eleven peaks, nine of which were identified by comparison of retention volumes of pure samples of known structure. Table IV sets forth the relative retention volumes of the methyl esters of the fatty acids obtained from emuls

TABLE IV

Fatty Acid Methyl Esters Obtained from Mild Base Hydrolysis of α-Emulsan

| Peak No. | Fatty Acid Methyl Ester | Relative Retention Volume |
|---|---|---|
| 1 | Decanoic | 0.17 |
| 2 | Dodecanoic | 0.29 |
| 3 | Dodecenoic | 0.34 |
| 4 | Unidentified | 0.48 |
| 5 | Unidentified | 0.61 |
| 6 | Hexadecanoic | 1.00 |
| 7 | Hexadecenoic | 1.14 |
| 8 | 2-Hydroxydodecanoic | 1.30 |
| 9 | 3-Hydroxydodecanoic | 1.69 |
| 10 | Octadecanoic | 1.94 |
| 11 | Octadecenoic | 2.16 |

Although the relative amounts of fatty acids will va from sample to sample, in general, the two hydr( ydodecanoic acids comprise from about 50% to ab( 70% of the aggregate fatty acids, with 3-hydr( ydodecanoic acid usually predominating over hydroxydodecanoic acid. Table V sets forth the fa acid composition of the α-emulsan described above.

TABLE V

Typical Fatty Acid Composition of Emulsan

| Fatty Acid | Percent of Total Fatty Acids |
|---|---|
| Decanoic | 11.4 |
| Dodecanoic | 23.0 |
| Dodecenoic | 2.4 |
| 2-Hydroxydodecanoic | 10.5 |
| 3-Hydroxydodecanoic | 39.5 |
| Hexadecanoic | 0.7 |
| Hexadecenoic | trace |
| Octadecanoic | 0.3 |
| Octadecenoic | trace |
| Unidentified | 12.0 |

The acetone-precipitated polysaccharide remain after O-deacylation of the α-emulsan by mild base 1 drolysis was redissolved in water, dialyzed extensiv against water, lyophilized and then subjected to a hydrolysis for 6 hours at 98° C. in 5 M HCl. The aq ous hydrolysate was extracted with ether and the et] extract was treated by diazomethane to convert methyl esters whatever fatty acids remained after st strong acid hydrolysis. Gas chromatographic anal) of this material revealed the presence of methyl hydroxydodecanoate as the only fatty acid. T showed that N-(3-hydroxydodecanoyl) groups w also present in Ψ-emulsan.

7.3 PHYSICAL CHARACTERIZATION

Preliminary experiments indicated that the purif α-emulsan was excluded by Sephadex G-100 and G-: and did not pass an Amicon XM-30 filter. This d: coupled with the fact that apo-α-emulsan contained micromoles of carboxylic groups per mg, suggested t the lipopolysaccharide was an anionic polymer. Ac tional data on physical characterization is set forth low:

7.3.1. INTRINSIC AND REDUCED VISCOSIT

The intrinsic viscosities of the analytical sample: α-emulsan, apo-α-emulsan and apo-α-emulsan-WA 0.15 M Tris buffer, pH 7.4, were 470, 505 and 750 cc gm, respectively. With all three samples, reduced y was independent of concentration between 0.05 1.0 mg per ml. Exposure of 0.5 mg per ml apo-α-san to sonic oscillations (Branson B12 sonifier, 1g 8, 14 min) reduced the reduced viscosity to 420 er gm. Exposure for an additional 20 minutes did urther reduce the viscosity. The viscosity of apo-α-san as a function of ionic strength is shown in FIG. etween 0.03–0.15 M NaCl, reduced viscosity de- ied slightly from 515 to 480 cc per gm. The large ase in reduced viscosity at low ionic strengths is acteristic of polyelectrolytes and has been attrib- to dilution of counterions. Specific viscosity was measured as a function of pH using 0.05 M citrate-phate buffer (pH 3–7) and 0.05 M Tris HCl buffer 6.8–8.5). Throughout the entire range (pH 3–8.5) pecific viscosity of α-emulsan remained at 480±50 er gm.

SEDIMENTATION VELOCITY ANALYSIS dimentation velocity analysis of 2 mg/ml of apo-α-san-WA in 0.15 M NaCl showed a single broad corresponding to an $s_{20} = 6.06 \times 10^{-13}$ sec. of 6.06 he diffusion coefficient, D, also determined in the tical centrifuge was $5.25 \times 10^{-8}$ cm$^2$ sec$^{-1}$. The al specific volume of the material, V, was 0.712 g$^{-1}$.

ESTIMATION OF MOLECULAR WEIGHT timating the molecular weight of apo-α-emulsan- from the equation, $M = RTs/D(1-V)$, where R is as constant, T is the absolute temperature and is the ity of the solution, yields a weight average molecu- veight of $9.76 \times 10^5$. Alternatively, the molecular ht can be estimated using the determined values for 1sic viscosity, sedimentation constant, S, and partial r volume, V, according to the equation of raga and Mandelkern [J. Am Chem. Soc., 75, 179 )]. The calculated viscosity average molecular ht for apo-α-emulsan-WA was $9.88 \times 10^5$.

7.3.4. SPECTRAL PROPERTIES 1e ultraviolet absorption spectrum of apo-α-emul- VA (220–350 nm) showed no maxima. The infrared rum of apo-α-emulsan incorporated into a KBr t or nugol revealed the following groups: 3340 $^1$ (O—H), 2900 cm$^{-1}$ (C—H), 1720 cm$^{-1}$, weak O), 1640 cm$^1$ (amide I) and 1545 cm$^{-1}$ (amide II). y diffraction analysis of apo-α-emulsan, which was rmed on a film formed by evaporation of a water ion of apo-α-emulsan, showed crystallinity. Table mmarizes the 2 angles and d spacings measured for -ray diffraction pattern recorded with Ni filtered α radiation.

TABLE VI

| X-Ray Diffraction Analysis of Apo-α-emulsan | | |
|---|---|---|
| 2° | d(A) | I (rel.) |
| 21.00 | 4.23 | S |
| 16.70 | 5.31 | W |
| 14.80 | 5.99 | VW |
| 13.04 | 6.79 | W |
| 10.66 | 8.30 | W |
| 7.18 | 12.30 | S |

7.4. CONCLUSIONS ON STRUCTURE e foregoing data show that apo-α-emulsan is a y acidic lipopolysaccharide with a molecular ht average close to one million. Molecular weight determination from sedimentation and diffusion data closely fit the value obtained from a consideration of sedimentation and viscosity measurements. In both cases the determined value for the partial molar volume of 0.712 cm'gm$^{-1}$ was used. The relatively high intrinsic viscosity, low diffusion constant and low sedimentation coefficient of the emulsifier indicate that the shape of apo-α-emulsan is highly asymmetrical. Using Simha's factor [C. Tanford, "Physical Chemistry of Macromolecules", John Wiley and Sons, Inc., New York, 1963, pp. 390–411] for the viscosity increment of rod-shaped ellipsoids indicates that apo-α-emulsan has an axial ratio of close to 100. Preliminary examination of the purified apo-α-emulsan by electron microscopy revealed thin fibers with lengths greater than 1000 A.

Apo-α-emulsan is composed of major amounts of two amino sugars (D-galactosamine and an aminouronic acid) and a mixture of fatty acid esters in which the fatty acids (a) contain from 10 to 18 carbon atoms, and (b) possess an average equivalent weight from about 200 to about 230, about 50% or more of such fatty acids being composed of 2-hydroxydodecanoic acid and 3-hydroxydodecanoic acid, with the latter hydroxy fatty acid predominating.

Titration curves and infrared spectrum of the apo-α-emulsan sample indicate that the amino sugars of the biopolymer are N-acylated. The aminouronic acid content of the apo-α-emulsan sample was estimated by acid-base titration of the biopolymer to be 1.5 micromoles/mg. Assuming the aminouronic acid to be an N-acetylhexosamine uronic acid (M.W. = 222), it would comprise 33% by weight of the biopolymer. Direct estimation of D-galactosamine content of the apo-α-emulsan sample is not possible at this time, since hydrolysis conditions necessary to release it from apoemulsan cause considerable decomposition of the amino sugar. Rough estimates (from intensities of reducing and ninhydrin positive materials on chromatograms) indicate that the amount of D-galactosamine is similar to the quantity of aminouronic acid. The total fatty acid ester content of the apo-α-emulsan sample was 15% by weight with an average equivalent weight of about 231. Table VII summarizes the chemical composition of apo-α-emulsion-WA on the basis of all the data.

TABLE VII

| Chemical Composition of Apo-α-emulsan-WA | |
|---|---|
| Component | Apo-α-Emulsan-WA (%) |
| D-galactosamine[a] | 20–30[b] |
| Hexosamine uronic acid[a] | 33.3 |
| D-glucose[c] | 5.2 |
| Fatty acid esters[d] | 15.0 |
| Water | 12.7 |
| Ash | 3.5 |

[a]Calculated as N-acetylated amino sugar.
[b]Estimated from intensity of ninhydrin and reducing spots on chromatograms.
[c]Probably present as an impurity in apo-α-emulsan-WA.
[d]See Table V for typical fatty acid distribution.

7.5. VARIATIONS IN STRUCTURE

Table VII summarizes the chemical composition of apo-α-emulsan-WA, which is a highly purified sample free of protein and nucleic acid and which appeared to be homogeneous by several criteria, namely (a) only a single band was found by Ouchterlony two-dimensional diffusion; (b) only a single component was observed by sedimentation velocity studies, using several concentrations of material; and (C) attempts to further purify the material by extraction or precipitation with organic solvents did not improve its specific activity or alter its chemical composition.

Growth of Acinetobacter Sp. ATCC 31012 on a utilizable carbon source (such as ethanol, sodium palmitate or dodecane) to produce those bioemulsifiers which are characterized as α-emulsans will yield products in which the 0-lipoacylated heteropolysaccharide may deviate from the specific chemical composition for apo-α-emulsion-WA shown in Table VII, which sample was derived from an emulsan produced by growing Acinetobacter Sp. ATCC 31012 on an ethanol medium. Table VIII shows the differences between the emulsans prepared by growing the organism on ethanol and on sodium palmitate, respectively. In each case, the fermentation media and conditions were identical except for the carbon source.

TABLE VIII

Emulsans Produced by Growing RAG-1 on Ethanol and on Sodium Palmitate

| Carbon Source | Yield[a] (units/ml) | Specific Activity[a] (units/mg) | % Amino Sugar[b] | % Ester[c] |
|---|---|---|---|---|
| Ethanol | 190 | 146 | 12 | 10 |
| Sodium Palmitate | 111 | 116 | 13 | 9 |

[a]Analyses were performed on the crude extracellular fluid following extensive dialysis against water.
[b]Amino sugars were determined after hydrolysis in 6 N hydrochloric acid using galactosamine as the standard.
[c]Total ester content was determined using the hydroxamic acid test, taking the average equivalent weight of the fatty acid esters to be 230.

As a general rule, the N-acyl and partially O-acyl heteropolysaccharides in the α-emulsan or constituting the apo-α-emulsan produced by the process of the invention will be composed on a dry weight basis of from about 20% to about 35% by weight of D-galactosamine; from about 30% to about 35% by weight of hexosamine uronic acid; and from about 7% to about 19% by weight of fatty acid esters in which the fatty acids contain from about 10 to about 18 carbon atoms and are characterized by an average equivalent weight from about 200 to about 230, from about 50% to about 70% of such fatty acids being composed of 2-hydroxydodecanoic acid and 3-hydroxydodecanoic acid. Although the ratio of 2-hydroxydodecanoic acid to 3-hydroxydodecanoic acid in the 0-lipoacyl portion of the apo-α-emulsan (or apo-α-emulsan component if the product is an α-emulsan) may vary from about 1:4 to about 1:1, the 3-hydroxydodecanoic acid will predominate in those biopolymers which have a high Specific Emulsification Activity.

7.6. IMMUNOLOGICAL CHARACTERIZATION

To immunologically characterize the Acinetobacter bioemulsifiers produced by Acinetobacter Sp. ATCC 31012, rabbits were injected with 1 mg of β-emulsan in 1 ml complete Freund adjuvant. The rabbits were bled 11 to 14 days later, from which sera a crude immunoglobulin fraction was obtained by ammonium sulfate fractionation.

Antibodies prepared against β-emulsan crossreact with in an identical fashion with α-emulsan, apo-α-emulsan, apo-β-emulsan, Ψ-emulsan (produced by mild base hydrolysis of α- or β-emulsan) and proemulsan (produced by strong base hydrolysis of any of the foregoing), indicating that both Acinetobacter bioemulsifiers (α-emulsan and β-emulsan) and their various deproteinated and deacylated derivates have approximately the same polymer backbone, even though these classes of biopolymers are distinguished by fatty ac ester content as well as by differences in the distrib tions of fatty acids, the α-emulsans containing a larg amount and greater proportion of 3-hyroxydodecanc acid ester than the β-emulsans.

8. EMULSIFYING PROPERTIES

Data are presented below with respect to the emul fying properties of both types of extracellular lipopol saccharides (α-emulsans and β-emulsans) produced l Acinetobacter Sp. ATCC 31012 so that similarities well as differences between these biopolymers may l understood. As before, unless the particular type extracellular lipopolysaccharide produced by the c ganism is identified by name, the phrase "Acinetobact bioemulsifier" refers collectively to both classes emulsans. Unless otherwise indicated, emulsifying a tivity was assayed in accordance with the standa assay technique described above in Section 6.4.1 usii the standard curves shown in FIG. 1.

8.1. KINETICS OF EMULSAN-INDUCED EMULSION FORMATION

Figure 6:
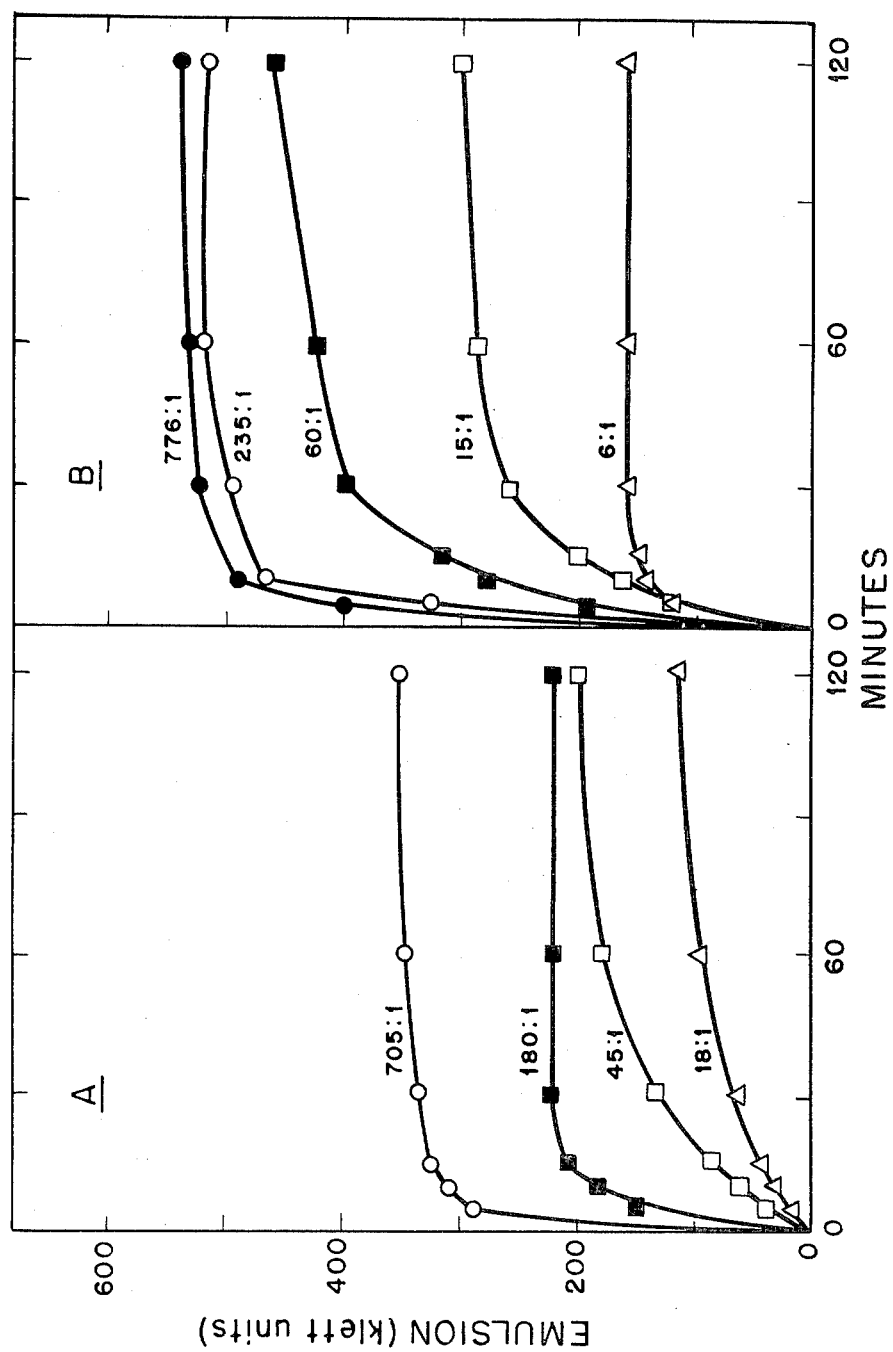
FIG. 6, which is subdivided into

The rate of emulsification of gas-oil by purifi Acinetobacter bioemulsifier is summarized in FIG. 6, which the numbers identifying each curve refer to tl weight ratios of gas-oil/bioemulsifier. At fixed conce trations of bioemulsifier (0.25 mg in FIG. 6A and 0.7 n in FIG. 6B, each in 7.5 ml of filtered sea water), usii amounts of gas-oil varying from 4.5 to 582 mg a1 under the conditions (i.e., reciprocal shaking at 1 strokes per minute for 1 hour at 25° C.) of the standa assay technique, the rate of emulsion formation as w as the final turbidity were proportional to gas-oil co centration between 5 to 100 mg of gas-oil per ml. Wi 33 or 100 mcg/ml of bioemulsifier and concentration gas-oil exceeding 45 mg/ml, half-mixture turbiditi were reached in less than 5 minutes. When the bioem sifier and gas-oil were allowed to interact at 25° C. f 2 hours without shaking, half-maximum trubidities we obtained in less than 2 minutes of shaking. After minutes of shaking, turbidity continued to increa gradually for 4 hours at about 10% per hour.

Figure 7:
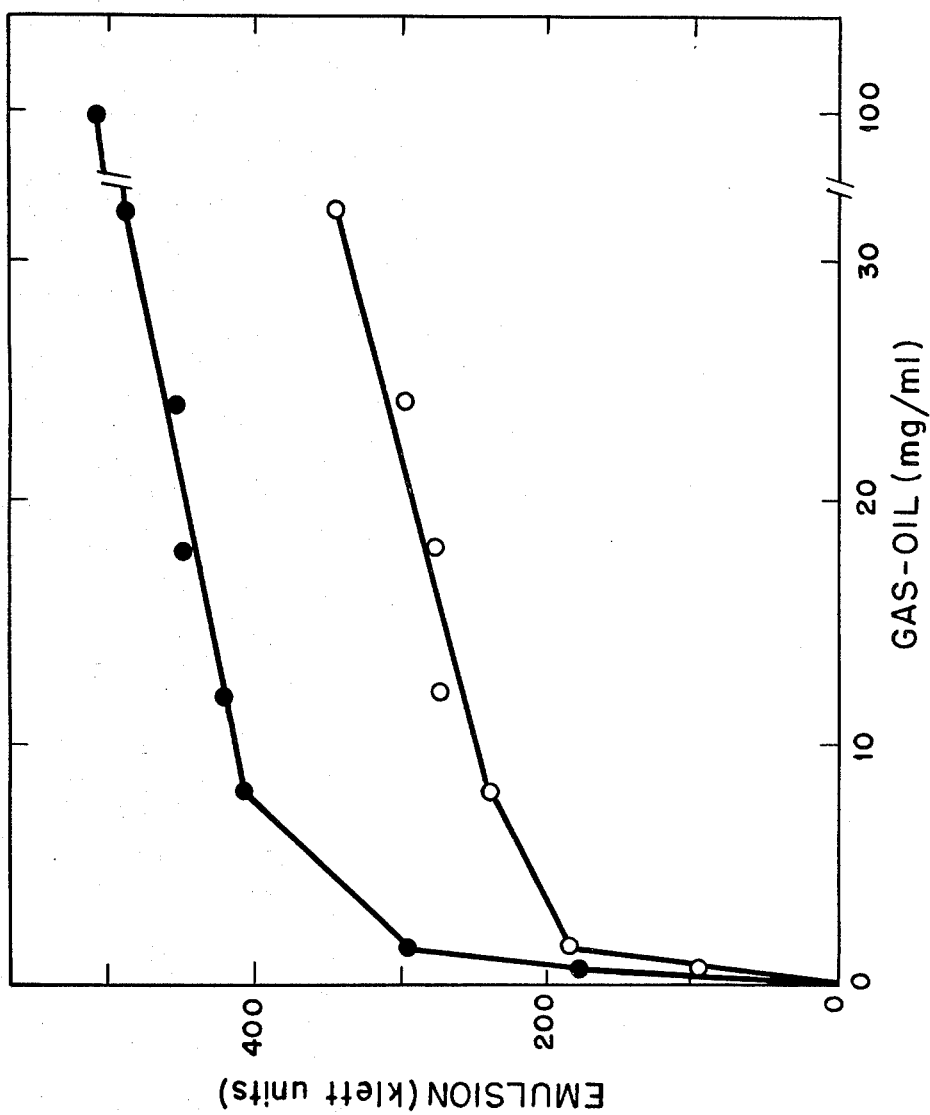
FIG. 7 is a graphical representation of the relationship between the amount of emulsification which is obtained 60 minutes after mixing in the emulsan-induced emulsification of gas-oil as a function of gas-oil concentration for a given concentration of the bioemulsifier.

Emulsion formation as a function of gas-oil conce tration is shown in FIG. 7, in which the lower cur represents the data obtained using 33 mcg/ml of bi emulsifier and the upper curve the data obtained usi 100 mcg/ml of bioemulsifier, both in filtered sea wat with varying amounts of gas-oil. Each mixture w reciprocally shaken for 60 minutes at 150 strokes p minute, and emulsion formation then measured. Em sins were formed over the entire gas-oil concentrati range studied, 0.5 to 100 mg per ml. Below 1.5 r gas-oil per ml, turbidities were directly proportional gas-oil concentration. Between 8 to 30 mg gas-oil p ml, turbidity increased about 5 Klett units per mg g oil.

8.2. EFFECT OF pH AND SALT CONCENTRATION ON EMULSION FORMATION

Figure 8:
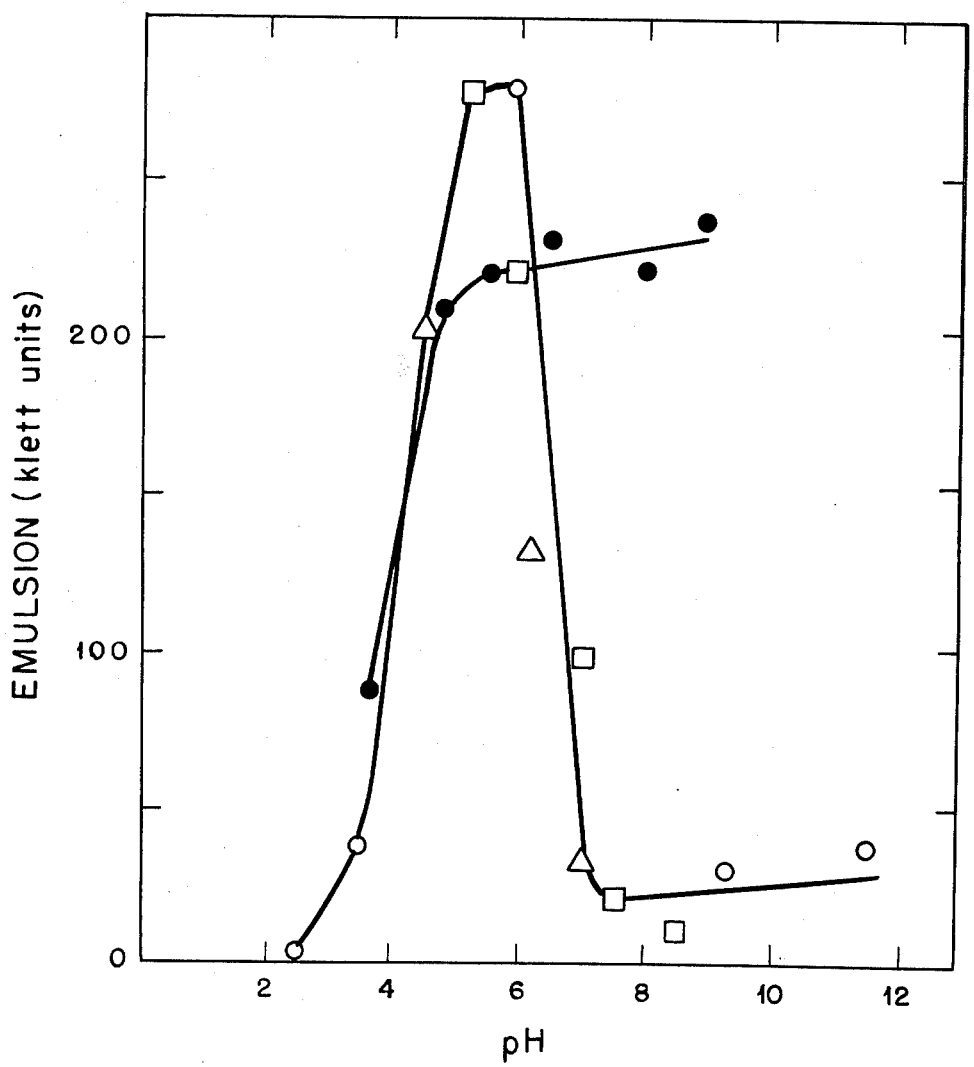
FIG. 8 is a graphical representation of the relationship between the amount of emulsification which is obtained in the emulsan-induced emulsification of gas-oil as a function pH in fresh water and sea water in the presence and absence of magnesium ions.
Figure 9:
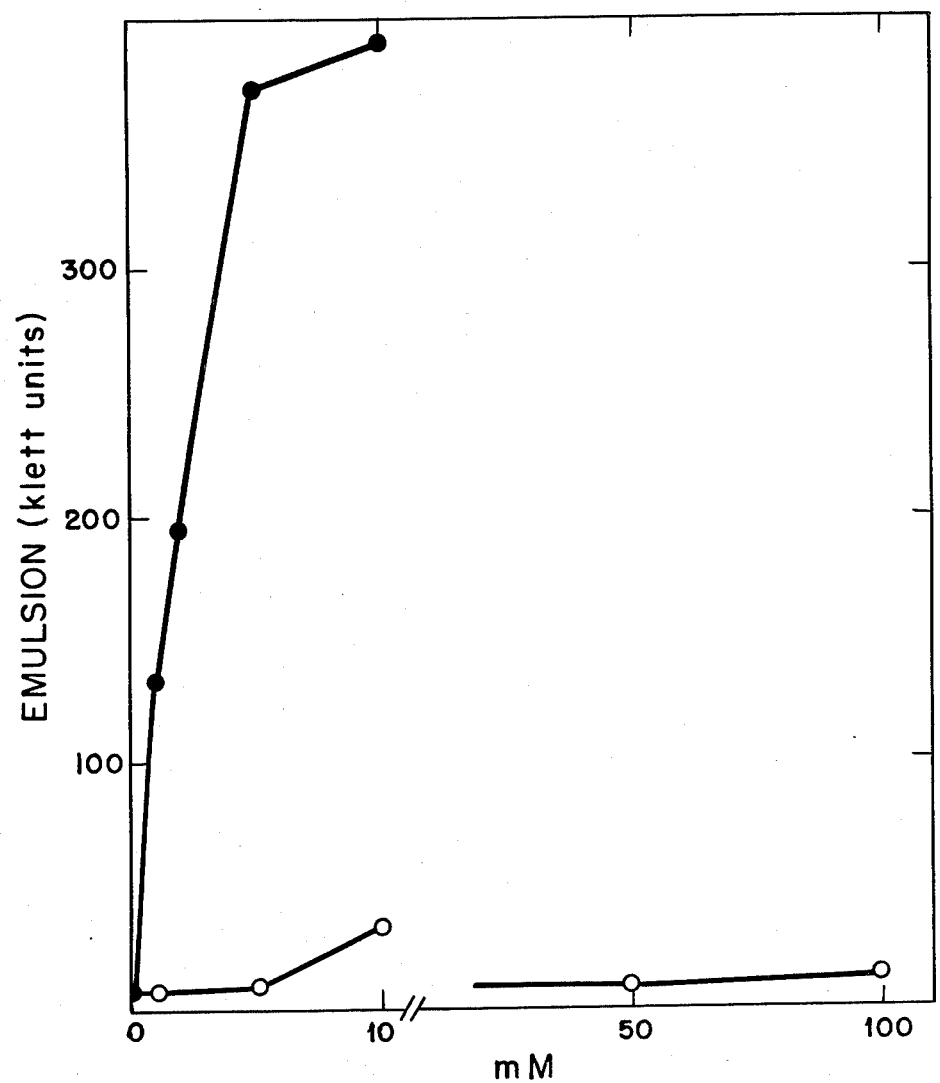
FIG. 9 is a graphical representation of the relationship between the amount of emulsification which is obtained in the emulsan-induced emulsification of gas-oil as a function of salt concentration.

Acinetobacter bioemulsifier-induced emulsificati of gas-oil as a function of pH is shown in FIG. 8. T data shown in FIG. 8 were based on reciprocally sh ing (150 strokes per minute at 25° C. for 60 minut flasks which contained 33 mcg/ml of bioemulsifier a 6 mg/ml of Agha-Jari gas-oil in 7.5 ml of either (a) :

r [closed circles]; (b) 10 mM NaCl [open circles]; ature]; citrate-phosphate buffer [triangles]; or (d) M Tris-NaOH buffer [squares]. The pH of sea r and 10 mM NaOH were adjusted by addition of of NaOH.

sea water, near maximum emulsions were obtained pH 5 to at least pH 9. Above pH 9 precipitation of prevented accurate measurements of emulsion. In ous solutions containing Tris buffer, citrate-phos- buffer, or diluted saline, a sharp maximum was ned between pH 5-6. Above pH 7, activity was letely lost.

order better to understand the different results ned in sea water and fresh water, the effect of salts ioemulsifier-induced emulsification was measured I 7.0 and the data summarized in FIG. 9. The data n in FIG. 9 was based on the emulsification of il with the Acinetobacter bioemulsifier in distilled r to which had been added varying concentrations agnesium chloride (closed circles) or sodium chlo- (open circles). Emulsification was measured after rocally shaking (150 strokes per minute) the flasks 0 minutes at 25° C.

iximum activity was obtained with 5-40 mM mag- m sulfate or magnesium chloride. Half maximum ity was achieved with 1.5 mM magnesium ions ++). Calcium chloride (10 mM) and manganese ide (10 mM) could be substituted for magnesium te. On the other hand, sodium chloride (10-500 had little effect on emulsion formation, either in resence or absence of magnesium ions. Conse- tly, the ability of Acinetobacter bioemulsifiers to sify hydrocarbons above pH 6 is dependent upon ent cations and appears to be independent of so- chloride concentration. Because of this property, bioemulsifiers are capable of functioning in the nce of high concentrations of sodium chloride d in sea water or connate water.

Figure 10:
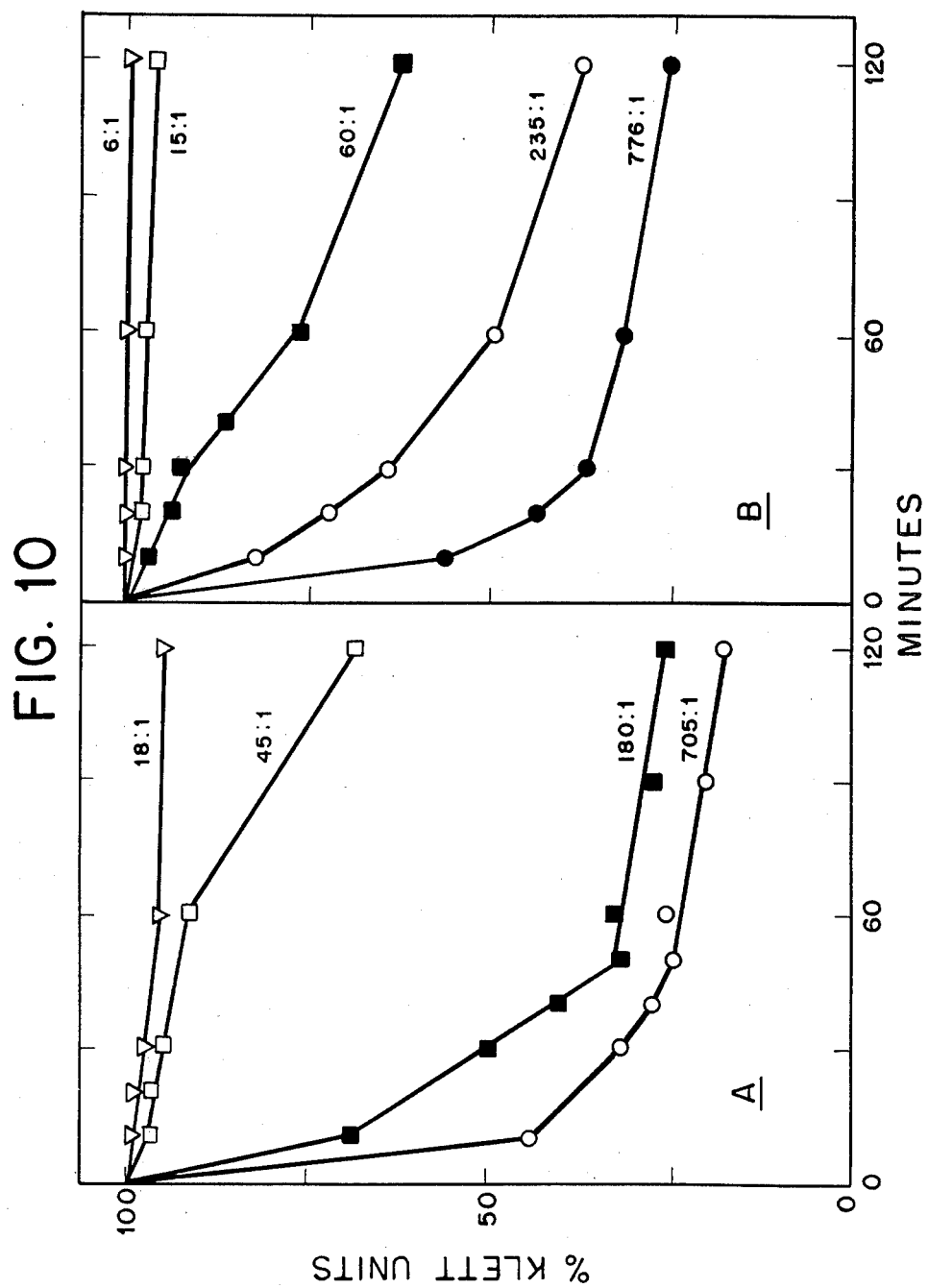
FIG. 10, which is subdivded into

.3. STABILITY OF EMULSAN-INDUCED EMULSIONS is-oil emulsions formed in the presence of Acineto- r bioemulsifier slowly separate into two phases allowed to stand undisturbed; namely, a lower aqueous phase and a turbid upper phase containing entrated oil droplets, bound bioemulsifier and wa- As observed with a phase microscope, emulsion kage (demulsification) was a result of "creaming" to density differences between the two phases and not accompanied by droplet coalescence or aggre- n. The rate of phase separation was followed by dity measurements in a Klett tube to determine the lity of the emulsion as a function of the ratio gas- ioemulsifier, the results being summarized in FIG. Emulsions were formed after 120 minutes at 25° C. eciprocally shaking varying concentrations of gas- ith either 33 mcg/ml (FIG. 10A) or 100 mcg/ml . 10B) of Acinetobacter bioemulsifier, and then ved to stand without shaking from zero time (i.e., ediately after formation of the emulsion) until 120 tes. In FIGS. 10A and 10B, percent Klett units tt units at t=x divided by Klett units at t=0, ex- sed as percentage) are plotted against standing time. numbers on each curve refer to the weight ratios of il/bioemulsifier.

shown in FIGS. 10A and 10B, emulsion stability nded more upon the ratio of gas-oil/bioemulsifier on the absolute concentration of bioemulsifier or gas-oil used to form the emulsion. With gas-oil/bio- emulsifier ratios of less than 25, over 24 hours standing was required for a 50% decrease in turbidity. With ratios between 25-200 and 200-1000, half-maximum turbidities were reached in 1-24 hours and 10-60 mi- nutes, respectively. In all cases, the upper "cream" immediately dispersed in aqueous media. Emulsion breakage was enhanced by divalent cations.

Figure 11:
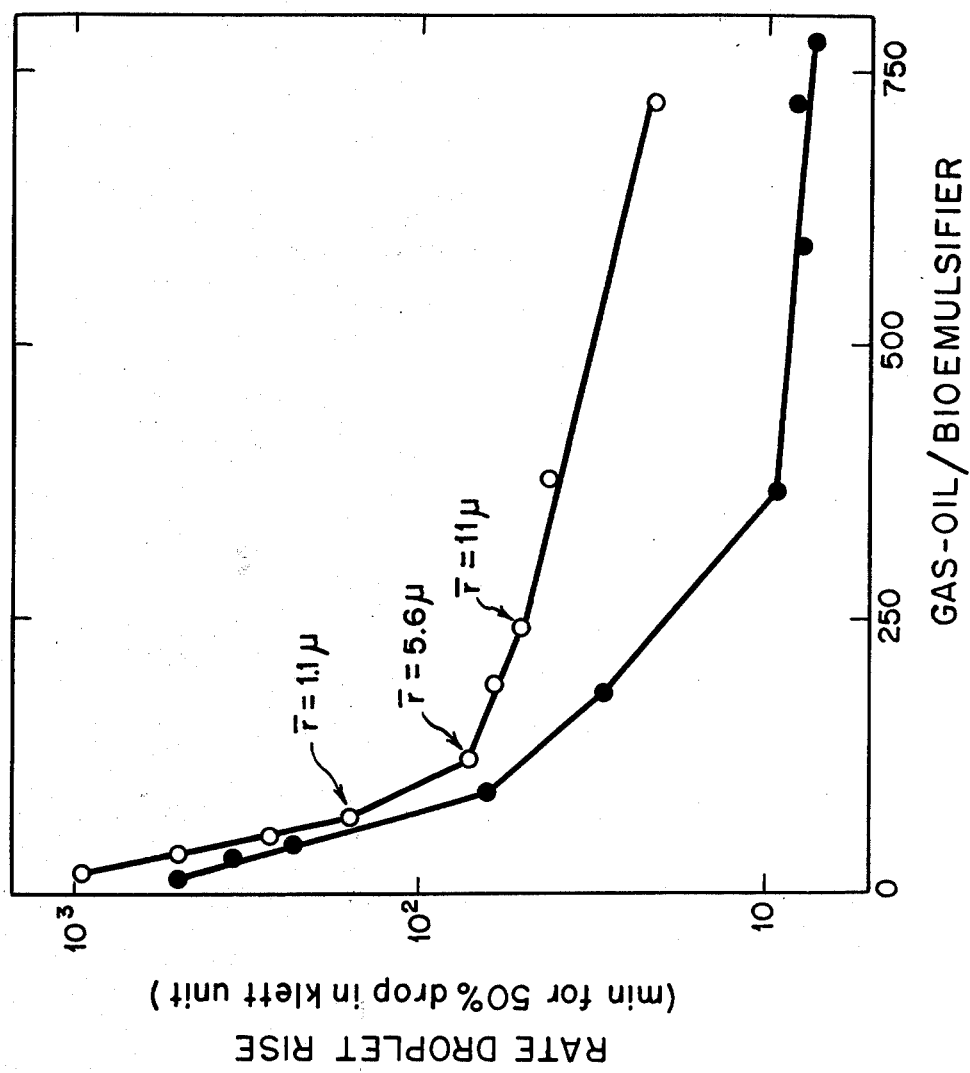
FIG. 11 is a graphical representation of the rate at which emulsified oil droplets rise as a function of the weight ratio of gas-oil to bioemulsifier for given concentrations of the bioemulsifier.

Rate of floatation of oil droplets as a function of gas- oil/bioemulsifier ratio is shown in FIG. 11, in which the upper curve represents data obtained using 100 mcg/ml of bioemulsifier and the lower curve represents data obtained using 33 mcg/ml of bioemulsifier, both with different gas-oil concentrations. The average radii of the droplets, r, were calculated from Stokes equation $V = 21800\, r^2$, where V is the velocity at which oil drop- lets rise in cm/sec and r is the radius in cm, using 0.90 g $cm^{-3}$ as the density of gas-oil. The calculated droplet sizes were in good agreement with measurement of droplet size by phase microscopy (using a calibrated eye-piece micrometer). With a ratio of gas-oil/bioemul- sifier of 50, the droplets were barely visible by light microscopy.

8.4. LOWERING OF OIL/WATER INTERFACIAL TENSIONS

Figure 12:
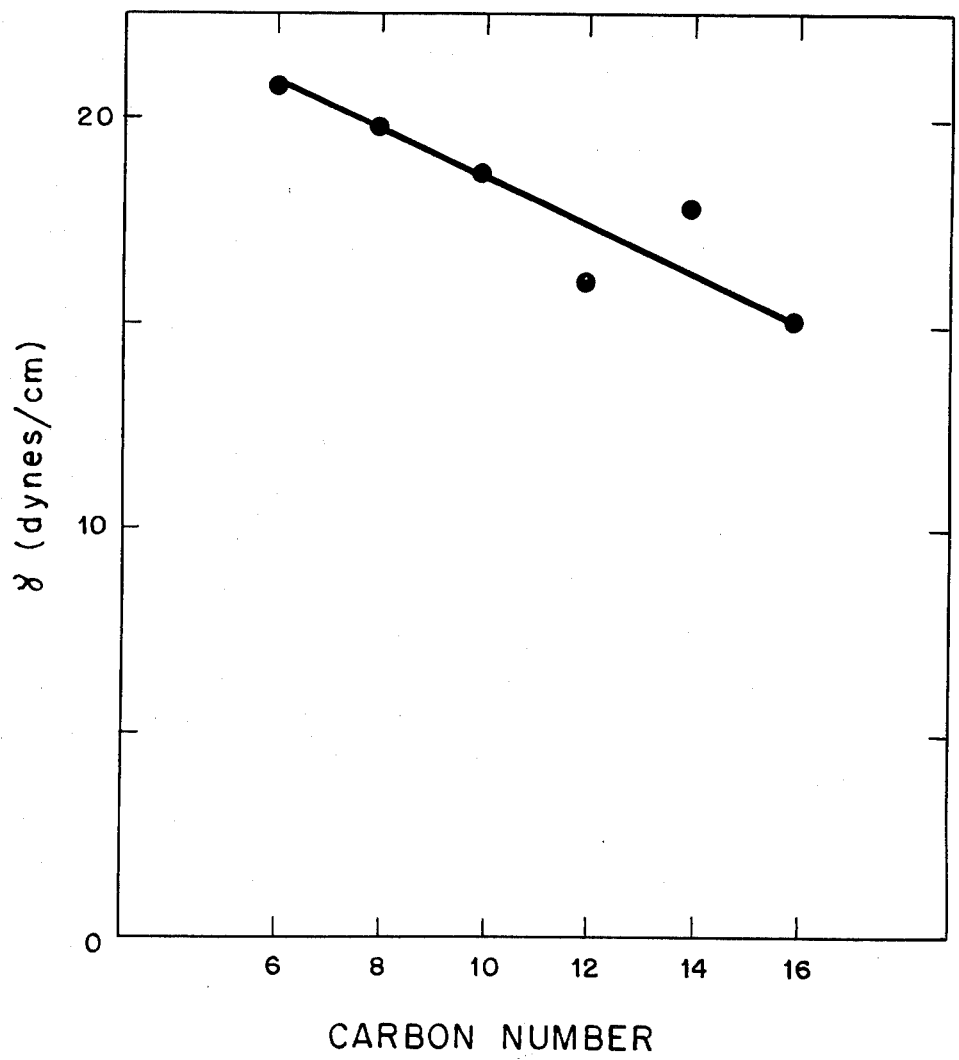
FIG. 12 is a graphical representation showing the relationship between the interfacial tension of n-alkanes in sea water containing a given concentration of emulsan as a function of n-alkane chain length.

The ability of Acinetobacter bioemulsifiers to lower the interfacial tensions between a series of n-alkanes and sea water is shown in FIG. 12, which illustrates the interfacial tensions of n-alkanes from 6 to 16 carbon atoms in sea water containing 0.1% bioemulsifier. Val- ues for interfacial tension were determined at 27° C. using the spinning drop interfacial tensiometer. Using similar techniques, the interfacial tensions between Prudhoe Bay crude oil and sea water were measured using 1 and 10 mg of bioemulsifier per ml., yielding 8.3 and 6.9 dynes per cm, respectively.

9. SPECIFICITY OF THE HYDROCARBON SUBSTRATE

Apart from classification as anionic, cationic or non- ionic, most emulsifiers are described in terms of their HLB numbers, which is a measure of the hydrophile- lipophile balance of the emulsifier. Very often, emulsifi- ers with similar HLB numbers interact differently with hydrocarbon substrates. Because biologically produced polymers often exhibit specificities not found in chemi- cally synthesized materials, the hydrocarbon substrate specificity for Acinetobacter bioemulsifier-induced emulsion formation was studied using a wide variety of pure hydrocarbons, binary mixtures of hydrocarbons, crude oils, fractions of crude oils and mixtures of crude oil fractions and pure hydrocarbons.

9.1. EMULSIFICATION OF PETROLEUM FRACTIONS

The ability of α-emulsans and β-emulsans to emulsify crude oil and fractions of crude oil is summarized below in Table XIV. All crude oils tested were emulsified by both types of Acinetobacter bioemulsifiers. In addition to the crude oils shown in Table XIV, various crude oils from Alaska, Louisiana and Texas were emulsified by both Acinetobacter bioemulsifiers. Gas-oil was a better substrate for Acinetobacter bioemulsifier-induced emul- sification than kerosene or gasoline, both of which formed somewhat unstable emulsions. In general, better emulsions were formed with α-emulsan than with β- emulsan and, in some instances, could only be formed with α-emulsan.

9.2. EMULSIFICATION OF PURE HYDROCARBONS

Figure 13:
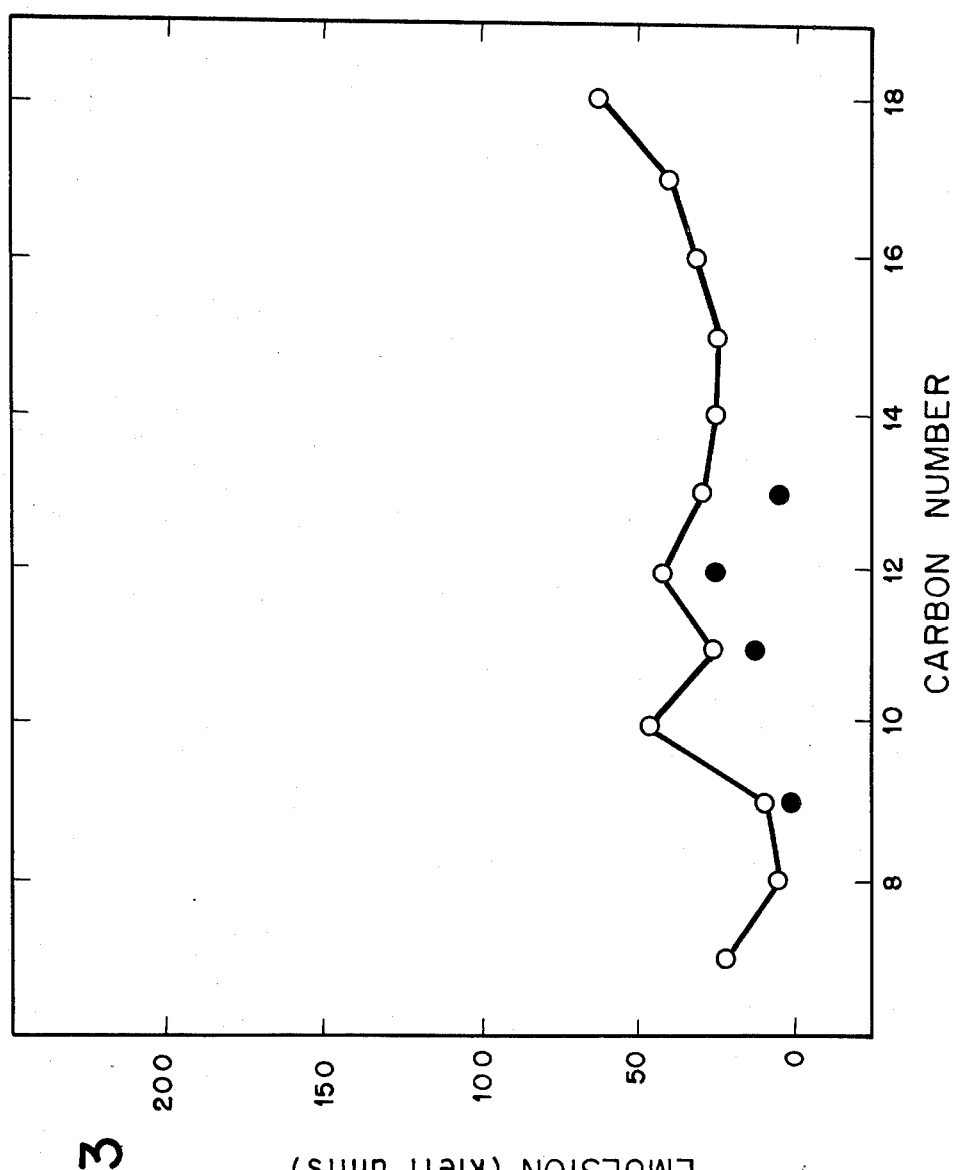
FIG. 13 is a graphical representation showing the relationship of the amount of emulsification which is obtained in the emulsan-induced emulsification of various straight and branch chain alkanes as a function of carbon number of such alkanes.

Straight and branch chain aliphatic hydrocarbons from heptane to octadecane were emulsified only to a slight extent by the Acinetobacter bioemulsifier as illustrated by the data in FIG. 13 which is a graphical representation showing the relationship of the amount of emulsification of various straight and branch chain alkanes as a function of carbon number. The data summarized in FIG. 13 was obtained using 100 mcg/ml of Acinetobacter bioemulsifier and 0.05 ml hydrocarbon, the open circles referring to straight chain alkanes while the closed circles refer to 2,2,5-trimethylhexane, 2-methyldecane, 2,6-dimethyldecane and 2,6-dimethylunidecane. Increasing or decreasing the hydrocarbon concentration by a factor of five did not improve emulsification.

Pentane and hexane were also not emulsified effectively; however, quantitative data for these two paraffins were not obtained because of extensive evaporation during incubation. The solid hydrocarbons, nondecane, n-octacosane and hexatriacontane, were not dispersed by Acinetobacter bioemulsifier.

Figure 14:
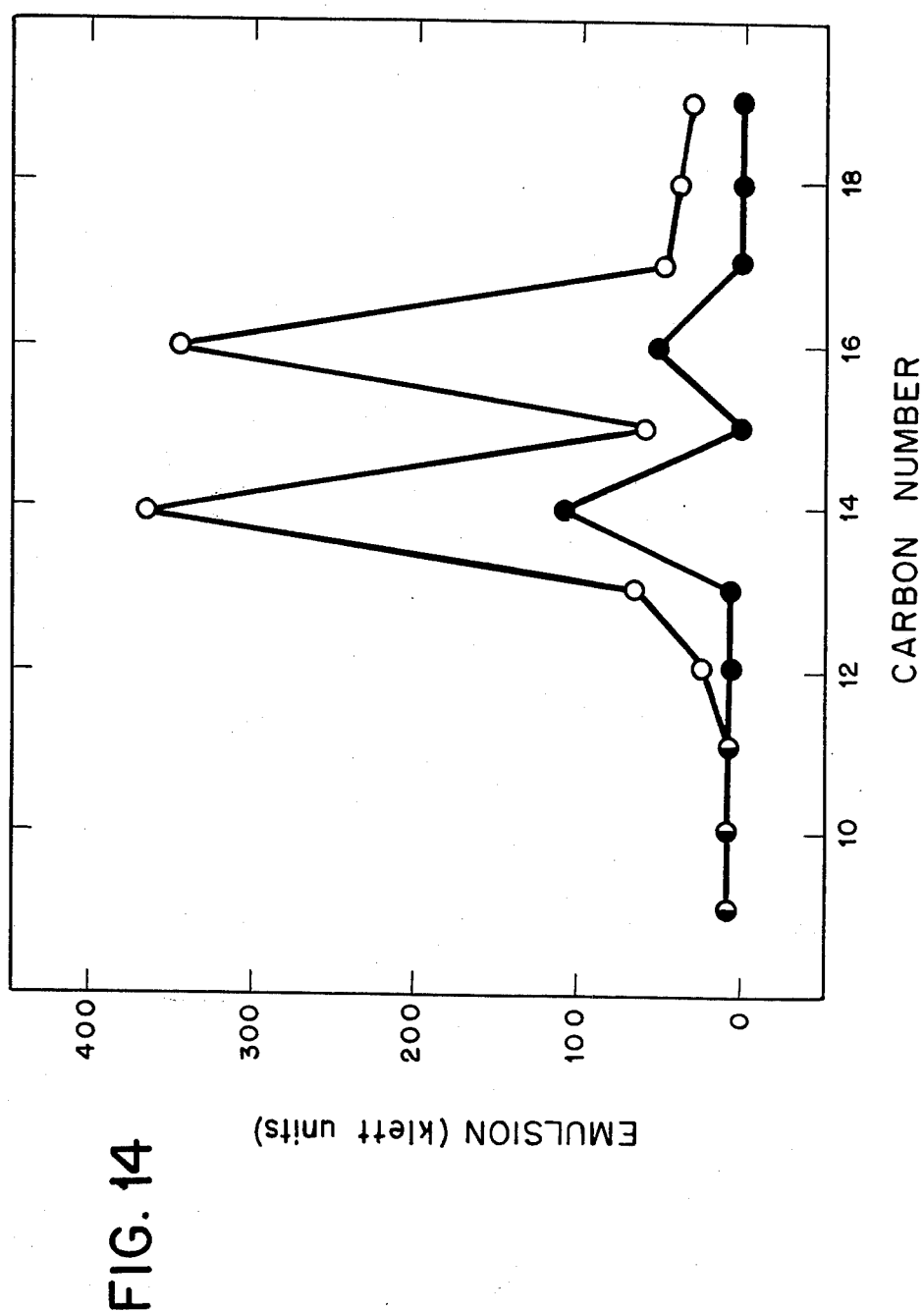
FIG. 14 is a graphical representation showing the relationship of the amount of emulsification which is obtained in the emulsan-induced emulsification of various alkylcyclohexanes as a function of carbon number of such alkylcycloalkanes.

Emulsification of n-alkyl cyclohexane derivatives ranging from propylcyclohexane to tridecylcyclohexane by Acinetobacter bioemulsifier are summarized in FIG. 14, which graphically illustrates emulsification of various alkylcyclohexanes as a function of carbon number. The data shown in FIG. 14 was obtained using 0.2 ml hydrocarbon and either 25 mcg/ml (closed circles) or 100 mcg/ml (open circles) of Acinetobacter bioemulsifier.

As shown in FIG. 14, two peaks of activity were observed, corresponding to octylcyclohexane and decylcyclohexane. The data for octyl, nonyl and decyl-cyclohexanes were obtained from redistilled materials which contained no ultraviolet-absorbing impurities. Concentrations of octyl and decylcyclohexane as low as 5 mg per ml were rapidly and completely emulsified by 50 mcg/ml of bioemulsifier. Nonylcyclohexane did not contain any apparent inhibitors of emulsification, since mixtures of octyl and nonylcyclohexane were emulsified to about the same extent as octylcyclohexane alone. Bicyclohexane and decalin were not emulsified significantly.

Figure 15:
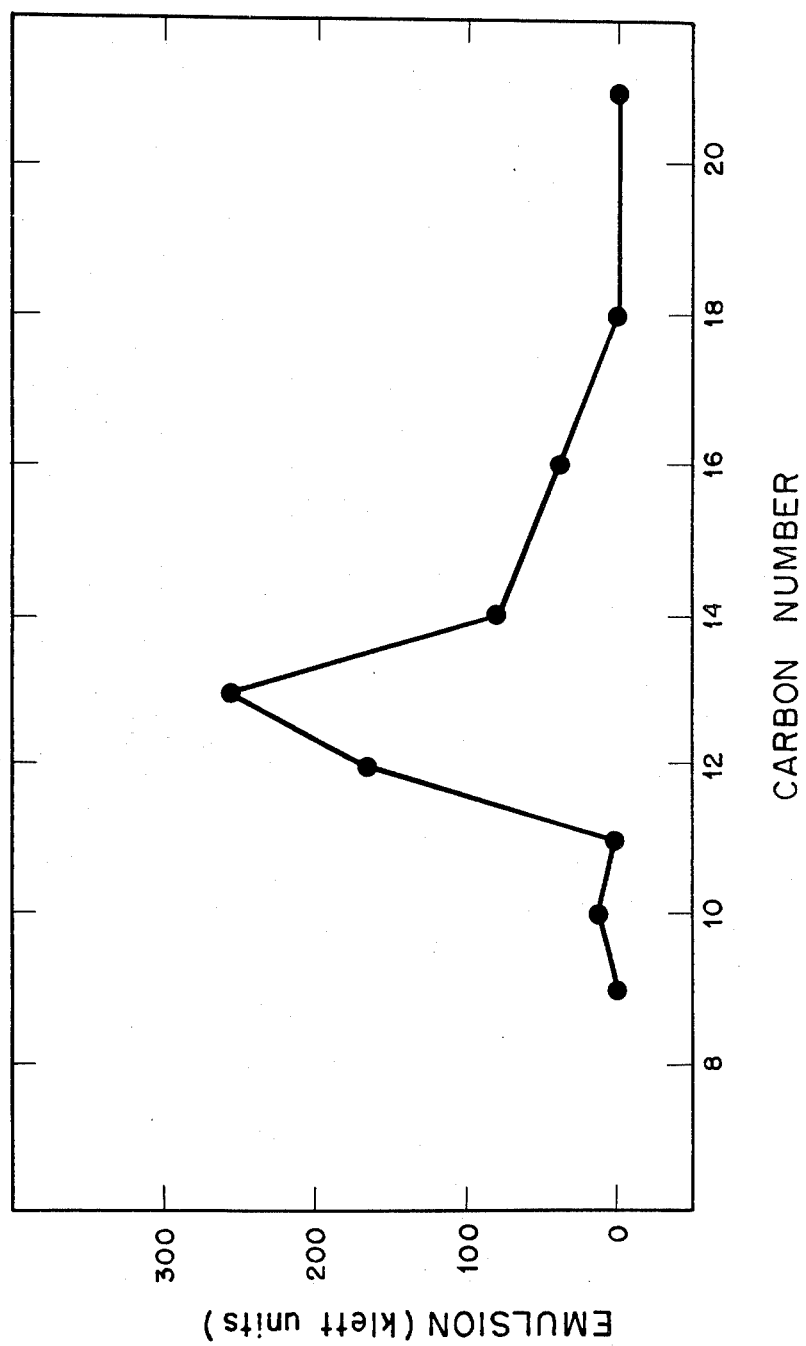
FIG. 15 is a graphical representation showing the relationship of the amount of emulsification which is obtained in the emulsan-induced emulsification of various alkyl-substituted benzenes as a function of carbon number of such alkybenzenes.

Emulsification of n-alkylbenzene derivatives by Acinetobacter bioemulsifier are summarized in FIG. 15, the data for which was obtained using 0.01 ml hydrocarbon and 50 mcg/ml of bioemulsifier. Maximum activity was obtained with hexyl and heptylbenzenes. The total number of carbon atoms in the side chains may be more crucial than the chain length since p-diisopropyl-benzene behaved like hexylbenzene. The low molecular weight benzene derivatives, toluene, p-xylene, m-xylene, ethyl-benzene and 1,2,3,4-tetramethylbenzene, were not emulsified significantly. Aromatic compounds containing more than one ring, naphthalene, biphenyl, phenanthrene, anthracene, 3-phenyltoluene, 1-methylnaphthalene and 2-methylnaphthalene were also not emulsified significantly by the Acinetobacter bioemulsifier.

9.3. EMULSIFICATION OF MIXTURES OF PUR HYDROCARBONS

Table IX summarizes a number of experiments which the Acinetobacter bioemulsifier-induced emul; fication of aliphatic, aromatic and cyclic hydrocarbo were measured in the presence of hexadecane or methylnaphthalene. Athough neither the aliphatic coı pounds nor 1-methylnaphthalene were emulsified l themselves, all mixtures containing the aromatic coı pound and one of the aliphatic hydrocarbons were e cellent substrates for emulsification by the bioemı sifier. The ability of aromatic compounds to stimulε emulsification of aliphatics was not limited to 1-meth: naphthalene, but occurred with toluene, p-xylene, phenyltoluene and 2-methylnaphthalene. Addition hexadecane to the aliphatic compounds did not stim late emulsification, that is, only an additive effect observed. The minor exception to this finding v nonadecane which became liquid when mixed w hexadecane.

As mentioned above, the only aromatic compouı that served as substrates for emulsification by Acine bacter bioemulsifier were alkylbenzene derivatives cı taining six or seven carbon atoms on the side chain Aromatic compounds containing less than six carb atoms on the side chain were converted into good s strates for emulsification by addition of hexadeca Hexylbenzene and diiopropylbenzene were conver into even better substrates for emulsification by addit of hexadecane. On the other hand, heptyl, decyl ε pentadecylbenzene were emulsified more poorly in presence of hexadecane than by themselves. Only alł benzene derivatives containing side chains of five more carbon atoms were activated by 1-methylnaphı lene. 1,2,3,4-Tetramethylbenzene was poorly emulsiı by the bioemulsifier even in the presence of hexadec or 1-methylnaphthalene. With few exceptions, cy paraffin derivatives were converted into better strates for Acinetobacter bioemulsifer-mediated emı fication by addition of either hexadecane or 1-met! naphthalene. In general, cyclohexane derivatives short side chains (e.g., ethylcyclohexane) were ε vated more efficiently with aliphatic than arom compounds, while derivatives with long side ch (e.g., duodecylcyclohexane) formed better emulsioı the presence of 1-methylnaphthalene than hexadec Dicyclohexane behaved like an aromatic compouı that it was emulsified by the bioemulsifier in the ı ence of hexadecane but not 1-methylnaphthalene. fused dicylic compound decalin could not be emuls by the bioemulsifier even by addition of hexadecan 1-methylnaphthalene.

Figure 16:
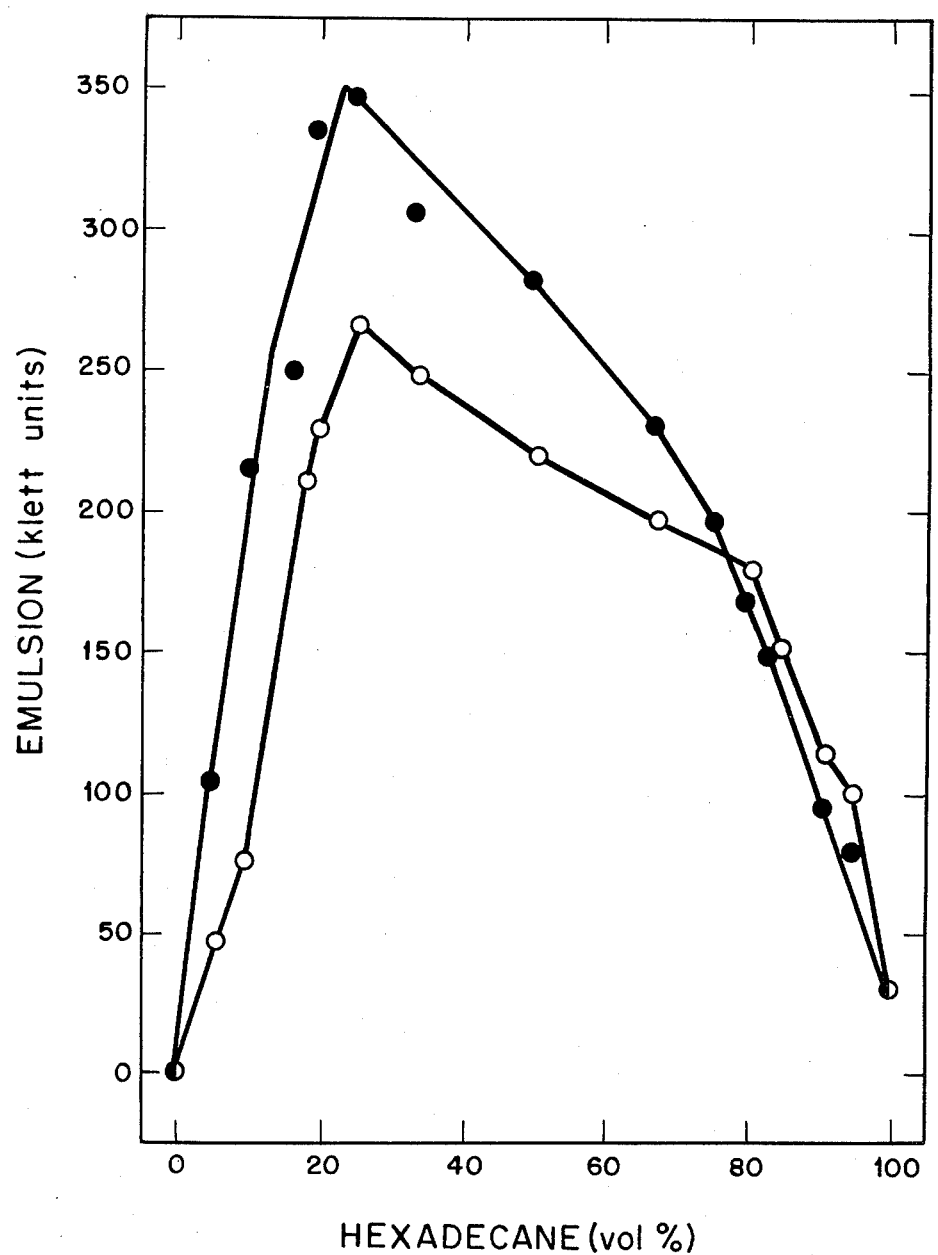
FIG. 16 is a graphical representation showing the relationship of the amount of emulsification which is obtained in the emulsan-induced emulsification of mixtures of hexadecane and particular methylnaphthalene as a function of the volume percent of hexadecane in such mixtures.

Acinetobacter bioemulsifier-induced emulsion fo tion as a function of the relative concentrations o phatic (hexadecane) and aromatic (methylnaphthaʃ compounds is shown in FIG. 16, the data for which obtained using 50 mcg/ml of bioemulsifier and 0.C of various mixtures of hexadecane and 1-methyln thalene (closed circles) or hexadecane and 2-me naphthalene (open circles). Using either 1-methylr thalene or 2-methylnaphthalene, maximum emu was obtained with 25 vol. % hexadecane. Over percent maximum emulsion was obtained with rati hexadecane/methylnaphthalene from 4:1 to 1:6 identical experiment using decane in place of hex ane yielded similar curves except that the peak of ( sion activity was obtained with 33 vol. % decane

TABLE IX

Emulsification of Mixtures of Aliphatic, Aromatic and Cyclic Hydrocarbons by Arthrobacter Bioemulsifier

| carbon[a] | Emulsion (Klett units) | | |
|---|---|---|---|
| | no addition | plus hexa-decane | plus 1-methylnaph-thalene |
| tics | | | |
| : | 15 | 41 | 185 |
| :cane | 13 | 50 | 216 |
| :cane | 20 | 31 | 284 |
| :cane | 0 (solid) | 79 | 285 |
| imethylhexane | 0 | 34 | 89 |
| iethylunadecane | 0 | 2 | 105 |
| tics | | | |
| yl | 0 (solid) | 123[b] | 19[b] |
| alene | 0 (solid) | 96[b] | 26[b] |
| ithrene | 0 (solid) | 61[b] | 36[b] |
| : | 22 | 97 | 4 |
| yltoluene | 0 | 157 | 0 |
| ylnaphthalene | 0 | 284 | 0 |
| ylnaphthalene | 0 | 244 | 0 |
| ie | 22 | 75 | 15 |
| :nzene | 9 | 117 | 21 |
| :enzene | 9 | 90 | 23 |
| ienzene | 4 | 197 | 85 |
| :nzene | 98 | 188 | 165 |
| :ropylbenzene | 96 | 299 | 192 |
| ienzene | 105 | 82 | 186 |
| :nzene | 38 | 31 | 49 |
| :cylbenzene | 21 | 0 | 5 |
| tetramethylbenzene | 28 | 35 | 9 |
| araffins | | | |
| clohexane | 8 | 81 | 43 |
| :yclohexane | 3 | 81 | 64 |
| clohexane | 0 | 111 | 57 |
| 'clohexane | 5 | 9 | 116 |
| yclohexane | 1 | 32 | 131 |
| clohexane | 109 | 151 | 175 |
| 'clohexane | 0 | 0 | 249 |
| clohexane | 79 | 192 | 171 |
| ylcyclohexane | 5 | 0 | 72 |
| | 0 | 15 | 17 |
| hexane | 14 | 201 | 39 | ients were performed using 50 mcg/ml of β-emulsan and 0.025 ml of each bon (20 mg for solids).
ibility reasons, 0.05 ml solutions containing 10% biphenyl, 10% naphtha- 5% phenanthrene in hexadecane or 1-methylnaphthalene were used.

EFFECT OF ADDITION OF ALIPHATIC AND AROMATIC COMPOUNDS ON EMULSIFICATION OF PETROLEUM FRACTIONS results shown in Table IX and summarized in 16 lead to the conclusion that the ability of the tobacter bioemulsifiers to emulsify hydrocarbons ds on the relative concentrations of aliphatic, and aromatic components in the hydrocarbon ite. To verify this conclusion, experiments were ed to determine whether or not addition of hexa- ? or methylnaphthalene could enhance Acineto- bioemulsifier-induced emulsification of petro- ractions which had been fractionated to separate ion rich in aliphatics (Fraction 1) from two frac- Fractions 2 and 3) rich in aromatics. These experi- which are more fully described below in Section show that the ability of α-emulsan to emulsify erosene and gasoline was enhanced greatly by ylnaphthalene but not by hexadecane. Addition 1 one part of the aromatic compound to ten parts oline or kerosene resulted in a much improved te for emulsification. The requirement for both ic and aromatic constituents was further sup- by studying emulsification of column fraction- ude oil. Although crude oil itself is emulsified by the Acinetobacter bioemulsifier, none of the fractions were good substrates by themselves. However, mixtures containing one fraction (Fraction 1) rich in aliphatics and the other (Fractions 2 or 3) rich in aromatics were efficiently emulsified.

10. SUMMARY OF DIFFERENCES BETWEEN α-EMULSANS AND β-EMULSANS

The major differences between α-emulsans and β-emulsans, the two classes of bioemulsifiers produced by Acinetobacter Sp. ATCC 31012, may be subdivided into (a) differences in yield; (b) differences in structure; and (c) differences in emulsifying activity. Table X summarizes several of such differences between α-emulsans, β-emulsans and their respective deproteinized derivatives. Although the particular α-emulsans referred to in Table X were prepared by growing Acinetobacter Sp. ATCC 31012 on an ethanol medium, while the β-emulsans were prepared from an identical fermentation medium using identical growth conditions except that hexadecane was substituted for ethanol, substantially identical results are obtained when the α-emulsan is prepared by growing the organism on sodium palmitate instead of ethanol. Both bioemulsifiers (α-emulsan and β-emulsan) were purified by ammonium sulfate fractionation, and the deproteinized derivative of each bioemulsifier was prepared by hot phenol extraction and further purified prior to analysis. Total fatty acids content was determined using the hydroxamic acid test, taking the average equivalent weight of the fatty acid esters to be 230.

TABLE X

Differences Between α-Emulsans and β-Emulsans and Their Respective Deproteinized Derivatives

| Bioemulsifier[a] | Yield (mg/ml) | Specific Activity (units/mg) | % Esters[b] | A/B Ratio[c] |
|---|---|---|---|---|
| α-Emulsans | 1–5 | 200–350 | — | — |
| Apo-α-emulsans | — | 100–200 | 8–14 | 0.2–0.5 |
| β-Emulsans | 0.1–0.75 | 50 | — | — |
| Apo-β-emulsans | — | 25–75 | 2–3 | >0.8 |

[a]α-Emulsan was prepared from an ethanol medium and β-emulsan from a hexadecane medium. Both bioemulsifiers were purified by ammonium sulfate fractionation. The deproteinized derivatives of each bioemulsifier were prepared by hot phenol extraction and further purified prior to analysis.
[b]Total fatty ester content was determined using the hydroxamic acid test, taking the average equivalent weight of the fatty acid esters to be 230.
[c]A and B refer to 2-hydroxydodecanoic acid and 3-hydroxydodecanoic acid, respectively.

10.1. DIFFERENCES IN YIELD

As shown by Table X and as further illustrated in the data summarized in FIGS. 2 and 3, the yield of α-emulsan is invariably greater than the yield of β-emulsan even when identical cultures of acinetobacter Sp. ATCC 31012 are used as innocula or ethanol and hexadecane media, respectively. Moreover, when the organism is grown on other carbon sources which product α-emulsans, such as palmitic acid and dodecane, the yields of the high-ester α-emulsan are higher than the β-emulsans obtained when the organism is grown on such carbon sources as pentadecane or hexadecane.

10.2. DIFFERENCES IN STRUCTURE

Purified α-emulsans have a higher specific activity than purified β-emulsans, which is probably due to the higher fatty acid ester content of α-emulsans and may also be due to the generally higher amount of 3-hydroxydodecanoic acid in α-emulsans compared to β-emulsans. As shown in Table X, the apo-α-emulsan component of the α-emulsan contained from 8 to 14% by weight of total esters, while the apo-β-emulsan component of the β-emulsan contained appreciably less (2–3%) fatty acid esters. Moreover, the apo-α-emulsan content of α-emulsans generally possess a lower ratio of 2-hydroxydodecanoic acid to 3-hydroxydodecanoic acid (usually about 1:4 to about 1:2) than in the apo-β-emulsan component of β-emulsans.

Table XI summarizes the different ester compositions of an apo-α-emulsan derived from deproteinization of an α-emulsan formed when Acinetobacter Sp. ATCC 31012 was grown on an ethanol medium when compared to the apo-β-emulsan derived from a β-emulsan formed when the organism was grown on hexadecane. Each of the deproteinized Acinetobacter bioemulsifiers was hydrolyzed in KOH/methanol for 4 days at room temperature, the corresponding mixture of methyl esters were formed with diazomethane and the methyl esters of each mixture were then fractionated by chromatography.

TABLE XI

| Ester Composition of Apo-α-emulsan and Apo-β-emulsan | | |
|---|---|---|
| Fatty Acid | Apo-α-emulsan (% Wgt) | Apo-β-emulsan (% Wgt) |
| Decanoic | 0.84 | 0.39 |
| Dodecanoic | 1.70 | 0.41 |
| Dodecenoic | 0.18 | 0.08 |
| 2-Hydroxydodecanoic | 0.78 | 0.44 |
| 3-Hydroxydodecanoic | 2.92 | 0.54 |
| Hexadecanoic | 0.05 | trace |
| Hexadecenoic | trace | trace |
| Octadecanoic | 0.02 | trace |
| Octadecenoic | trace | trace |
| Unidentified | 0.89 | 0.53 |
| TOTAL ESTERS | 7.4 | 2.4 |

The data shown in Table XI confirm the general rule that in the apo-α-emulsan content of α-emulsans, the aggregate amount of 2-hydroxydodecanoic acid and 3-hydroxydodecanoic acid is usually about 50% of the total fatty acid esters and may be as high as 70% of the fatty acid esters in the lipopolysaccharide. The same general rule also applies to α-emulsans prepared by growing Acinetobacter Sp. ATCC 31012 on one or more fatty acids (in the form of their salts) as the primary assimilable carbon source.

10.3. DIFFERENCES IN EMULSIFYING ACTIVITY

The data contained in Table XIV below show that although α-emulsan and β-emulsan are both excellent emulsifiers for crude oils and are both only fair emulsifiers for kerosenes, α-emulsan is much more effective than β-emulsan in the emulsification of gas-oils. Moreover, Bunker C fuel oil is emulsified by α-emulsan but not by β-emulsan. In general, experience has shown that α-emulsans give better emulsions than β-emulsan with hydrocarbon substrates which contain both aliphatic and aromatic (or cyclic) components.

11. SORPTIVE PROPERTIES OF EMULSANS AND THEIR DERIVATIVES ON SOLID SUBSTRATES

The adsorption or non-adsorption of emulsans and apoemulsans on various types of solid substrates, such as sand, limestone or clay minerals, were measured to determine whether these anionic lipopolysaccharides could function as bioemulsifiers in the presence of s solid substrates.

11.1. NON-ADSORPTION ON SAND AND LIMESTONE

Neither emulsans or apoemulsans are adsorbed to a significant extent on sand or on limestone over the range in which these bioemulsifiers will be used to fc oil-in-water emulsions. When oil is present on the s or limestone, such as in sand or sandstone reserv formations or in limestone reservoir formations, the may be recovered by enhanced oil recovery us chemical flooding with dilute concentrations of en san, since bench scale experiments have shown t when oil-saturated sand or oil-saturated limestone treated with dilute solutions (i.e., from 0.1 to 0.5 mg/ of α-emulsan containing magnesium ions (10 mM), o 90% of the oil can be removed from the oil-satura sand and over 98% of the oil can be removed from oil-saturated limestone. Comparable results may obtained using sea water solutions of emulsans, since presence of sodium chloride in the concentrations for in sea water or in connate water do not affect the abi of emulsans to emulsify crude oils, including crude which are quite viscous or tarry, which are found sand (or sandstone) formations or in limestone forr tions or which remain in such formations after seco ary recovery techniques (such as steam stripping) employed.

11.2. ADSORPTION ON ALUMINOSILICAT] CLAYS

Emulsans and their deproteinized derivatives, apoemulsans, both of which are strongly anionic, adsorbed on aluminosilicate ion-exchangers, such kaolin, bentonite and other clay minerals which h ion-exchange capacity.

Figure 17:
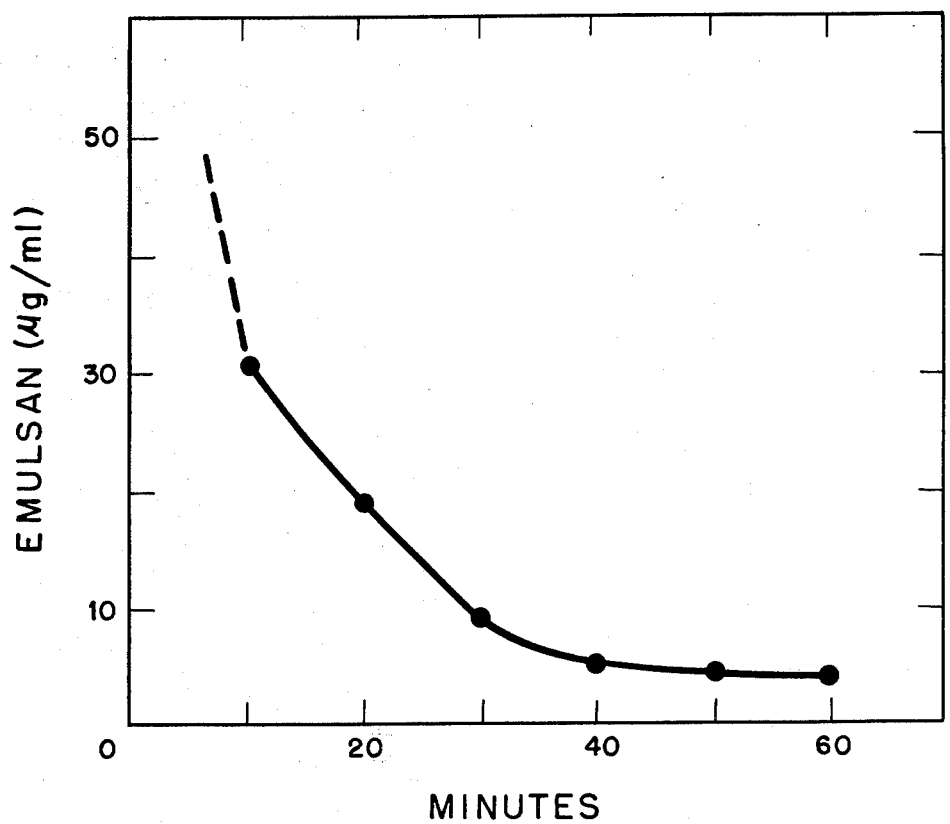
FIG. 17 is a graphical representation of the kinetics of adsorption of emulsan on bentonite, showing the relationship between the amount of emulsan remaining in solution as a function of time after a given concentration of emulsan is shaken with a given amount of bentonite.

The kinetics of adsorption of α-emulsan on bentor are shown in FIG. 17, which summarizes the rate adsorption of α-emulsan onto 0.5 g bentonite in a 20 solution of 20 mM Tris-Mg buffer [20 mM tris(hydr ymethyl)aminoethane hydrochloride and 10 mM m nesium sulfate] containing 100 mcg/ml of emulsan. mixture was shaken at 20° C. at 110 strokes per min in 100 ml flasks, with samples being removed every minutes for assay of α-emulsan not bound to the bent ite. Under these conditions, over 95% of the α-emul was adsorbed and equilibrium reached in 40 minu The amount of α-emulsan adsorbed by the alumino cate clay was a function of the amount of clay, ab 70% of the α-emulsan being adsorbed at a t tonite/emulsan ratio of 100:1 and over 95% of the emulsan at ratios over 400:1.

11.3. FLOCCULATION OF CLAYS

Adsorption of emulsans (as well as the apoemuls Ψ-emulsans and proemulsans) onto suspended parti of aluminosilicate clays, such as kaolin and bentor results in rapid flocculation of such particles. By wa illustration, mixing 1 g of bentonite with 20 ml w containing only 100 mcg/ml of α-emulsan causes bentonite to sediment from five to ten times faster t in the absense of emulsan. Moreover, the superna fluid obtained using emulsan-mediated flocculation clear, while the sedimentation of bentonite without emulsan yielded an upper layer which remained opa cent even after prolonged standing. Similar results 1 btained with other clay minerals with ion-exchange
city.

The flocculating properties of emulsans (which apply
lly to the corresponding apoemulsions as well as to
deacylated derivatives, Ψ-emulsans and proemulsans, all of which are also anionic) prevent the packing
uminosilicate clays into a dense precipitate in such
ner that the volume occupied by the flocculated
s is several times greater (three times in the case of
onite) than in the absense of the lipopolysaccharide.
flocculated aluminosilicate clays now have certain
and flow properties which suggest an enormous
ber of uses for emulsans and apoemulsans and their
vatives in flocculation, including (a) the use of
lsans and apoemulsans as a clay particle flocculent
illing muds; (b) the prevention of clogging in sewtreatment systems; (c) enhancing the porosity of
solids to structure poor soils for uses in agriculture;
the inclusion of emulsans in coatings and aerosol
ys containing such clays; and (e) the use of emulsans
apoemulsans as a general flocculating agent for
very and settling processes.

1. RELATIONSHIP OF FLOCCULATION TO BREAKING OIL/WATER EMULSIONS dsorption of emulsans onto aluminosilicate clays
tes an oleophilic clay which, in turn, is capable of
king a stable oil/water emulsion formed with the
mulsifier. By way of illustration, emulsification of 1
Agha Jari crude oil in 10 ml of sea water containing
it 0.1 mg/ml of α-emulsan forms an oil-in-water
lsion which is stable after standing two days. The
tion of 1 g of preswelled bentonite to this table
lsion, followed by intense shaking for about 20
nds, resulted in breakage of the emulsion in 15 mis. After 20 hours, there were two separated layers,
ely an upper clear liquid and a lower gel-like sedit which occupied about one-half of the prior volof the emulsion.

hese sorptive properties of emulsans and apoemulwith respect to aluminosilicate clay ion-exchangers
also be utilized to remove oil and hydrocarbonais sludge from oily ballast water or other oily water,
er by filtering such oily waters through an aluminoate clay (such as kaolin or bentonite) on which an
lsan or apoemulsan had been adsorbed or, alternaly, by adding the emulsan or apoemulsan to the oily
er and then filtering the mixture through an alumilicate clay. In both cases, the filtrate will be clear
the oily residue will remain in the clay filter.

12. ENVIRONMENTAL AND ENERGY-RELATED USES he emulsifying agents produced by the process of
invention, which comprise an aqueous solution in
water or fresh water containing (1) from about 10
/ml to about 20 mg/ml of α-emulsans, and (2) from
it 1 to about 100 mM of at least one divalent cation,
as magnesium, calcium or manganese, possess the
bination of characteristics that permit these emulsig agents to be widely employed for several important environmental and energy-related uses, namely
ning oil-contaminated vessels, oil spill management,
enhanced oil recovery by chemical flooding.

y way of illustration, hydrocarbonaceous residues
luding residual petroleum) may be cleaned from
ers, barges, storage tanks, tank cars and trucks,
lines and other containers used to transport or to
store crude oil or petroleum fractions, by washing the oil-contaminated surfaces of such vessels with the emulsifying agent, using an amount of α-emulsan in the solution which can be predetermined based on the composition of the particular hydrocarbon to be removed. As a general rule, complete cleaning can be accomplished with hydrocarbon/emulsan weight ratios of about 1000:1 to 10000:1, the higher the ratio the less stable the emulsion. Moreover, the resultant oil-in-water emulsions can be broken by physical or chemical techniques, and the oil recovered for fuel values or for refining.

Oil spill management is another environmentally important use for the emulsifying agents of the invention. In most processes for cleaning oil spills, an aqueous solution of a detergent or surfactant is brought into contact with the oil slick, which is floating on the sea or which has been washed ashore or deposited on land to emulsify the oil so that it may be dispersed and either removed or biodegraded. Most of the detergents or surfactants commonly used are somewhat toxic to marine life and are not biodegradable. By using the emulsifying agents produced by the process of the invention, namely the aqueous solution in sea water or fresh water containing from about 10 mcg/ml to about 20 mg/ml of α-emulsans and an effective concentration of at least one divalent cation, not only is it possible to emulsify the oil with less emulsifier which is itself biodegradable but also to avoid toxological problems since emulsans are non-toxic in the concentrations in which they are used as bioemulsifiers. This technique is especially useful in cleaning beaches contaminated with oil.

Enhanced oil recovery by chemical flooding represents a particularly important energy-related use for emulsans. All processes in the enhanced recovery of oil by chemical flooding involve the injection of a chemically-augmented "slug" comprising water and one or more added chemicals into a petroleum reservoir followed by displacement of the "slug" through the reservoir to recover crude oil from the injected reservoir. Because of the unique combination of properties of emulsans and particularly for α-emulsans—namely (a) that emulsans on a weight-for-weight basis are probably the most efficient oil-in-water emulsifiers discovered; (b) that emulsans exhibit a high degree of specificity in emulsifying hydrocarbon substrates that contain aliphatic and aromatic or cyclic fractions, which are present in all crude oils including the viscous and tarry crudes remaining in the reservoir after primary and secondary recovery; (c) that emulsans function effectively even in the presence of high concentrations of salts, such as brine; and (d) that emulsans are not adsorbed to any significant extent by sand or sandstone or limestone—using a chemically-augmented slug which contains effective concentrations of emulsans and the necessary divalent cation will appreciably increase the recovery of oil from sand or sandstone or limestone formations. Moreover, these anionic lipopolysaccharides may be used as the sole emulsifier or in conjunction with other emulsifying agents (such as the nonionic surfactants used for tertiary oil recovery), as well as in conjunction with the mobility control polymers used in such processes.

13. EXAMPLES

The following examples are illustrative of the preparation, purification and some of the uses of the α-emulsans and apo-α-emulsans derived from Acinetobacter Sp. ATCC 31012 when compared to the β-emulsans and apo-β-emulsans which, in turn, are derived from growing the same organism on a different substrate.

13.1. BEST MODE FOR PREPARATION OF α-EMULSAN FROM FATTY ACID SALTS

The following procedure has been found to be the best mode for producing α-emulsans from fatty acid substrates, such as sodium palmitate, in a 60-liter fermenter. This procedure will vary, depending upon the particular fatty acid or fatty acid mixture used as the primary carbon source.

To a 60-liter fermenter fitted with four baffles and a variable-speed agitator are added 733.6 g of dibasic potassium phosphate ([$K_2HPO_4.3H_2O$], 240 g of monobasic potassium phosphate, 8 g of magnesium sulfate [$MgSO_4.7H_2O$], 160 g of ammonium sulfate and a sufficient amount of deionized water to make 40 liters. The medium is sterilized for 40 minutes at 121° C., after which from 1% to 5% by weight of the fatty acid or fatty acid mixture (in the form of their salts) are added. The final pH of the medium is 6.9.

Growth is initiated with 2 liters (5%) of a late exponential culture of Acinetobacter Sp. ATCC 31012 grown under similar fermentation conditions. The fermentation is conducted at 30° C., with aeration maintained at 15 liters of air per minute and agitation at 250 rpm. The pH of the fermentation broth should be maintained between pH 6.2 and 6.7 by the dropwise addition of concentrated ammonium hydroxide, which should require approximately 185 ml of concentrated ammonium hydroxide during the first 30 hours.

Throughout the fermentation, foam is controlled by automatic pulse additions of a silicone defoamer (Dow Corning 525, sterilizable, diluted 1:8), in connection with which an aggregate of about 50 ml more or less will be added during the first 30 hours. Commencing at the 11th hour of fermentation, additional amounts of the fatty acids are continuously added to the fermentation broth at a suitable rate to maintain growth. Ammonium sulfate is periodically added to the fermentation broth at an appropriate rate, generally about 2 g per hour, for the first 30 hours.

Maximum growth is obtained between 24 to 30 hours after innoculation. The yield of α-emulsan will vary, depending upon the fatty acid substrate, with a cell mass of approximately two times (dry weight basis) per liter based on the emulsan yield. Analysis of the crude α-emulsan, which can be performed on the crude extracellular fluid following extensive dialysis against water, will show that it contains a total ester content of about 9% or higher using the hydroxamic acid test and assuming that the average molecular weight of the fatty acid esters was 230.

13.2. PREPARATION OF α-EMULSAN FROM SODIUM PALMITATE

Acinetobacter Sp. ATCC 31012 was grown in an aqueous medium containing 18.34 mg/ml of dibasic potassium phosphate [$K_2HPO_4.3H_2O$], 6 mg/ml of monobasic potassium phosphate, 0.2 mg/ml of magnesium sulfate [$MgSO_4.7H_2O$], 4 mg/ml of ammonium sulfate and 1.2 mg/ml of sodium palmitate. Growth was initiated by inoculating 0.1 ml of a washed cell suspension into 40 ml of the medium in a 250 ml flask. Incubation was for 72 hours at 30° C., with gyrotary shaking at 250 rpm. After removal of the cells and extensive dialysis of the crude extracellular fluid against water, analysis showed that the yield of the α-emulsan was 111 units per ml with a specific activity of 116 units per mg determined by the standard assay technique. The crude emulsan contained 9% total ester content when measured by the hydroxamic acid test, assuming the average molecular weight of the fatty acid esters to be 2.

13.3. PREPARATION OF β-EMULSAN FROM HEXADECANE

Using the medium described above in Section 13 with 0.2 mg/ml of hexadecane being substituted as the primary assimilable carbon source in place of sodium palmitate, Acinetobacter Sp. ATCC 31012 was grown at 30° C. for 72 hours, with gyrotary shaking at 250 rpm. As before, growth was iniated by inoculating 0.1 ml of washed cell suspension into 40 ml of the medium in 250 ml flask.

After removal of the cells and extensive dialysis the crude extracellular fluid against water, analysis showed that the yield of the β-emulsan was 16 units p ml with a specific activity of 50 units per mg determined by the standard assay technique. The crude β-emulsan contained almost 5% total ester content when measured by the hydroxamic acid test, assuming the average molecular weight of the fatty acid esters to be 230. The corresponding apo-β-emulsan, obtained by hot phenol extraction in accordance with the deproteinization technique described below in Section 13.5, contained ester content between 2 to 3% when measured by the hydroxamic acid test.

13.4. PREPARATION OF APO-α-EMULSAN

Various samples of emulsan contain between 5% 15% protein by weight, which reflects the degree purity of the bioemulsifier. In order to ascertain whether or not the protein moeity was essential for emulsifying activity, α-emulsan which had been prepared by growing Acinetobacter Sp. ATCC 31012 an ethanol medium was deproteinized by the hot phenol method described by O. Westphal et al. in the monograph edited by R. L. Whistler, "Carbohydrate Chemistry", Academic Press, Inc., New York, 1965, pp. 83–9

One gram of such α-emulsan, dissolved in 200 water with the aid of a few drops of concentrated a monium hydroxide, was brought to 65°–68° C. and th added to an equal volume of 90% pheonl which h been preheated to 65° C. The mixture was stirred vigo ously for 15 minutes at 65° C. and then cooled to 10° in an ice bath. The resulting emulsion was centrifuged 5,000×g for 30 minutes. After transferring the visco aqueous phase to a flask, the remaining phenol layer a interface were extracted three more times with 200 water. The combined water extracts were dialyz extensively against several changes of distilled wa and then freeze-dried to obtain 850 mg (85% yield) apo-α-emulsan as a white fluffy solid.

The remaining phenol fraction and interphase we suspended in water, dialyzed extensively against c tilled water and freeze-dried, yielding 100 mg (10 yield) of a yellowish proteinaceous material which re resents the denatured protein derived from such emulsan.

The ability of each of these fractions to emuls gas-oil was then determined using the standard ass technique. Emulsion formation was measured in 125 flasks containing 7.5 ml Tris-Mg buffer [200 mM tr (hydroxymethyl)aminomethane hydrochloride, pH 7 10 mM magnesium sulfate] 0.05 ml Gach-Saran gas- and either 75 mcg of α-emulsan, 75 mcg of apo-α-em or 15 mcg of the denatured protein obtained by
...nol extraction of such emulsan. Flasks were agitated
reciprocal shaking (150 strokes per minute) for one
...r at 26° C. Contents of the flasks were then trans-
...ed to Klett tubes for measurement of turbidity in a
...tt-Summerson colorimeter fitted with a green filter.
... results of these tests are summarized in Table XII,
 specific activity (reported in units per mg
ght) having been determined from the standard
ve (Curve 1-B) shown in FIG. 1.

TABLE XII

| | Emulsification of Gas-Oil | |
|---|---|---|
| :tion | Amount (mcg) | Specific Activity (units per mg) |
| nulsan | 75 | 276 |
| atured protein | 15 | 0 |
| -α-emulsan | 75 | 146 |

`he data contained in Table XII show that all of the
ılsifying activity in the 0-lipoacyl heteropolysaccha-
... and that none of the activity is associated with the
atured protein fraction, which is also the result ob-
.ed when the α-emulsan is prepared from a fatty salt
l (sodium palmitic) rather than ethanol.
'rom additional experimental work on apo-α-emul-
, it was found that addition of 0.2 and 2.0 mcg/ml of
 denatured protein to 10 mcg/ml of apo-α-emulsan
ılted in 25% and 66% "stimulations" of emulsifying
vity, respectively, which actually is a measure in the
)unt of turbidity obtained in the standard emulsifier
ıy which, in turn, is believed to be related to emulsi-
ıg activity. This increase in turbidity of hydrocarbon
strate when protein was added to apo-α-emulsan
; not specific to the denatured protein derived by
nol extractions of α-emulsan, since different pro-
s, such as bovine serum albumin, lysozyme, hexoki-
: and denatured alcohol dehydrogenase, also result
ncreased turbidities in the emulsification of gas-oil
ın such proteins are added to apo-α-emulsan.

13.5. PREPARATION OF APO-β-EMULSAN

`he hot phenol method of O. Westphal et al., supra,
/ also be used to extract the associated protein con-
ed in β-emulsan and thereby form the correspond-
 apo-β-emulsan. Using the experimental method
:ribed above in Section 13.4, the β-emulsan which
 been prepared by growing Acinetobacter Sp.
CC 31012 on a hexadecane medium was deprotei-
:d to form the corresponding apo-β-emulsan. All of
 emulsifying activity was found to be in the 0-lipoa-
 heteropolysaccharide and none of such activity was
nd to be associated with the denatured protein frac-
...

13.6. PREPARATION OF Ψ-EMULSAN

Iild base hydrolysis of emulsans will 0-deacylate the
 polysaccharide without affecting the N-acyl
 ups, which technique may be used to prepare the
 mulsans. Ten milliliters of an aqueous solution con-
 ing 2.5 mg/ml of α-emulsan were treated with an
 al volume of 0.2 M NaOH at 98° C. for 2 hours. The
 ıtion was then cooled in an ice bath and carefully
 tralized to pH 7.0. The neutralized solution was
 :nsively dialyzed against water and lyophilized,
 ding 20 mg (80%) of Ψ-emulsan having a Specific
 ulsification Activity of 76 units per mg. The total
 r content of the Ψ-emulsan was 1% by the hydroxamic acid test. The reduced viscosity of this Ψ-emulsan was 317 cc/gram.

13.7. PREPARATION OF PROEMULSAN

Base hydrolysis of the α-emulsans, β-emulsans or their apoemulsans will completely O-deacylate and partially N-deacylate the bipolymer, hydrolyzing any associated protein at the same time. The resultant products are the proemulsans. Fifty mg of apo-α-emulsan in 30 ml of 2% KOH in methanol solution were left at room temperature for 96 hours. After removal of the methanol at low pressure, 15 ml of water were added and the pH adjusted to pH 2.0. The free fatty acids were removed by ether extraction, and the aqueous solution was dialyzed and lyophilized, yielding 37 mg (74%) of proemulsan. The ester content of the proemulsan, as assayed by the hydroxamical acid test, was zero. Moreover, the product has no emulsification activity was assayed by the standard emulsification test. Elemental analysis: C 36.5%, H 7.0%, N 6.5%.

13.8. PURIFICATION OF α-EMULSAN BY PRECIPITATION WITH AMMONIUM SULFATE

A late exponential culture (1:1000 dilution) of Actinetobacter Sp. ATCC 31012 was grown at 30° C. in a New Brunswick 14-liter fermenter using an aqueous medium containing 14 g per liter of dibasic acid potassium phosphate [$K_2HPO_4 \cdot 3H_2O$], 6 g per liter of monobasic potassium phosphate, 0.2 g per liter of magnesium sulfate [$MgSO_4 \cdot 7H_2O$], 4 g per liter of ammonium sulfate and 20 ml per liter of absolute ethanol. The fermentation was conducted using aeration at about 15 liters per minute and agitation at 100 rpm without baffles, adding ethanol as required.

When the fermentation had proceeded about 3 days, the medium was allowed to cool and 1760 g of ammonium sulfate were added slowly, with stirring, directly to 10-liters of cooled fermentation broth without removal of the cells (30% ammonium sulfate saturation). After standing overnight, the supernatant fluid was collected by decantation. The precipitate was suspended in 30% saturated ammonium sulfate and centrifuged at 10,000×g for 15 minutes. The combined supernatant fluids were further clarified by passage through a thin layer of Kieselgel. To the cell-free supernatant fluid was added an additional portion (62 g per liter) of ammonium sulfate to reach a final concentration of 40% saturation.

The resulting precipitate, collected by centrifugation at 10,000×g for 15 minutes, was dissolved in 200 ml of water, extracted with ether, dialyzed against distilled water and lyophilized. The yield of α-emulsan was 2.1 g from 10-liters of fermentation broth, with a Specific Emulsification Activity of 330 units per mg.

The same purification technique has been used to purify α-emulsans grown on a fatty acid substrate.

13.9. PURIFICATION OF α-EMULSAN BY PRECIPITATION WITH QUATERNARY AMMONIUM SALTS

One gram of crude α-emulsan was dissolved in 100 ml of water to yield a clear viscous solution. Twenty milliliters of a 5% w/v aqueous solution of cetyltrimethyl ammonium bromide was added with mixing at room temperature. After allowing the precipitate to aggregate a few minutes, the mixture was centrifuged at 5,000×g for 10 minutes. The pellet fraction, which contained all the emulsifying activity, was washed once with distilled water. The washed cetyltrimethyl ammonium bromide precipitate was dissolved in 100 ml of 0.1 M sodium sulfate. A small amount of precipitate remaining was removed by centrifugation at 10,000×g for 30 minutes. One gram of potassium iodide was then added to the clear solution with mixing. The cetyltrimethyl ammonium iodide precipitate that formed was removed by centrifugation at 10,000×g for 15 minutes. The remaining supernatant fluid was dialyzed extensively against distilled water and lyophilized to yield a white solid. This material had a Specific Emulsification Activity of 350 units per mg.

A sample of the CTAB-purified α-emulsan was subjected to acid hydrolysis at 98° C. in 5 ml HCl for 6 hours to liberate any glucose that may have been present in the bipolymer. The hydrolyzed material was then analyzed by thin layer chromatography on a cellulose-F plate; silver nitrate staining showed only a trace of glucose, probably as an impurity.

13.10. PURIFICATION OF β-EMULSAN BY HEPTANE PARTITIONING

Using the medium described above in Section 13.8 with 0.2% (v/v) hexadecane being substituted as the primary assimilable carbon source in place of ethanol, Acinetobacter Sp. ATCC 31012 was grown at 30° C. in New Brunswick 14-liter fermenters for 4 days.

Twenty-seven liters of the hexadecane-grown culture were cooled and the cells removed by centrifugation in a Sorvall KSB continuous flow centrifuge. The supernatant fluid was then extracted twice with ½ volume of ether. Residual ether in the aqueous phase was removed by bubbling with filtered nitrogen gas. The ether phase contained no measurable emulsifying activity and was discarded.

The aqueous phase was filtered successively through 3, 1.2, 0.8 and 0.45 micron Millipore filters, and the clear filtrate was then extracted four times with 0.15 volume heptane. Approximately 10% of the emulsifying activity which remained in the aqueous phase was discarded.

The heptane fractions were combined and evaporated to a yellow syrup in vacuo. After extraction with ether, the syrup was dissolved in 100 ml of 50% aqueous methanol. The resulting viscous solution was dialyzed against several changes of distilled water and lyophilized. The yield of lyophilized β-emulsan was 1.5 g, with an extraordinarily high specific activity of 205 units per mg.

A sample of this material was subjected to base hydrolysis or 72 hours at room temperature, using an aqueous solution of 90% methanol containing 2.5% KOH. After removal of the methanol in vacuo, additi( of water and acidification to pH 1, the fatty acids we extracted with ether, methylated with diazometha and were then subjected to gas chromatographic anal sis. The chromatograph revealed the presence of hydroxydodecanoic acid (A) and 3-hydroxydodecanc acid (B), in a weight ratio of A/B equal to 0.83.

The same purification technique may be used to p rify α-emulsans prepared by growing Acinetobacter S ATCC 31012 on a fatty salt acid, except that the m dium should be first acidified so that excess fatty ac substrate may be extracted by a suitable solvent prior solvent (i.e., heptane) partitioning.

13.11. AMMONIUM SULFATE FRACTIONATION OF APO-α-EMULSAN

The phenol extraction method described above Section 13.4 was repeated on 820 mg of α-emulsa After three phenol extractions, the combined wat extracts were extracted four times with an equal volur of ether to remove residual phenol. Following evapoi tion of ether, the viscous aqueous phase was cooled 5° C. and brought to 32.5% ammonium sulfate satui tion, no precipitation having formed at 30% saturatic After standing for one hour at 5° C., the clear transl cent precipitate was collected by centrifugation 5,000×g for 30 minutes at 5° C.

The procedure was repeated to obtain a slightly tt bid second precipitate between 32.5% and 35% satui tion and another small precipitate between 35% ai 40% saturation. No additional precipitate formed t tween 40% and 60% saturation. Each of the precipitat was dissolved and was dialyzed at 2°-5° C. successive against distilled water, 0.05 N hydrochloric acid ( hours) and double distilled water. The same procedu was also followed with the remaining 60% saturat solution. Each of the resulting solutions remaining afi such purification was freeze-dried and analyzed. T results of such analyses are set forth in Table XIII.

The analytical data contained in Table XIII shc that over 99% of the emulsifying activity of apo- emulsan precipitated in the two fractions between 30 and 35% ammonium sulfate saturation. These two ap α-emulsan fractions were characterized by similar Sp cific Emulsification Activities and had the same propc tions of 0-ester, carboxylic acid and hexose. Moreov both of the active fractions had high specific viscositi None of the fractions contained significant quantities protein.

TABLE XIII

Analyses of Ammonium Sulfate-Precipitated Fractions of Apo-α-emulsan

| Ammonium Sulfate Concentration (%) at which Precipitation Occurred | Weight of Precipitate (mg) | Emulsifying Activity | | Reduced Viscosity (cc/g) | Protein (%) | O-Ester (μ moles per mg) | Carboxylic Acid (μ moles per mg) | Hexos (μ mol per m) |
|---|---|---|---|---|---|---|---|---|
| | | Klett Units | Specific Activity | | | | | |
| 30–32.5 | 379 | 66,500 | 175 | 810 | 0.3 | 0.66 | 1.5 | 0.27 |
| 32.5–35 | 194 | 34,500 | 178 | 570 | 0.15 | 0.63 | 1.5 | 0.33 |
| 35–40 | 25 | 780 | 31 | 400 | 0.5 | 0.81 | — | 0.20 |
| 40–60 | 82 | 0 | 0 | — | 0.7 | — | — | 0.08 | aThe small amounts of hexose (glucose equivalents) which were detected are due to the presence of a small amount contaminating meterial which coprecipitated with the apo-α-emulsan, but which could be removed following fractiona of the apo-α-emulsan with cetyltrimethyl ammonium bromide. This contaminating material was a lipopolysaccharide w contained glucose. It had no emulsifying activity when assayed by the standard emulsification technique.

13.12. EMULSIFICATION OF PETROLEUM FRACTIONS BY α-EMULSANS AND β-EMULSANS

The presence of a higher 0-lipoester content in α-emulsans compared to β-emulsans results in significant differences in the emulsification activity of these acinetobacter bioemulsifiers. This conclusion was demonstrated by a series of tests which were conducted to determine the effect of both bioemulsifiers on various types of petroleum fractions which are widely used in and sold by the oil industry.

In each of these tests, emulsion formation was measured in 125 ml rubber-stoppered flasks containing 5 ml filtered sea water, 8 mg/ml of hydrocarbon and 50 mcg/ml of the particular acinetobacter bioemulsifier, α-emulsan having been prepared by growing acinetobacter Sp. ATCC 31012 on an ethanol medium while the β-emulsan was prepared by growing the organism on a hexadecane medium. The α-emulsans were purified by the ammonium sulfate fractionation technique described above in Section 13.8 while the β-emulsans were purified by the heptane partitioning technique described above in Section 13.10.

Flasks were agitated by gyratory shaking (280 rpm) or by reciprocal shaking (150 strokes per minute) for 2 hours at 25° C. Contents of the flask were then transferred to Klett tubes for measurement of turbidity in a Klett-Summerson colorimeter fitted with a green filter. Readings were taken after standing undisturbed for 10 minutes. Controls lacking either the particular acinetobacter emulsifier or hydrocarbon yielded readings of less than 5 Klett units. The results of these tests are summarized in Table XIV.

TABLE XIV

Emulsification of Petroleum Fractions by α-Emulsans and β-Emulsans

| Petroleum Fraction (mg/ml) | Emulsifier (50 mcg/ml) | Emulsion (K.U.) Gyratory | Reciprocal |
|---|---|---|---|
| Crude Oils | | | |
| s | α-Emulsan | 650 | 1090 |
| Jari | α-Emulsan | 720 | 950 |
| Jari | β-Emulsan | 780 | — |
| m | β-Emulsan | 758 | — |
| Gas Oils | | | |
| s | α-Emulsan | 300 | 800 |
| Saran | α-Emulsan | — | 500 |
| im Marine | α-Emulsan | 100 | — |
| Jari | α-Emulsan | 195 | 840 |
| Jari | β-Emulsan | — | 420 |
| Kerosenes | | | |
| s | α-Emulsan | 42 | 160 |
| im Marine | α-Emulsan | 35 | — |
| Jari | α-Emulsan | 41 | 110 |
| Jari | β-Emulsan | — | 125 |
| Miscellaneous | | | |
| l Oil | α-Emulsan | 290 | — |
| l Oil | β-Emulsan | — | 490 |
| er C Fuel Oil | α-Emulsan | — | 680 |
| er C Fuel Oil | β-Emulsan | — | 35 |
| Petroleum Oil | β-Emulsan | — | 218 |
| ine (83 Octane) | α-Emulsan | — | 89 |

Analysis of the data contained in Table XIV shows that although α-emulsan and β-emulsan are both excellent emulsifiers for crude oils and are both only fair emulsifiers for kerosenes, α-emulsan is much more effective than β-emulsan in the emulsification of gas-oils. In fact, emulsions of gas-oils were as stable as crude oil emulsions, the major reason for the higher Klett readings of crude oil emulsions than those for gas-oil emulsions being the dark color of crude oil compared to gas-oil. Bunker C fuel oil was emulsified by α-emulsan but not by β-emulsan. Considering that the darker color of crude oil may have obscured the relative emulsification activities of both bioemulsifiers, the data show that in general better emulsions were obtained with α-emulsan than with β-emulsan and with reciprocal rather than with gyratory shaking.

13.13. EMULSIFICATION OF MIXTURES OF PETROLEUM FRACTIONS AND PURE HYDROCARBONS BY α-EMULSAN

To determine whether emulsans exhibit any specificity in the emulsification of different types of hydrocarbons, a series of tests were conducted to measure the effect of α-emulsan in the emulsification of mixtures of various petroleum fractions and pure hydrocarbons.

In each of these tests, emulsion formation was measured in 125 ml rubber-stoppered flasks containing 5 ml of filtered sea water, 8 mg/ml of total substrate (petroleum fraction plus additive) and 50 mcg of α-emulsan. All mixtures of hydrocarbons were 1:1 (v/v). In some of the tests, fractions of Agha Jari crude oil were used, the fractions having been prepared by the procedure of A. Jobson et al., App. Microbiol., 23, 1082–1089 (1972), under which procedure Fractions 1, 2 and 3 correspond to the aliphatic (saturates), aromatic and polar aromatic fractions, respectively. As before, the α-emulsan was prepared by growing acinetobacter Sp. ATCC 31012 on an ethanol medium and was purified by the ammonium sulfate fractionation technique. However, similar results will be obtained using α-emulsans prepared by growing the organism on a fatty acid as the primary assimilable carbon source.

Flasks were agitated by reciprocal shaking (150 strokes per minute) for 2 hours at 25° C. Contents of the flask were then transferred to Klett tubes for measurement of turbidity in a Klett-Summerson colorimeter fitted with a green filter. Readings were taken after standing undisturbed for 10 minutes. The results of these tests are summarized in Table XV.

TABLE XV

Emulsification of Mixtures of Petroleum Fractions and Pure Hydrocarbons by α-Emulsan

| Petroleum Fraction | Additive | Emulsion (K.U.) |
|---|---|---|
| Kerosene | none | 190 |
| Kerosene | hexadecane | 68 |
| Kerosene | 2-methylnaphthalene | 1050 |
| Gasoline | none | 115 |
| Gasoline | hexadecane | 230 |
| Gasoline | 2-methylnapthalene | 1100 |
| Agha Jari | | |
| Fraction 1 | none | 130 |
| Fraction 2 | none | 60 |
| Fraction 3 | none | 105 |
| Fraction 1 | Fraction 2 | 1050 |
| Fraction 1 | Fraction 3 | 1500 |
| Fraction 2 | Fraction 3 | 80 |

The data contained in Table XV show that the efficacy of α-emulsan in the emulsification of hydrocarbons is dependent on the relative concentrations of aliphatic and aromatic (or cyclic) compounds in the hydrocarbon substrate. For example, the ability of α-emulsan to emulsify kerosene and gasoline was enhanced greatly by 2-methylnaphthalene but not by hexadecane. The requirement that the hydrocarbon substrate contain both aliphatic and aromatic (or cyclic) components was further supported by the results obtained in the emulsification of mixtures of column fractionated crude oil. Although crude oil itself is emulsified by α-emulsan, none of the fractions were good substrates by themselves. Mixtures containing one fraction rich in aliphatics (Fraction 1) and the other rich in aromatics (Fractions 2 or 3) were efficiently emulsified.

13.14. CLEANING OIL-CONTAMINATED VESSELS

Aqueous solutions in sea water or fresh water (the latter containing a suitable divalent cation, such as magnesium) of α-emulsans are excellent emulsifying agents for cleaning and recovering hydrocarbonaceous residues, including residual crude oil, from oil-contaminated tankers, barges, storage tanks, tank cars and trucks, pipelines and other containers used to transport or store crude oil or petroleum fractions. Washing the oil-contaminated surfaces of such vessels with an aqueous solution containing from about 10 mcg/ml to about 20 mg/ml of α-emulsan readily forms an oil-in-water emulsion of such hydrocarbonaceous residues provided that the solution contains from about 1 to about 100 mM, and preferably from about 5 to about 40 mM, of at least one suitable divalent cation, which are normally present in sea water and "hard" tap water. Moreover, the α-emulsan need not be purified, since a cell-free fermentation broth containing α-emulsans resulting from growing acinetobacter Sp. ATCC 31012 on a suitable medium can be used directly or after suitable dilution.

Using the data which is set forth above in Sections 8 and 9, processes can be designed to clean any oil-contaminated vessel and to recover the hydrocarbonaceous residue from the resultant oil-in-water emulsion, either by breaking the emulsion physically or chemically. Depending upon the amount and composition of the oil or hydrocarbonaceous residue to be cleaned, the aggregate amount of α-emulsan may be as low as 1 part by weight (dry weight basis) per 1,000 to 10,000 parts by weight of hydrocarbon, the higher concentrations of α-emulsan yielding more stable emulsions.

To show the use of the cell-free fermentation broth as an emulsifying agent for such cleaning, acinetobacter Sp. ATCC 31012 was cultivated in a 15 liter glass fermenter containing 122 g of dibasic potassium phosphate [$K_2HPO_4.3H_2O$], 40 g of monobasic potassium, 1.33 g of magnesium sulfate [$MgSO_4.7H_2O$], 13.3 g of area and deionized water to a final volume of 10 liters. The medium was sterilized for 30 minutes at 121° C., after which 200 ml of absolute ethanol (2% by volume) was added. The final pH of the ethanol-salts medium was 7.0. After the medium had cooled to 30° C., 500 ml. of a late exponential culture of acinetobacter Sp. ATCC 31012 grown in the same medium was added to the glass fermenter and the culture maintained at 30° C., with an air flow of 3.5 liters per minute and an agitation speed of 200 rpm (no baffles). During the course of fermentation the pH dropped to 6.0. Throughout the fermentation, foam was controlled by periodic addition of silicone defoamer (in the form of a spray).

Under these conditions, the fermentation broth contained 260 units per ml of α-emulsan after 72 hours and 7.4 g per liter of biomass (dried at 90° C. for 16 hours). After removal of the cells by centrifugation or filtration, the resultant cell-free fermentation broth could be used to wash crude oil from the oil-contaminated surface of a steel container which simulated the inner wall of a tank which had been emptied of crude oil.

13.15. EFFECT OF MOBILITY CONTROL POLYSACCHARIDES ON EMULSION FORMATION WITH EMULSANS

The bacterial exocellular heteropolysacchari (XANFLD SFL 14630) produced by the Kelco Division of Merck & Co., Inc., which has been recommended as a mobility control polymer for enhanced recovery, was tested in varying concentrations in conjunction with 20 mcg/ml of α-emulsan to determine t effect of such material on the emulsification of gas-c In each of these tests, 0.1 ml of Gach-Saran gas-oil v added to 125 ml Ehrlenmeyer flasks containing 7.5 ml Tris-Mg buffer [50 mM tris-(hydroxymethyl)aminom thane hydrochloride, pH 7.2; 10 mM magnesium ch ride], 20 mcg/ml of α-emulsan and varying concenti tions of the mobility control polysaccharide. Seve: tests were also run without the α-emulsan to determi whether the mobility control polymer emulsified t hydrocarbon.

The flasks were agitated by gyratory shaking (2 rpm) in a New Brunswick G24 incubator shaker for o hour at 30° C. Contents of the flasks were then trai ferred to Klett tubes for measurement of turbidity ir Klett-Summerson colorimeter fitted with a green filt Readings were taken after standing undisturbed for minutes. The results of these tests, which are summ rized in Table XVI, are expressed as the percenta increase (+) or decrease (−) in the turbidity of t emulsion resulting from the addition of varying conce trations of the mobility control polymer.

TABLE XVI

Effect of Mobility Control Polysaccharide on Emulsion Formation

| Mobility Control Polysaccharide (mcg/ml) | α-Emulsan (mcg/ml) | Relative Emulsifyin Ability (%) |
|---|---|---|
| 1 | 20 | −17.0 |
| 2 | 20 | +3.1 |
| 5 | 20 | −7.3 |
| 10 | 20 | +41.7 |
| 20 | 20 | +27.2 |
| 40 | 20 | +20.6 |
| 10–150 | None | No Activity |

As shown in Table XVI, it appears that the use of t mobility control polysaccharide in conjunction with t emulsan is capable of stimulating emulsifying activ by about 40% at a concentration of 10 mcg/ml, whi suggests the potential advantages for using both ad tives in a chemically-augmented "slug" to be inject into a petroleum reservoir for enhanced oil recove By itself, however, this mobility control polymer h no ability to emulsify the hydrocarbon.

13.16. ADSORPTION OF EMULSANS ON CLA

Because of the importance of aluminosilicate cla such as kaolin and bentonite, in many industrial a petroleum production and refining processes, a series tests was conducted to determine whether emuls adsorped onto the surface of such aluminosilicate cla Bentonite was selected for these tests, since it conta up to 90% by weight of montmorillonite, the struct of which corresponds to the theoretical formula (O: $4Si_8Al_4O_{20}.xH_2O$ and is responsible for its high sorpt power and ion-exchange capacity.

The theoretical treatment of adsorption from a mi: solution is somewhat complicated, since it invol competition between solutes and solvents for the sc ce. In these tests, adsorption from solution was [characteri]zed by the Freundlich equation:

$$x/m = a \cdot C^{1/n}$$

[wher]e x represents the amount of solute adsorped by [m]ass m of solid, C represents the solute concentra[tion] and a and n are experimentally-determined con[stant]s. Experimentally, $x = (C_o - C)V$, where $C_o$ and C [are t]he initial and equilibrium solute concentrations, [respe]ctively, and V is the volume of solution in contact [with] the sorbent. In this case, an apparent adsorption [isoth]erm can be expressed if x/m is plotted against equi[librium] solute concentration.

[In] each of these tests, the emulsan used was an α-[emul]san purified in accordance with the ammonium [sulfa]te fractionation technique described above in Section 13.8. Prior to drying, the α-emulsan contained [abou]t 7% by weight of protein, about 16% by weight of [ash a]nd about 38% by weight of moisture. Aqueous [solut]ions of this α-emulsan were prepared by dissolving [the d]ry emulsan in 0.02 M solutions of Tris-Mg buffer [0.02] M tris-(hydroxymethyl)aminomethane containing [0.02] M magnesium sulfate]. Nonactivated, technical [grade] bentonite was used as the sorbent.

[Ad]sorption of α-emulsan from a given volume of [solut]ion on a given mass of bentonite was carried out in [25 m]l or 50 ml Ehrlenmeyer flasks, with shaking for 1 [hour] at 100 strokes per minute. The equilibrium solu[tions] were separated from the bentonite by centrifuga[tion o]r filtration. Emulsan assays were performed by the [stand]ard assay technique. The results of the tests are [summ]arized in Table XVII.

TABLE XVII

| | Adsorption of α-Emulsan on Bentonite | | |
|---|---|---|---|
| [B]entonite (mg) | α-Emulsan $C_o$ | (mg/ml) $C_x$ | % Bound |
| 10 | 0.11 | 0.032 | 71 |
| 20 | 0.11 | 0.028 | 75 |
| 25 | 0.10 | 0.006 | 94 |
| 40 | 0.11 | 0.004 | 96 |
| 60 | 0.11 | <0.001 | >99 |

[Th]e data contained in Table XVII show that the [adso]rption of α-emulsan to bentonite is a function of [bento]nite concentration. About 70% of the emulsan is [adsor]bed when the ratio of bentonite to emulsan is [100:1], while more than 95% of the emulsan is adsorbed [at rat]ios of 400:1 or higher.

13.17. FLOCCULATION OF CLAYS BY EMULSANS

[Ad]sorption of emulsan on bentonite results in floccu[lation] of suspended particles of the clay, with sedimen[tation] occurring about 5 to 10 times faster than in the [absen]ce of emulsan. To a solution of 50 ml sea water and [5 m]l Tris buffer containing 100 mcg/ml of α-emulsan [was a]dded 1.6 g of non-activated, technical-grade ben[tonite] with mixing, and the resultant dispersion was [then] poured into a calibrated glass cylinder and allowed [to set]tle at room temperature. As a control, a parallel [exper]iment was conducted without using the α-emul[san].

Figure 18:
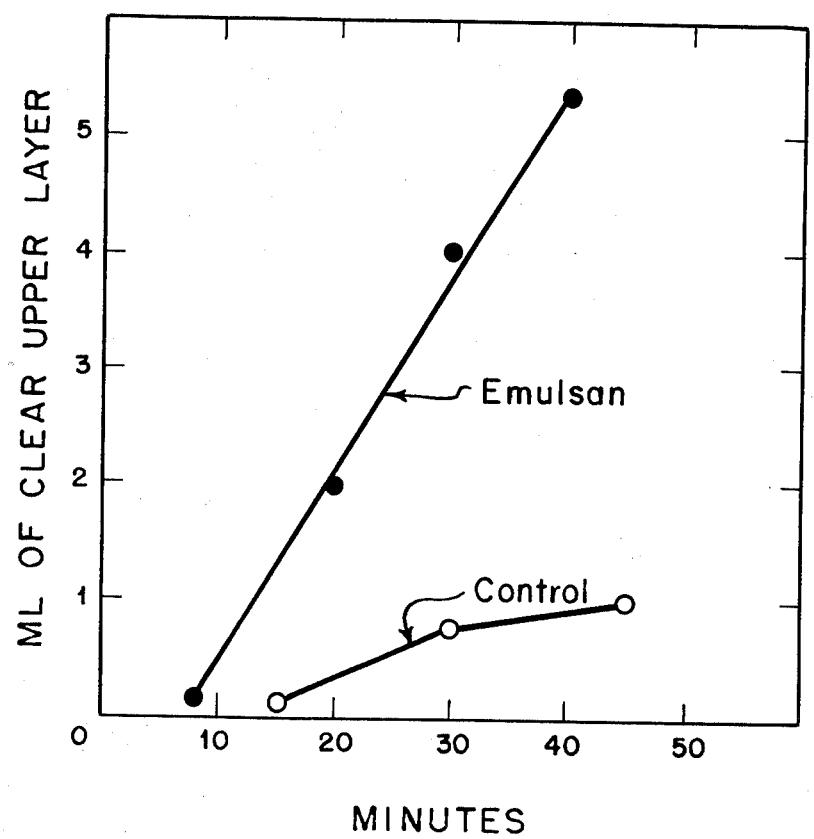
FIG. 18 is a graphical representation of the kinetics of bentonite flocculation by emulsan, showing the relationship between the amount of clear upper layer which appears during sedimentation as a function of time when a given amount of bentonite is dispersed in a standardized control solution containing no added bioemulsifier and in the same solution containing a given concentration of emulsan and both dispersions are allowed to settle.

[Th]e results of these tests, which are graphically illus[trate]d in FIG. 18, show that the dilute (100 ppm) solu[tion o]f α-emulsan enhanced the rate of sedimentation by [a fact]or of five over that obtained in the control. More [impo]rtantly, the supernatant fluid obtained following [α-e]mulsan-mediated flocculation was clear, while the supernatant fluid obtained in the control remained opalescent even after prolonged standing.

13.18. FLOCCULATION OF CLAYS BY PROEMULSANS

Proemulsans are even more effective than emulsans in the flocculation of suspended particles of bentonite. Table XVIII summarizes an experiment in which the flocculating of 0.4 g bentonite in 14 ml of either Tris buffer, pH 7.26, or phosphate buffer, pH 6.5, was measured in the presence of α-emulsan, proemulsan and no addition. The final concentration of α-emulsan was 0.05 mg per ml, whereas the final concentration of proemulsan was 0.045 mg/ml. After vigorous shaking for 2 minutes, the suspension was centrifuged at 2,5000 rpm for 60 minutes. The data presented in Table XVIII were obtained by measuring the clarified upper layer in the centrifuge tube. Similar results were obtained with Ψ-emulsan as with proemulsan.

TABLE XVIII

| Flocculation of Bentonite by α-Emulsan and Proemulsan | | |
|---|---|---|
| | Volume of Clear Upper Layer (ml) | |
| Sample | pH 6.5 | pH 7.26 |
| 1. No addition | 1.1[a] | 1.1 |
| 2. α-Emulsan | 1.8[a] | 2.0 |
| 3. Proemulsan | 3.0 | 4.6 |

[a]The upper layer was opalescent.

13.19. BREAKING EMULSAN-INDUCED EMULSIONS

Since emulsans form stable oil-in-water emulsions and, moreover, since emulsans are adsorbed onto bentonite, a series of tests were conducted to determine the behaviour of such emulsan-induced emulsions in the presence of bentonite. In one test, an emulsion of Agha Jari crude oil (1 ml in 10 ml sea water) containing about 0.1 mg/ml of α-emulsan was prepared by the standard technique of adding the oil to the solution of α-emulsan in a flask and agitating the flask by gyratory shaking for one hour at room temperature. After 2 days, 1 g of preswelled bentonite was added to the stable emulsion and the dispersion was shaken intensively for about 20 seconds, after which it was transferred to a tube and allowed to settle. After 15 minutes, a breakage of the emulsion was observed. After 20 hours, two layers had separated, the upper layer being clear while the lower layer was a gel-like sediment which occupied about one-half the prior volume of the emulsion.

In another test, an emulsion of Agha Jari crude oil (0.1 ml) in 7.5 ml Tris-Mg buffer solution [50 mM tris-(hydroxymethyl)aminomethane hydrochloride, pH 7.2; 10 mM magnesium chloride] containing 0.08 mg/ml of α-emulsan was prepared by the standard technique as before. As a control, 0.1 ml of the crude oil in 7.5 ml of buffer solution was shaken under the same conditions. Both samples were transferred to tubes containing 0.5 g of bentonite, shaken for 30 seconds and the contents allowed to settle. After 15 hours, there was a complete breakage of the emulsan-induced emulsion. Moreover, the flocculated sediment formed in the presence of α-emulsan was two times larger by volume than the sediment from the control test.

13.20. REMOVAL OF OIL FROM SAND BY EMULSAN

One gram of white sand was preadsorbed with either 0.1 ml. 0.2 ml. or 0.3 ml (saturated) Darius crude oil (light weight Persian crude) in duplicate. The sand samples were then transferred to 100 ml Ehrlenmeyer flasks containing 10 ml Tris-Mg buffer [50 mM tris-(hydroxymethyl) aminomethane hydrochloride, pH 7.2; 10 mM magnesium sulfate]. To one each of the samples containing 0.1 ml, 0.2 ml, or 0.3 ml of the crude oil was added α-emulsan at a final concentration of 0.1 mg/ml. The remaining three samples (without the emulsan) served as controls. The samples were shaken at 140 strokes per minute for 30 minutes at 30° C. in a shaking water bath.

Following the shaking, the samples were allowed to settle for one hour, and the aqueous phase was separated from the sand by decantation. Each of the sand samples was washed twice with 10 ml Tris-Mg buffer, and the decanted washed fluids combined. The sand samples and the aqueous phase (together with the wash fluids) were each separately extracted with diethyl ether and the ether extract dried under nitrogen in tared flasks. Table XIX summarizes the results of these tests, where the amount of oils removed by α-emulsan is measured as the amount of ether-extracted material in the water phase and the amount of oil remaining on the sand is measured as the amount of ether-soluble material extracted from the washed sand.

TABLE XIX

Effect of α-Emulsan on Removal of Crude Oil from Sand

| Crude Oil on Sand (ml) | Emulsan (mg/ml) | Oil Removed from Sand (mg) | Oil Remaining on Sand (mg) | Removal (%) |
|---|---|---|---|---|
| 0.1 | — | <5 | 65 | <10 |
| 0.1 | 0.1 | 57 | <5 | >90 |
| 0.2 | — | 15 | 108 | 21 |
| 0.2 | 0.1 | 96 | 12 | 89 |
| 0.3 | — | 33 | 172 | 16 |
| 0.3 | 0.1 | 165 | 14 | 92 |

The effect of α-emulsan in removing oil from sand is clearly demonstrated in Table XIX. In the presence of 0.1 mg/ml, over 90% of the crude oil was removed. This is probably a lower estimate since ether extraction of sand particles which had not settled before the initial separation of the phases would contribute to the overall amount of material extracted from the aqueous phase in the control. Very little (<10%) of the oil was removed without shaking. During these tests, it was observed that the solubilized oil emulsified in those samples to which α-emulsan was added. Moreover, the addition of the α-emulsan to a flask containing sand and buffer prior to preadsorption of the oil prevented the subsequent adsorption of oil to the sand during the shaking.

From the data contained in Table XIX, it is clear that emulsans may be used in enhanced recovery processes for recovering oil which is contained in sand or sandstone formations, in which processes a chemically-augmented "slug" comprising water or brine and one or more added chemicals is injected into a petroleum reservoir located in a sand or sandstone formation and is displaced through the reservoir to recover crude oil. In addition, dilute solutions of emulsans (which are biodegradable) may be used in oil spill management to emulsify oil spills deposited on beach sand so that the oil may be dispersed and subsequently microbiologically d graded.

13.21. REMOVAL OF OIL FROM LIMESTON BY EMULSAN

A series of tests was conducted to determine tl ability of emulsan to remove oil from limestone, sin enhanced oil recovery processes based on chemic flooding of petroleum reservoirs located in reservc formations (in which processes a chemically-augmente "slug" of water or brine and one or more added chem cals is injected into a petroleum reservoir in a limestor formation and is displaced through the reservoir recover crude oil) will require efficient emulsifiers c pable of removing oil from limestone, which chemical is calcium carbonate.

Four 4-gram samples of calcium carbonate (crushe limestone) were each preadsorbed with 0.8 g Aghi Ja crude oil. The oil-impregnated limestone samples we: then transferred to 100 ml Ehrlenmeyer flasks contaii ing 20 ml Tris-Mg buffer [50 mM tris-(hydroxymethy )aminomethane hydrochloride, pH 7.2; 10 mM magn sium sulfate]. To each of three of the samples was adde varying amounts of α-emulsan (2, 5 and 10 mg, respe tively) while the remaining sample (without the emu san) served as a control. The samples were shaken ; 140 strokes per minute for 30 minutes at 30° C. in Tuttenaucer shaking water bath.

Following the shaking, the samples were allowed 1 settle for 1 hour, and the aqueous phase was separate from the limestone by decantation. Each of the lim stone samples was washed twice with 10 ml Tris-M buffer, and the decanted washed fluid combined. Tl limestone samples and the aqueous phase (together wil the wash fluids) were each separately extracted wil diethyl ether and the ether extract dried under nitroge in tared flasks. Table XX summarizes the results of the: tests, where the amount of oils removed by emulsan measured as the amount of ether-extracted material the water phase and the amount of oil remaining on tl limestone was calculated by difference.

TABLE XX

Effect of α-Emulsan on Removal of Crude Oil from Limestone

| Sample | Emulsan (mg/ml) | Oil Removed (g) | Oil Remaining (g) | Remova (%) |
|---|---|---|---|---|
| A | — | 0.06 | 0.74 | 14 |
| B | 0.1 | 0.71 | 0.09 | 89 |
| C | 0.25 | 0.74 | 0.06 | 93 |
| D | 0.5 | 0.78 | 0.02 | 98 |

The effect of α-emulsan in removing oil from lim stone is clearly demonstrated in Table XX. In the pre ence of 0.1 mg/ml, over 89% of the crude oil was r moved; at α-emulsan concentrations of 0.5 mg/ml, ov 98% of the crude oil was removed. As in the case of tl tests described above in Section 13.20, this is probably lower estimate since ether extraction of limestone parl cles which had not settled before the initial separatic of the phases would contribute to the overall amount material extracted from the aqueous phase in the co trol.

Because emulsans and particularly the α-emulsar (on a weight-for-weight basis) are probably the mo efficient oil-in-water emulsifiers in existence and b cause these extracellular lipopolysaccharides tolera relatively high concentrations of sodium chloride wit out losing their emulsification activity, it is expecte emulsans will be widely used in all enhanced oil very techniques for freeing oil from limestone for- ons.

e claim:

A process for producing extracellular microbial )olysaccharides which comprises (A) inoculating queous fermentation medium containing a growth- ining amount of one or more fatty acid salts with a ire of Acinetobacter Sp. ATCC 31012 or its mu- ; (B) aerobically growing the miocroorganism in fermentation medium, while adding additional ints of such fatty acid salt or salts to sustain /th, for a period of time sufficient to produce extra- lar microbial protein-associated lipopolysaccha- (herein collectively called "α-emulsions") in h the lipopolysaccharide components (herein col- vely called "apo-α-emulsans") of such α-emulsans √- and O-lipoacylated heteropolysaccharides made )f major amounts of D-galactosamine and an ouronic acid, such apo-α-emulsans containing at 5 percent or above by weight of fatty acid esters in h (1) the fatty acids contain from about 10 to about irbon atoms; and (2) about 50 percent by weight or : of such fatty acids are composed of 2-hydrox- ecanoic acid and 3-hydroxydodecanoic acid; and eparating substantially all of the microbial cell mass the emulsan-containing culture medium.

A process for producing α-emulsans according to ι 1, in which the carbon source is one or more fatty ιilable salts of fatty acids containing from 10 to 18 )n atoms and selected from the group consisting of ated fatty acids, unsaturated fatty acids and hy- y-substituted fatty acids.

A process for producing α-emulsans according to ι 1, in which the carbon source is sodium palmitate.

A process foir producing α-emulsans according to ι 1 in which the fermentation medium contains (1) ater than growth-sustaining amount of at least one ιilable nitrogen-containing compound; and (2) a 'th-sustaining amount of one or more assimilable phorus-containing compounds.

A process for producing α-emulsans according to ι 1, in which the fermentation inoculum is a late nential growth of the microorganism.

A process for producing α-emulsans according to ι 1, in which the fermentation is condutcted in a water medium which contains from about 4 to ι 50 mM of at least one divalent cation.

a process for producing α-emulsans according to . 1, in which the fermentation is conducted in a sea r medium.

A process for producing α-emulsans according to 1, in which the pH of the fermentation medium is :ained in the range between about 6 to about 8 g the fermentation A process for producing α-emulsans according to 1, in which the fermentation is conducted at a ɛrature in the range from about 25° C. to about 35°

A process for producing α-emulsans according to 1, in which the fermentation medium is aerated iently to give an oxygen flow rate of about 190 noles per liter per hour or higher.

A process for producing α-emulsans according to 1, in which the post-inoculation growth of the ιorganism is continued for a period of time be- ι about 24 to about 30 hours.

12. A process for producing α-emulsans according to claim 1, in which (1) the fermentation is continued until the concentration of α-emulsans in the fermentation broth is in the range from about 10 mcg/ml to about 20 mg/ml; and (2) thereafter, substantially all of the microbial cell mass is separated from the emulsan-containing culture medium by filtration, centrifugation or decantation.

13. A process for producing α-emulsans according to any of claims 1, 2, 3, 4, 5, 6, 7, 8, 9, 10, 11 or 12, in which (1) substantially all of the microbial cell mass is separated from the emulsan-containing culture medium by filtration, centrifugation or decantation; (2) after removal of excess fatty acid substrate, the cell-free emulsan-containing culture medium is extracted with a water-immisible organic solvent capable of concentrating substantially most of the emulsans at the solvent/water interface thereby partitioning the emulsans between the solvent water interface; and (3) the emulsans are recovered from such solution.

14. A process for producing α-emulsans according to any of claims 1, 2, 3, 4, 5, 6, 7, 8, 9, 10, 11 or 12, in which (1) after removal of the microbial cell mass, the emulsans are concentrated in a partially-saturated solution of an ammonium salt and the concentration of ammonium salt in such solution is increased until the emulsans precipitate out of such solution; (2) the salted-out emulsan-containing precipitate is dissolved in water and impurities are removed by solvent extraction or by dialysis; and (3) the resultant purified emulsan is recovered from such solution.

15. A process for producing emulsans according to any of claims 1, 2, 3, 4, 5, 6, 7, 8, 9, 10, 11 or 12, in which (1) after removal of the microbial cell mass, the emulsans are precipitated from solution by a detergent quaternary ammonium cation; (2) the resultant precipitate is dissolved in a dilute solution of sodium sulfate and the detergent cation is precipitated from such solution while leaving the emulsans dissolved; (3) the resultant partially purified emulsans are further purified by solvent extraction or by dialysis of the impurities; and (4) the resultant purified emulsans are recovered from such solution.

16. A process for producing extracellular microbial lipopolysaccharides which comprises (A) inoculating an aqueous fermentation medium containing a growth sustaining amount of the assimilable salts of one or more fatty acids with a culture of Acinetobacter Sp. ATCC 31012 or its mutants; (B) aerobically growing the microorganism in such fermentation medium, while adding additional amounts of such fatty acid salt or salts to sustain growth, aerating the fermentation medium sufficiently to give an oxygen flow rate of about 190 millimoles per liter per hours or higher, and maintaining the pH of the fermentation medium in the range from about 6.2 to about 6.7 and the temperature of the fermentation medium in the range from about 25° C. to about 35° C., for a period of time sufficient to produce extracellular microbial protein-associated lipopolysaccharides (herein collectively called "α-emulsans") in which the lopopolysaccharide components (herein collectively called "apo-α-emulsans") are N- and 0-lipoacylated heteropolysaccharides composed of (i) from about 20 to about 35 percent by weight of D-galactosamine; (ii) from about 30 to about 35 percent by weight of an aminouronic acid; and (iii) from about 7 to about 19 percent by weight of fatty acid esters in which the fatty acids contain from about 10 to about 18 carbon atoms and are characterized by an average equivalent weight from about 200 to about 230, from about 50 to about 70 percent by weight of such fatty acids being composed of 2-hydroxydodecanoic acid and 3-hydroxydodecanoic acid; and (C) separating substantially all of the microbial cell mass from the emulsan-containing culture medium.

17. A process for producing α-emulsans according to claim 16, in which the fermentation inoculum is a late exponential growth of the microorganism.

18. A process for producing α-emulsans according to claim 16, in which the fermentation is conducted in a fresh water medium which contains from about 4 to about 50 mM of a divalent cation.

19. A process for producing α-emulsans according to claim 16, in which the fermentation is conducted in a sea water medium.

20. A process for producing α-emulsans according to claim 16, in which the post-inoculation growth of the microorganism is continued for a period of time between about 24 to about 30 hours.

21. A process for producing α-emulsans according any of claims 16, 17, 18, 19 or 20, in which the carb source is one or more salts of fatty acids containi from 10 to 18 carbon atoms and selected from the gro consisting of saturated fatty acids, unsaturated fat acids and hydroxy-substituted fatty acids.

22. A process for producing α-emulsans according any of claims 16, 17, 18, 19 or 20, in which the carb source is sodium pamitate.

23. A process for producing α-emulsans in acco dance with claim 16, in which the fermentation medit contains (1) a greater than growth-sustaning amount at least one assimilable nitrogen-containing compour and (2) a growth-sustaining amount of one or mc assimilable phosphorus-containing compounds.

* * * * *

UNITED STATES PATENT AND TRADEMARK OFFICE
CERTIFICATE OF CORRECTION

PATENT NO. : 4,230,801

DATED : October 28, 1980

INVENTOR(S) : David L. Gutnick and Eugene Rosenberg

It is certified that error appears in the above—identified patent and that said Letters Patent is hereby corrected as shown below:

In the Abstract, line 1, "Arthrobacter" should read -- Acinetobacter --.
Column 2, line 41, "αEmulsan" should read -- α-Emulsan --.
Column 2, line 45, "Absorption" should read -- Adsorption --.
Column 3, line 38, "31012and" should read -- 31012 and --.
Column 4, line 64, "β-emulsans and β-emulsans" should read -- α-emulsans and β-emulsans --.
Column 5, line 68, "such as apo-α-emulsans" should read -- such apo-α-emulsans --.
Column 6, line 29, "Actinetobacter" should read -- Acinetobacter --.
Column 6, line 44, "word meaning" should read -- word απο meaning --.
Column 6, line 50, "lipoploysaccharide" should read -- lipopolysaccharide --.
Column 6, line 61, after the phrase "α-emulsans" insert the phrase -- are named "apo-α-emulsans". --
Column 6, between lines 61 and 62, insert the following paragraph:

-- The name "β-emulsans" defines those extracellular microbial protein-associated lipopolysaccharides produced by Acinetobacter Sp. ATCC 31012 and its mutants in which the lipopolysaccharide components (i.e., without the associated protein) are completely N-acylated and partially O-acylated heteropolysaccharides made up of major amounts of D-galactosamine and an aminouronic acid, the lipopolysaccharide components containing less than 5

UNITED STATES PATENT AND TRADEMARK OFFICE
CERTIFICATE OF CORRECTION

PATENT NO. : 4,230,801                    Page 2 of 4

DATED : October 28, 1980

INVENTOR(S) : David L. Gutnick and Eugene Rosenberg

It is certified that error appears in the above—identified patent and that said Letters Patent is hereby corrected as shown below:

percent by weight of fatty acid esters in which (1) the fatty acids contain from about 10 to about 18 carbon atoms; and (2) less than 50 percent by weight of such fatty acids are composed of 2-hydroxydodecanoic acid. The deproteinized β-emulsans are named "apo-β-emulsans". --

Column 7, line 8, "bipolymers" should read -- biopolymers --.
Column 7, line 21, "word meaning" should read -- word προτο meaning --.
Column 7, line 24, "προτο" should read -- νεοξ --.
Column 7, line 32, "recominants" should read -- recombinants --.
Column 8, line 29, "subdivded" should read -- subdivided --.
Column 8, line 41, "nalkanes" should read -- n-alkanes --.
Column 8, line 58, "alkybenzenes" should read -- alkylbenzenes --
Column 8, line 62, "and particular" should read -- and a particular --.
Column 10, line 32, "lipopolysacchrides" should read -- lipopolysaccharides --.
Column 11, line 27, "source" should read -- sources --.
Column 16, line 40, "lypophilization" should read -- lyophilization --.
Column 17, line 12, "α-emulsion" should read -- α-emulsan --.
Column 17, line 36, "acinetobacter" should read -- Acinetobacter --.
Column 17, line 38, "39-40%" should read -- 30-40% --.
Column 17, line 43, "cetytrimethyl" should read -- cetyltrimethyl --.
Column 18, line 51, "PERCIPITATION" should read -- PRECIPITATION --.

UNITED STATES PATENT AND TRADEMARK OFFICE
CERTIFICATE OF CORRECTION

PATENT NO. : 4,230,801  
DATED : October 28, 1980  
INVENTOR(S) : David L. Gutnick and Eugene Rosenberg It is certified that error appears in the above—identified patent and that said Letters Patent is hereby corrected as shown below:

Column 20, line 34, "10°C." should read -- 100°C. --  
Column 21, line 9, "galactose oidase" should read -- galactose oxidase --.  
Column 23, line 22, "of 6.06" should read -- or 6.06 --.  
Column 23, line 30, "(1-V)" should read -- (1-V$\rho$) --.  
Column 23, line 31, "and is" should read -- and $\rho$ is --.  
Column 23, line 35, "viscosity, sedimentation" should read -- viscosity, $\eta$, sedimentation --.  
Column 23, line 51, "2 angles" should read -- 2$\theta$ angles --.  
Column 23, line 56, "2°" should read -- 2$\theta$° $\frac{}{o}$--.  
Column 23, line 56, "d(A)" should read -- d(Å) --.  
Column 24, line 5, "0.712 cm'gm$^{-1}$" should read --$_o$0.712 cm$^3$gm$^{-1}$--.  
Column 24, line 15, "1000 A" should read -- 1000 Å --.  
Column 24, line 68, "(C)" should read -- (c) --.  
Column 26, line 37, "concentration " should read -- concentrations --.  
Column 26, line 38, "half-mixture" should read -- half-maximum --.  
Column 26, line 41, "trubidities" should read -- turbidities --.  
Column 26, lines 52-53, "Emulsins" should read -- Emulsions --.  
Column 27, line 5, "of" should read -- or --.  
Column 28, line 15, "r" should read -- r --.  
Column 31, line 3, "Arthrobacter" should read -- Acinetobacter --.  
Column 32, line 55, "acinetobacter" should read -- Acinetobacter --.  
Column 32, line 56, "or" should read -- on --.  
Column 32, line 58, "product" should read -- produce --.  
Column 37, line 44, "innoculation" should read -- inoculation --.  
Column 38, line 14, "iniated" should read -- initiated --.

Page 3 of 4

UNITED STATES PATENT AND TRADEMARK OFFICE
CERTIFICATE OF CORRECTION

PATENT NO. : 4,230,801

DATED : October 28, 1980

INVENTOR(S) : David L. Gutnick and Eugene Rosenberg

It is certified that error appears in the above—identified patent and that said Letters Patent is hereby corrected as shown below:

Column 40, line 7, "bipolymer" should read -- biopolymer --.
Column 40, lines 38-39, "without removal" should read
  -- without prior removal --.
Column 40, line 52, "lypophilized" should read -- lyophilized --.
Column 41, line 16, "bipolymer" should read -- biopolymer --.
Column 43, line 63, "emulsifier s" should read -- emulsifiers --.
Column 48, line 16, "2,5000 rpm" should read -- 25,000 rpm --.
Column 49, line 5, "0.1 ml. 0.2 ml." should read -- 0.1 ml.,
  0.2 ml.,--
Column 49, line 39 (Table XIX, right-hand column), "21" should
  read -- 12 --.
Column 50, line 18, "Aghi" should read -- Agha --.
Column 51, line 15, "α-emulsions" should read -- α-emulsans --.
Column 51, line 37, "foir" should read -- for --.
Column 51, line 47, "condutcted" should read -- conducted --.
Column 51, line 50, "a" should read -- A --.
Column 52, line 16, "immisible" should read -- immiscible --.
Column 52, line 61, "lopopolysaccharide" should read
  -- lipopolysaccharide --.
Column 54, line 12, "pamitate" should read -- palmitate --.
Column 54, line 15, "sustaning" should read -- sustaining --.

Signed and Sealed this

Twenty-fourth Day of March 1981

[SEAL]

Attest:

RENE D. TEGTMEYER

Attesting Officer    Acting Commissioner of Patents and Trademarks